(12) United States Patent
Meyer

(10) Patent No.: US 8,329,685 B1
(45) Date of Patent: Dec. 11, 2012

(54) ENHANCEMENT OF THE ACTION OF ANTI-INFECTIVE AGENTS AND OF CENTRAL AND PERIPHERAL NERVOUS SYSTEM AGENTS AND TRANSPORTATION OF NUCLEIC ACID SUBSTANCES

(75) Inventor: Petrus Johannes Meyer, George (ZA)

(73) Assignee: North West University, Potchefstroom (ZA)

( * ) Notice: Subject to any disclaimer, the term of this patent is extended or adjusted under 35 U.S.C. 154(b) by 408 days.

(21) Appl. No.: 10/345,204

(22) Filed: Jan. 16, 2003

Related U.S. Application Data

(63) Continuation-in-part of application No. PCT/ZA01/00098, filed on Jul. 19, 2001, which is a continuation-in-part of application No. PCT/ZA01/00099, filed on Jul. 19, 2001, which is a continuation-in-part of application No. PCT/ZA01/00100, filed on Jul. 19, 2001.

(51) Int. Cl.
*A61K 31/407* (2006.01)
*A61K 31/00* (2006.01)
*A61K 31/495* (2006.01)
*A61K 31/47* (2006.01)
*A61K 31/44* (2006.01)
*A61K 31/42* (2006.01)
*A61K 31/40* (2006.01)
*A61K 31/13* (2006.01)
*A01N 43/50* (2006.01)

(52) U.S. Cl. .............. 514/210.09; 514/211.03; 514/298; 514/255.05; 514/312; 514/357; 514/374; 514/385; 514/396; 514/422; 514/424; 514/669

(58) Field of Classification Search .................. 514/183
See application file for complete search history.

(56) References Cited

U.S. PATENT DOCUMENTS 5,633,284 A * 5/1997 Meyer ............................ 514/718
6,416,740 B1 * 7/2002 Unger ........................... 424/9.52

FOREIGN PATENT DOCUMENTS

DE 2647671 * 4/1978
WO WO-9606152 * 2/1996

* cited by examiner

*Primary Examiner* — Alton Pryor
(74) *Attorney, Agent, or Firm* — Rothwell, Figg, Ernst & Manbeck, P.C.

(57) ABSTRACT

The invention provides a method of enhancing the action of a pharmaceutical agent selected from the group consisting of the anti-infective agents, the group comprising of the antimicrobial agents, the anthelmintic agents and the anti-ectoparasitic agents, but excluding coal tar solution and H1-antagonist antihistamines, and from the group consisting of the CPNS agents selected from the group of compounds acting on the central or peripheral nervous system, but excluding coal tar solution and H1-antagonist antihistamines and also excluding anti-inflammatory, analgesic and antipyretic agents and also provides an enhanced method for the administration of a nucleic acid substance to the cells of an animal, a plant or a micro-organism. The method is characterized in that the agent or nucleic acid substance is formulated with an administration medium which comprises a solution of nitrous oxide gas in a pharmaceutically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20:5ω3], decosahexaenoic acid [C22:6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil with ethylene oxide. The formulations of such agents or substances form part of the invention.

5 Claims, 4 Drawing Sheets

Bioavailability of Rifampicin in the MZL formulated Rifamzaloid vs its comparator Rifampin Bioavailability of IZONIAZID Bioavailability of Pyrazinamide

ENHANCEMENT OF THE ACTION OF ANTI-INFECTIVE AGENTS AND OF CENTRAL AND PERIPHERAL NERVOUS SYSTEM AGENTS AND TRANSPORTATION OF NUCLEIC ACID SUBSTANCES

CROSS-REFERENCE TO RELATED APPLICATIONS

This application is a continuation-in-part of PCT International Applications PCT/ZA01/00098, PCT/ZA01/00099, and PCT/ZA01/00100, all filed Jul. 19, 2001, and all designating the U.S.

FIELD OF THE INVENTION

This invention relates to pharmaceutical preparations (which expression is herein intended to include veterinary preparations) for use in combating infective organisms afflicting the animal body (which expression is herein intended to include the human body).

This invention also relates to pharmaceutical preparations (which expression is also herein intended to include veterinary preparations) for use in treating afflictions of the animal body affecting the central and/or peripheral nervous system of an animal (which expression is again herein intended to include the human body) in need of treatment.

This invention further relates to preparations for use in transporting nucleic acid substances to and into cells of a plant or an animal body (which expression is again herein intended to include the human body), either in vivo or in vitro, or of a micro-organism. This invention is more particularly concerned with the administration of substances based on nucleic acid to patients for the purpose of the transportation thereof through the body of the patient and the ultimate delivery thereof into cells either generally or of a targeted cell type. It therefore finds application in what is colloquially referred to as gene therapy as will become evident from the disclosure below. The invention is also concerned with the transfection of plants and micro-organisms with DNA thereby to affect the genetic properties of such plant or organism.

BACKGROUND TO THE INVENTION

In EP 93912877.3 and U.S. Pat. No. 5,633,284 and their equivalents the applicant disclosed that dermatological or topical compositions comprising the combination of nitrous oxide [$N_2O$] and at least one fatty acid, or lower alkyl ester thereof in a dermatologically acceptable carrier medium are useful in the treatment of a variety of skin, muscle and joint disorders. It also disclosed therein that such combinations may beneficially also include additional active ingredients.

The following active ingredients are specifically mentioned in this regard: coal tar solution, collagen, nicotinamide, nicotinic acid, lanolin, vitamin E, methyl salicylate, arnica and H1-antagonist antihistamines of which only diphenhydramine chloride is specifically mentioned.

Known anti-bacterial, anti-viral or anti-fungal agents were not amongst the active ingredients specifically mentioned in the patents but mention was made therein that coal tar solution (also known as Liquor Picis Carbonis) may be used (as a supplementary active ingredient and that the resultant preparation is suitable for use in the treatment of, inter alia fever blisters, herpes simplex, shingles and chicken pox. While all of these conditions are caused by viral infections, the disclosures in these patents do not refer to that fact.

It is also disclosed in these patents that, in addition to the coal tar solution the composition may also contain an H1-antagonist antihistamine (e.g. diphenhydramine hydrochloride) and may in that form be used in the treatment of atopic and allergic conditions manifesting in skin irritations such as eczema, dermatitis and ringworm. The latter of these conditions is caused by a fungal infection. Again the disclosures in issue do not refer specifically to that fact.

It further disclosed an alternative composition in which the coal tar solution formulation is further provided with collagen and lanolin and this formulation was found to be useful in the treatment of persons suffering from acne vulgaris. Bacteria are involved in the condition but no mention was made of such involvement in those patents.

Since coal tar solution is in itself not known to be an anti-viral, anti-fungal or antibacterial agent, and has merely been mentioned as being weakly antiseptic, the aforementioned disclosures would not have been understood as suggesting that the nitrous oxide and fatty acid combination has any beneficial effect on the anti-viral or anti-fungal or anti-bacterial activity of any recognised anti-viral or anti-fungal or anti-bacterial agent or to have disclosed that such properties are displayed by coal tar solution. As will appear below the enhancement of the anti-bacterial, anti-fungal or anti-viral properties of known agents lie at the very heart of this invention.

Within the context of the disclosure in the abovementioned patent family the notional addressee most likely would, as did the inventor, have understood the role of the coal tar solution to sooth the itching and to assist in the repairing and healing of the skin which was damaged as a result of the infections/conditions in issue.

No agent known for having an effect on the central or peripheral nervous system, was amongst the active ingredients specifically mentioned in these patents. Mention was made therein that coal tar solution (also known as Liquor Picis Carbonis) may be used as a supplementary active ingredient and that the resultant preparation is suitable for use in the treatment, inter alia, of psoriasis, eczemaceous conditions and dermatitis. It is also disclosed in these patents that, in addition to the coal tar solution the composition may also contain an H1-antagonist antihistamine (e.g. diphenhydramine hydrochloride) and that such a preparation may beneficially be used in the treatment of atopic and allergic conditions manifesting in skin irritations such as eczema and dermatitis. The aforementioned conditions have since the date of the above patents come to be regarded by some writers on the topic as manifestations in the skin of underlying disorders which have or include a neurological, or immunological, or some even suggest a neuro-immunological cause. These patents however do not refer to that explanation. It further gives no hint that the effects obtained are the result of any form of systemic operation of any of the components of the formulation. Coal tar liquid is not known to be an agent acting on the central nervous system. Insofar as these patents may be seen to proffer any explanation at all for the results obtained, which is not what the applicant contends for, it is suggested that such explanation would, within the context of the disclosures therein, point to a local effect of soothing irritation and of repairing of skin and associated tissue damage as a result of the conditions mentioned therein. These are psoriasis, shingles, fever blisters, chicken pox, acne, chilblains, eczema, chloasmas, alopecia, dermatitis, ringworm and burn wounds.

The concept of introducing heterologous genetic material into the cells of an organism for the purpose of allowing such genetic material to be incorporated into the cellular DNA of such organism is well known. It is now routinely exercised in vitro and various methods have been developed for the introduction of such heterologous genetic material into the cells of an organism.

The most established of these methods is commonly referred to as the gene gun technique. By this technique genetic material is quite literally shot into the cells of the organism. While some of the cells do not survive the blast, those that do survive are caused to proliferate. Some of these proliferating survivors will have incorporated into its own genome the genetic material shot into it in the form of the DNA. The gene so incorporated may eventually be expressed to yield the product coded for by the DNA so introduced into the organism. It is also known to make use of other forms of vectors by which a gene which is required to be expressed is introduced into an organism. Such vectors include viruses.

While these techniques work adequately in the appropriate in vitro environment on lower organisms such as bacteria, they are not regarded as being generally suitable for implementation in vivo for the introduction of genetic material into a living animal, such as man. The harshness of the gene gun technique by its very nature renders that technique generally unsuitable for in vivo application. It is further generally regarded to be advisable not to expose animals or human beings unnecessarily to viral infections, let alone where such infections are by transgenic viruses, the full genetic nature and potential for mutation of which may be unknown.

There has thus been a long-felt need for an appropriate process by which genetic material may be introduced into selected cells there to express and yield a desired medicinally active substance.

This need is sought to be addressed, inter alia by the disclosure contained in U.S. Pat. No. 6,258,789 (German, et al.) and the patents cited during the examination thereof. German et al discloses a method of delivering a secreted protein into the bloodstream of a mammalian subject by introducing into the gastro-intestinal tract of a mammalian subject, by oral administration, a construct comprising a nucleic acid molecule encoding the desired secreted protein and a promoter sequence operably linked to the nucleic acid molecule, wherein said construct is not packaged in a viral particle, and wherein the method involves introducing the nucleic acid construct into the intestinal epithelial cells of the animal in question so that secretion of the protein takes place at that locus to be available for absorption into the body from the digestive tract.

No agent based on nucleic acid was amongst the active ingredients specifically mentioned in the patents mentioned above.

In WO97/17978 and U.S. Pat. No. 6,221,377 and in corresponding patents and pending patent applications in other jurisdictions the present applicant disclosed that the action of analgesic, anti-inflammatory and anti-pyretic drugs may be enhanced by administering such drugs in conjunction with a medium which comprises nitrous oxide and at least one long chain fatty acid selected from the group consisting of oleic acid, linoleic acid, alpha-linolenic acid, gamma linolenic acid, arachidonic acid, and any of the $C_1$ to $C_6$ alkyl esters of such long chain fatty acids, mixtures of such acids and mixtures of such esters. The medium may comprise the mixture known as Vitamin F Ethyl Ester and may optionally further comprise eicosapentaenoic acid [C20: 5ω3] and decosahexaenoic acid [C22: 6ω3].

While these applications do disclose a systemic effect in that the formulations are, for example, topically applied or orally administered to have an effect, say, in an affected joint or muscle, the specification again fails to disclose the mode or route of transport of the active ingredient from its site of administration to its locus of effect, and speculation in this regard would probably be based on ex post facto hindsight.

It has now surprisingly been found that the aforesaid medium and media related thereto has the ability remarkably to enhance the action of known anti-infective agents. The expression "anti-infective agents" as used herein is intended to have its extended meaning and to include the antimicrobial agents, the anthelmintic agents and the anti-ectoparasitic agents, but to exclude coal tar solution and H1-antagonist antihistamines.

The exclusion of coal tar solution and H1-antagonist antihistamines from the ambit of the present invention is introduced without thereby conceding that the aforementioned patents and applications contain any disclosure of any anti-infective agent properties of such excluded compounds, or that such properties are obvious in the light of the disclosures in such patents or applications. Such inferences are specifically denied. The exclusion is introduced simply to avoid what is anticipated to be a potential obstacle to the grant of a patent in respect of an insignificant part of potential subject matter which part in itself is not considered worth contesting during examination as it might unduly delay the implementation in practice of the significant features of the present invention. It is expected that the remaining bulk of the subject matter of the present invention will greatly contribute to the accessibility of medicines for the treatment of a large range of infections, including secondary infections in HIV-compromised patients, at significantly reduced costs.

The expressions "anthelmintic agents" and "anti-ectoparasitic" agents are further intended to cover both agents which serve to destroy and those which serve to inhibit the proliferation of helminths or ecto-parasites. Those expressions are hence also intended to be understood in the wider sense of these terms. The expression "antimicrobial agents" is similarly intended to be understood in the wider sense of that word and hence to have the meaning ascribed thereto in The McGraw-Hill Dictionary of Scientific and Technical Terms $2^{nd}$ Ed 1978, namely all chemical compounds that either destroy or inhibit the growth of microscopic and sub microscopic organisms. This term is further specifically intended to include all the compounds falling within the Pharmacological Classification 20 set out as part of Regulation 5(1) of the General Regulations made in terms of the South African Medicines and Related Substances Control Act, Act 101 of 1965, as well as the active ingredients of all products falling within class 18 of the pharmacological classification employed in the Monthly Index of Medical Specialities ("MIMS") published by Times Media in South Africa. It is thus intended to include:

the anti-bacterial agents (including both antibiotics and substances other than antibiotics such as the sulfonamides, the erythromycins and other macrolides, the aminoglycocides, the tetracyclines, the chloramphenicols and the quinolones);
the anti-fungal agents;
the anti-viral agents (including anti-retroviral agents);
the anti-protozoal agents;
the tuberculostatics;
the anti-leprotics;
the germicides;
and
the spirochaeticides.

The surprising finding of enhancement of action of the anti-infective agents referred to above is made against the background of the fact that there appears to be no earlier suggestion in the literature to the effect that either nitrous oxide or the long chain fatty acids used in the formulation referred to above, and hence also not the combination of these, has any effect whatsoever on the sensitivity of any micro-organism to any anti-infective agent.

The present invention is specifically, though not exclusively aimed at the enhancement of the action of anti-mycobacterial agents, and particularly those used in the treatment of patients infected with *Mycobacterium tuberculosis* (M.Tb.). This organism is one of the most significant human pathogens. It is responsible for an estimated seven million new cases of tuberculosis annually, and an estimated three million deaths worldwide. Of particular concern is the emergence of tuberculosis (TB) as an increasing cause of morbidity and mortality among persons compromised by human immune-deficiency virus (HIV) infection.

Although the prevalence of tuberculosis in developed countries declined in the first few decades of the 1900's, this trend has reversed and an increased incidence of tuberculosis has been reported in many countries. Africa alone is estimated to have approximately 170 million TB patients. In South Africa the incidence of tuberculosis is also rising and is at different levels in different population groups. The chapter on Tuberculosis in the 1999 edition of *South African Health Review* (available at http://www.hst.org.za/sahr/) opens with the shocking statement that: "Despite the availability of effective and affordable treatment, the number of South Africans dying from tuberculosis continues to increase". It is echoed by the summary of the startling overview in which it is recorded that "A reported incidence of 254 cases per 100 000 for the period 1996-1998 combined with low cure rates, indicate that the epidemic is still out of control. Rising levels of HIV infection and multi-drug resistant TB (MDR TB) represent additional threats to TB control efforts." The number of reported cases of pulmonary TB (PTB) is reported in the Review to have risen from 90628 to 110016 new reported cases per year over the period 1996 to 1998, the estimated report rate having increased over the same period from 64% to 71%. Some of the provinces in South Africa contributed significantly to the national average TB incidence figure of 254 referred to above. The quoted Review reflects the figure for Eastern Cape as 388, for the Northern Cape as 360, the Free State as 338 and the Western Cape as about 500 per 100000, almost double the national average. It has been reported elsewhere that the highest incidence of TB in the country is found in certain communities in the Western Cape where the estimated incidence is as high as 1400 per 100000.

Re-infection of patients is an ever-increasing problem and has been shown to be a function of reactivation of TB in patients not completing their therapy. It is also often associated with the appearance of drug resistant M.Tb. in the patient. The exact mechanism whereby drug resistance develops in mycobacteria is not yet fully understood, but the economic consequences thereof are a reality. The occurrence of drug resistant strains of M.Tb., generally known as multi-drug resistant Tuberculosis ("MDR TB") is also referred to in the aforementioned *South African Health Review* 1999. It states: "Accurate figures for MDR TB are currently not available but surveys in three provinces (Western Cape, Mpumalanga and Gauteng) indicate a rate of 1% in new MDR TB cases, 4% in retreatment cases. This translates to at least 2 000 newly active cases of MDR TB in South Africa each year. MDR TB is extremely expensive to treat—R25 000 to R30 000 per patient for the drugs alone as opposed to less than R200 for a new patient with ordinary TB. Such patients generally also require to be hospitalised for long periods of time (usually between six and eighteen months), adding significantly to the cost of their treatment"

In an attempt to reduce discontinuance of TB-treatments which has been implicated in reinfections and the development of resistant strains, the practice of directly observed treatment or DOTS has been resorted to, with some, but based on the foregoing quotes, not complete success.

Iron, heavy metals, and excessive alcohol consumption (an inherent feature of some identified high incidence TB communities) generate harmful reactive oxygen species which have been shown to be involved in the auto-oxidation of Rifampicin, an antibiotic anti-mycobacterial agent used in the treatment of tuberculosis, thereby generating more radical species. These free radicals have been implicated in the liver toxicity experienced with use of Rifampicin.

These problems associated with TB have led to the investigations associated with the present invention.

It has also surprisingly been found that the aforesaid medium has the unexpected property that it displays a remarkable ability to enhance the action of known agents affecting the central and/or peripheral nervous system, such known agents being other than the group which consists of coal tar solution, H1 antagonist antihistamines, the analgesics, the anti-inflammatories and the antipyretics. These agents will hereinafter collectively be referred to as "CPNS agents" which term is for purposes of this specification intended to embrace those biologically active compounds which perform their action on the central or peripheral nervous system of the human or animal body, but to exclude recognised anti-inflammatory, analgesic and antipyretic substances and also excluding coal tar solution and H1 agonist antihistamines. Subject to these exclusions it therefore includes the compounds which fall within Class 1 of the Pharmacological Classification set out as part of Regulation 5(1) of the General Regulations made under The Medicines and Related Substances Control Act, Act 101 of 1965, and the active ingredients of all products falling within Class 1 of the pharmacological classification currently employed in the Monthly Index of Medical Specialities ("MIMS") published by Times Media in South Africa, but excluding the analgesic, anti-inflammatory and anti-pyretic compounds which falls within the above two partially overlapping classes. Examples of some of the compounds falling within the group is described in greater detail below.

The exclusion of coal tar solution and H1-antagonist antihistamines, and of anti-inflammatories, analgesics and anti-pyretics from the ambit of the present invention is introduced without thereby conceding that the aforementioned patents and applications contain any disclosure of any CPNS agent properties of such excluded compounds, or that such properties are obvious in the light of the disclosures in such patents or applications. Such inferences are specifically denied. The exclusion is introduced simply to avoid what is anticipated to be a potential obstacle to the grant of a patent in respect of a part of the subject matter which part in itself is not considered worth contesting during examination as it might unduly delay the implementation in practice of the significant features of the present invention. It is expected that the remaining bulk of the subject matter of the present invention will greatly contribute to the accessibility of medicines for the treatment of a large range of ailments.

It has now further surprisingly been found that the aforesaid medium and other similar media have the unexpected property that it may also be used as a delivery vehicle adapted to be used for the delivery, into the nucleus of, or generally to, an animal cell, of nucleic acid compounds.

It was pointed out in WO97/17978 referred to above that nitrous oxide is a natural gas which is also produced synthetically, and also known by the trivial name "laughing gas"

which has been in use for many years as an inhalation anaesthetic and analgesic, particularly in dentistry.

It was further stated that nitrous oxide has been reported to have a synergistic or potentiating effect on halothane and other gaseous anaesthetics [See Goodman & Gilman's *The Pharmacological Basis of Therapeutics* 8th Ed. 1990 pp. 298-300].

Since such known synergism or potentiation is based on the use of nitrous oxide administered by inhalation, and since the use of nitrous oxide on its own as an anaesthetic and analgesic has likewise been in the form of an inhalation agent, the use of nitrous oxide for all these purposes have been confined to hospitalised patients or, at best, to treatments carried out by medical practitioners in their consulting rooms, or treatments carried out by or under supervision of a nurse in charge of a home-care patient.

Nitrous oxide is known to be soluble in water and it has been reported that at 20° C. and 2 atm pressure one liter of the gas dissolves in 1.5 liters of water, see The Merck Index 10th Ed. p. 6499.

Nitrous oxide is also known for its use as a propellant gas, mainly as a substitute for propellant gases such as chlorofluorocarbons, and more particularly to produce a food product mousse such as whipped cream or chocolate mousse or quick-breaking foams for hair treatment preparations. See in this regard U.K. Patent 1033299, U.K. Patent 1105919 and European Patent Application EPA-0123827. None of these prior publications suggests that the nitrous oxide gas plays any other role than a physical one, i.e. to expand on being depressurised and thereby to create a mousse or foam. In fact it is typically regarded as an inert in these applications and useful due to the fact that it is colourless, odourless and tasteless but soluble in water and oils.

There appears to be no suggestion in the literature, other than the applicants own prior patents and patent applications referred to above, that aqueous solutions of nitrous oxide might have any effect on man or animals. As far as the present applicant knows, it has also never been suggested that nitrous oxide may be used in conjunction with any anti-infective agent to enhance the known action of such agent.

It is known in the pharmaceutical field to formulate active ingredients in so-called liposomal formulations. Unlike the present invention which is based on formulations containing long chain fatty acids and esters thereof the liposomes are based on a clearly distinguishable group of compounds namely the phospholipids, and generally also contain cholesterol as a stabilising agent and may further contain lisolecitein. These compounds or classes form no part of the present invention and, in case it is necessary to do so, are specifically excluded from the group of long chain fatty acids and derivatives thereof incorporated in the method or formulation of the invention.

Objects of the Invention

It is an object of the present invention to provide a method of enhancing the known action of anti-infective agents and to provide pharmaceutical preparations of such anti-infective agents which preparations have enhanced action compared to the action of known formulations containing the same agents.

It is another object of the present invention to provide a method of enhancing the action of CPNS agents and to provide pharmaceutical preparations of such agents which preparations have enhanced action compared to the action of known formulations containing the same agents.

It is a further object of the present invention to provide a method and formulation for the transportation and delivery of nucleic acid substances into cells of an animal, a plant or a micro-organism. The term "animal" is herein intended to be interpreted in its wide meaning to include man and insect. The term "micro-organism" is herein intended to include single and multi-cellular organisms such as parasites. The invention is thus concerned with all forms of life in which nucleic acid substances in the form of DNA or RNA determine the genetic properties of that form of life.

These objects stem from the observations made by present applicant in respect of a selection of agents falling within the group of active agents as herein defined, which can advantageously be formulated with nitrous oxide and an oil based on long chain fatty acids disclosed herein, to elicit a more potent response, for each agent according to its own inherent properties, or to evoke such response more rapidly than it does when used by conventional administration of the agent in issue.

Statements of the Invention (i) Anti-Infectives

According to the present invention there is provided a method of enhancing the action of an anti-infective agent characterised in that the agent is selected from the group comprising antimicrobial agents, the anthelmintic agents and the anti-ectoparasitic agents, but excluding coal tar solution and H1-antagonist antihistamines, comprising the step of formulating the agent with an administration medium which comprises a solution of nitrous oxide gas in a pharmaceutically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil with ethylene oxide.

According to a further aspect of the present invention there is provided a pharmaceutical preparation comprising an anti-infective agent characterised in that it is selected from the group comprising antimicrobial agents, the anthelmintic agents and the anti-ectoparasitic agents, but excluding coal tar solution and H1-antagonist antihistamines, which agent is formulated with an administration medium which comprises a solution of nitrous oxide in a pharmaceutically acceptable carrier solvent for the gas and which includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and the derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil, with ethylene oxide.

The administration medium preferably includes the eicosapentaenoic acid [C20: 5ω3] and/or decosahexaenoic acid [C22: 6ω3] as additional long chain fatty acids to at least one of the other components of the carrier medium defined above.

The reaction product of hydrogenated natural oils composed largely of ricinoleic acid based oils with ethylene oxide is preferably produced from castor oil of which the fatty acid content is known to be predominantly composed of ricinoleic acid. This product is known as PEG-n-Hydrogenated Castor Oil. A range of such products is marketed by BASF under the trade description of Cremophor RH grades. Glycerol-polyethylene glycol ester of ricinoleic acid is also marketed by the same company but under the trade description of Cremophor EL.

The carrier solvent for the nitrous oxide gas may be water or any of the pharmaceutically acceptable alcohols, ethers, oils or polymers such as a polyethylene glycol or the like. The oil may be organic or mineral oil. The organic oil may be an essential oil based on long chain fatty acids having between 14 and 22 carbon atoms in the fatty acid. The oil may also be of either natural or synthetic origin and, if of natural origin, it may be either plant oil or animal oil. As plant oils those rich in gamma linolenic acid [GLA] are preferred and as animal oil dairy cream may be used.

In the preferred form of the invention the solution is an aqueous solution saturated with nitrous oxide. Preferably the water is deionised and purified to be free of microbes.

When the formulation containing the anti-infective agent to be enhanced by means of the nitrous oxide is to be in a liquid (including an encapsulated liquid) presentation for oral administration or in a nasal or bronchial or pulmonary spray or in the form of an injectable formulation, such formulation may incorporate, as part of the administration medium, water or acceptable other liquid into which the nitrous oxide is dissolved and in which the fatty acid or ester thereof is either dissolved or suspended or emulsified along with the anti-infective agent to be enhanced by being formulated therewith.

Likewise, where the anti-infective agent is to be administered to the patient as a topical, buccal or vaginal cream or ointment, or as a suppository, the formulation used in making up such cream, ointment, or suppository may incorporate, along with the anti-infective agent to be enhanced, a quantity of water or other liquid containing, and preferably saturated with, nitrous oxide, the long chain fatty acid or ester thereof and the anti-infective agent formulated therewith, and, further, such additional excipients and carriers as are conventionally used in the pharmaceutical trade in making up such dosage forms.

The carrier solvent for the nitrous oxide gas may thus in an alternative formulation according to the invention be essentially non-aqueous and composed of least one fatty acid or ester thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils with ethylene oxide, required to be part of the formulation.

A formulation suited to transdermal application whether as an ointment, cream or lotion or in the form of a skin patch providing a reservoir for the formulation is also a preferred form of the formulation according to the invention.

The essential fatty acid, or ester thereof, component of the composition preferably comprises a mixture of esters of the fatty acids listed above. Thus, in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:

<$C_{16}$: 0
$C_{16.0}$: 8.3%
$C_{18.0}$: 3.5%
$C_{18.1}$: 21.7%
$C_{18.2}$: 34.8%
$C_{18.4}$: 28.0%
>$C_{18}$: 1.6%
unknown: 2.1%

It is further preferred to add to the formulation the long chain fatty acids known as eicosapentaenoic acid [C20:5ω3] and decosahexaenoic acid [C22:6ω3]. Such a product combination is available from Roche Lipid Technology under the trade name "Ropufa '30' n-3 oil".

It has been found by microscopic studies that the formulation of the anti-infective agents with a medium as herein described gives rise to the formation of minute, generally spherical bodies, within which, or attached to which the active ingredient is contained in a stable form and from which it is delivered at the site of action namely on or inside the infective agent.

The anti-infective agent utilised in the method or formulation according to the present invention may comprise any one or more of the vast spectrum of anti-infective agents as herein defined.

In a preferred form of the invention the anti-infective agent is selected from the group comprising:
the anthelmintics
the anti-ectoparasitcides
the anti-bacterial agents (including both antibiotics and substances other than
antibiotics);
the antifungal agents;
the anti-viral agents;
the anti-protozoal agents;
the tuberculostatics;
the anti-leprotics;
the germicides;
and
the spirochaeticides.

From amongst these anti-infective agents this invention is particularly concerned with the anti-bacterials and the tuberculostatics. These classes of agents overlap to some extent.

The anti-infective agent may in a specific application of the invention comprise an antimicrobial of the class of compounds known as the tuberculostatics or anti-mycobacterial compounds and may specifically be selected from the group consisting of Rifampicin, Isoniazid, Pyrazinamide, Ethambutol and combinations of any two or more of these.

It is a further aspect of the invention that the formulation, and specifically, though not exclusively, the anti-TB formulation of the invention, may be prepared to be adapted for pulmonary administration. In the case of the anti-TB formulation it will thereby bring the formulation into contact with the pathogen at a primary locus thereof and without passage through, or absorption from the digestive tract and possible subsequent passage through the liver.

The invention has not yet been demonstrated by empirical work to be applicable to all the agents listed below. However in respect of such anti-infective agents which have already been formulated with the aforementioned administration medium of the invention, and evaluated by different methods for the anticipated enhancement of anti-infective action, no negative result has as yet been seen despite the chemical diversity of the anti-infective agents which has been investigated. The applicant thus confidently expects, on the basis of the observations in respect of products representing a range of classes of such agents, that the invention will find general application across the entire spectrum of anti-infective agents embraced by the term as herein defined and of which some examples are set out below. It is part of the applicant's present postulations by which it seeks to find an understanding of the invention and to which it does not wish to be bound at this stage, that while the administration medium of the present invention serves to transport the anti-infective agent formulated therewith most efficiently through the human or animal body, that medium also plays an important role in transferring, by an as yet unexplained mechanism, the anti-infective agent through the outer membranes of and into the pathogenic organism thereby to cause an effective anti-infective dose of the agent rapidly to be achieved and to be maintained in the organism until it finally succumbs to the effect of the anti-infective agent.

It is in this respect that the applicant believes that the present invention will find general application despite the vast list of agents mentioned below. The following table sets out examples of the specific anti-infective agents with which this invention is concerned will now be identified with reference to the broad classes in which they fall and, in some cases, also with reference the respective indications for which such agents are indicated and, in some cases, further also with reference to the infective agent giving rise to the indication to be addressed which products comprise the following:

A. Sulphonamides
  1) Short-acting
    SULPHAPYRIDINE—
      1) Inflammatory bowel diseases and in rheumatoid arthritis
    SULPHADIAZINE—
      1) Nocardiosis (*Nocardia* species)
      2) Toxoplasmosis+Pyrimethamine
      3) Long term prophylaxis of rheumatic fever
    SULPHADIMIDINE—
    SULPHAFURAZOLE—
  2) Medium-acting:
    SULPHAMETHOXAZOLE—
  3) Long-acting:
    SULPHADIMETHOXINE—
    SULPHAMETHOXYDIAZINE—
    SULPHAMETHOXYPYRIDAZINE—
  4) Ultra-Long-acting:
    SULFADOXINE—
    SULFAMETOPYRAZINE—
  5) Topical sulphonamide:
    SILVER SULPHADIAZINE—
      1) Antibacterial in patients with burns
    MAFENIDE ACETATE—
      1) Antibacterial in patients with burns
    SULPHACETAMIDE—
  6) Other sulphonamides:
    SULPHAGUANIDINE—
      1) Gastrointestinal infections
    SULPHASALAZINE—
      1) Inflammatory bowel diseases and in rheumatoid arthritis
    SUCCINYLSULPHATHIAZOLE—
      1) Gastrointestinal infections
    PHTHALYLSULPHATHIAZOLE—
      1) Gastrointestinal infections
  7) SULPHONAMIDE COMBINATIONS:
    CO-TRIMOXAZOLE (Trimethoprim+Sulphamethoxazole)—
      1) Abscesses, Bacteremia, Endocarditis, Pneumonia, Osteomyelitis, Cellulitis and other diseases that are Methicillin-sensitive (*Staphylococcus aureus*)
      2) Pneumonia, Arthritis, Sinusitis, Otitis that are Penicillin-sensitive (*Streptococcus Pneumoniae*)
      3) Meningitis and Bacteremia (*Listeria monocytogenes*)
      4) Urinary tract infections, Bacteremia, Other
      5) Urinary tract and other infections (*Enterobacter* species)
      6) Typhoid fever, Paratyphoid fever, Bacteremia, Acute gastroenteritis (*Salmonella*)
      7) Acute gastro-enteritis (*Shigella*)
      8) Otitis media, Sinusitis, Pneumonia, Epiglottitis, Meningitis (*Haemophilus influenzae*)
      9) Chancroid (*Haemophilus ducreyi*)
      10) Brucellosis (*Brucella*)±Gentamicin
      11) Yersiniosis (*Yersinia enterocolitica*)
      12) Cholera (*Vibrio cholerae*)
      13) Meningitis (Flavobacterium meningosepticum)
      14) Melioidosis (*Pseudomonas pseudomallei*)
      15) Granuloma inguinale (Calymmatobacterium granulomatis)
      16) Legionnaires' disease (*Legionella Pneumophila*)
      17) Pulmonary lesions, Brain abscess, Lesions of other organs (*Nocardia asteroides*)
      18) Lymphogranuloma venereum, Trachoma, Inclusion conjunctivitis [blennotthea], Non-specific urethritis, Cervicitis (*Chlamydia trachomatis*)
      19) Pneumonia in impaired host [Mild or moderate disease, Moderately severe or severe disease] (Pneumocystis carinii)

B. Quinolones
  B1 First Generation
  NALIDIXIC ACID (oxolinic acid)
    1) Urinary tract infections
  CINOXACIN
    1) Urinary tract infections
  PIPEMIDIC ACID
  PIROMIDIC ACID
  ACROSOXACIN
  Quinolones
  B2 Second Generation
  CIPROFLOXACIN
    1) Abscesses, Bacteremia, Endocarditis, Pneumonia, Osteomyelitis, Cellulitis and Other infections [Methicillin-sensitive and Methicillin-resistant] (*Staphylococcus aureus*)+Rifampin
    2) Urinary tract infection (Enterococcus)
    3) Otitis, Sinusitis, Pneumonia (*Moraxella catarrhalis*)
    4) Penicillin-sensitive and Penicillinase-producing gonococcus (*Neisseria gonorrhoeae* (gonococcus))
    5) Carrier state (Post-treatment) (*Neisseria meningitidis* (meningococcus))
    6) Urinary tract infection and other infections, Bacteremia (*Escherichia coli*)
    7) Urinary tract and other infections (*Proteus mirabilis*)
    8) Urinary tract and other infections (*Enterobacter* species)
    9) Urinary tract infection, Pneumonia, Bacteremia (*Pseudomonas aeruginosa*)
    10) Urinary tract infection (*Klebsiella pneumoniae*)
    11) Typhoid fever, Paratyphoid fever, Bacteremia, Acute gastroenteritis (*Salmonella*)
    12) Acute gastroenteritis (*Shigella*)
    13) Otitis media, Sinusitis, Pneumonia (*Haemophilus influenze*)
    14) Chancrois (*Hameophilus ducreyi*)
    15) Plague (*Yersinia pestis*)
    16) Yersomopsis Sepsis (*Yersinia enterocolitica*)

17) Tualermia (*Francisella tularensis*)
18) Cholera (*Vibrio tularensis*)
19) Enteritis (*Campulobacter jejuni*)
20) Bacteremia, Endocarditis (Campylbacter fetus)
21) Legionnaires' disease (*Legionella pneumophila*)
22) Disseminated disease in AIDS (*Mycobacterium avium*—intracellulare)±Clarithromycin; ±Ethambutol; ±Clofamizine OFLOXACIN
1) Penicillin-Sensitive and Penicillinase-Producing gonococcus (*Neisseria gonorrhoeae* (gonococcus))
2) Urinary tract infection and other infections, Bacteremia (*Escherichia coli*)
3) Urinary tract and Other infections (*Proteus mirabilis*)
4) Urinary tract and Other infections (*Enterobacter* species)
5) Urinary tract infection (*Klebsiella pneumoniae*)
6) Typhoid fever, Paratyphoid fever, Bacteremia, Acute gastroenteritis (*Salmonella*)
7) Urinary tract infection (*Pseudomonas aeruginosa*)
8) Yersiniosis, Sepsis (*Yersinia enterocolitica*)
9) Cholera (*Vibrio cholerae*)
10) Enteritis (*Campylobacter jejuni*)
11) Bacteremia, Endocarditis (*Campylobacter fetus*)
12) Leprosy (*Mycobacterium leprae*)

NORFLOXACIN
1) Acute gastroenteritis (*Salmonella*)
2) Acute gastroenteritis (*Shigella*)

ENOXACIN
LOMEFLOXACIN
PEFLOXACIN
AMIFLOXACIN
FLEROXACIN
LEVOFLOXACIN
NADIFLOXACIN
RUFLOXACIN
SPARFLOXACIN
1) Active against *Streptococcus pneumoniae* and anaerobic bacteria.
TOSUFLOXACIN
ENROFLOXACIN C. Anti-Septic and Analgesic Agents for Urinary Tract Infections
METHENAMIN
1) Not a primary drug for the treatment of acute urinary tract infections, but it is of value for chronic suppressive treatment.
NITROFURANTOIN
1) Urinary tract infection (*Escherichia coli*)
MENAZOPYRIDINE
1) Is not a urinary antiseptic but it does have an analgesic action on the urinary tract and alleviates symptoms of dysuria, frequency, burning and urgency.

D. Penicillin
Narrow Spectrum
BENZYLPENICILLIN (Penicillin G) [acid-labile]
1) Pharyngitis, Scarlet fever, Otitis media, Sinusitis, Cellulitis, Erysipelas, Pneumonia, Bacteremia, Toxic shock-like syndrome and Other systemic infections (*Streptococcus pyogenes* [Group A])
2) Endocarditis, Bacteremia (*Streptococcus* [viridans group])±Gentamicin.
3) Bacteremia, Endocarditis, Meningitis. (*Streptococcus agalactiae* [Group B]) Aminoglycoside.
4) Bacteremia, Endocarditis, Brain and other abscesses, Sinusitis (*Streptococcus* [anaerobic species])
5) Pneumonia, Arthritis, Sinusitis, Otitis [Penicillin-sensitive and Penicillin-Resistant] Endocarditis, Meningitis, other serious infections [Penicillin-Sensitive] (*Streptococcus pneumoniae* [pneumococcus])
6) Endocarditis or other serious infections (bacteremia), Urinary tract infections (Enterococcus)+Gentamicin
7) Penicillin-sensitive gonococcus (*Neisseria gonorrhoeae*)+Probenecid.
8) Meningitis (*Neisseria meningitidis* [meningococcus])) "Malignant pustule", Pneumonia (*Bacillus anthracis*)
10) Endocarditis, Infected foreign bodies, Bacteremia (*Corynebacterium* species, aerobic and anaerobic [diphtheroids])±an Aminoglycoside or +Rifampin
11) Meningitis, Bacteremia (*Listeria monocytogenes*) ±Gentamicin
12) Erysipeloid (*Erysipelothrix rhusiopathiae*)
13) Gas gangrene (*Clostridium perfringens* and other species)
14) Tetanus (*Clostridium tetani*)
15) Urinary tract infection, Bacteremia, Other infections (*Escherichia coli*)+a Penicillinase inhibitor.
16) Urinary tract and other infections (*Proteus*, other species)+a β-Lactamase inhibitor
17) Wound infection (animal bites), Abscesses, Bacteremia, Meningitis (*Pasteurella multocida*)
18) Ulcerative pharyngitis, Lung abscess, Empyema, Genital infections, Gingivitis (Fusobacterium nucleatum)
19) Bacteremia, Arthritis, Endocarditis, Abscesses (*Streptobacillus moniliformis*)
20) Syphilis (*Treponema pallidum*)
21) Yaws (*Treponema pertenue*)
22) Stage 2-neurological, Cardiac, Arthritis (*Borrelia burgdorferi* [Lyme disease])
23) Relapsing fever (*Borrelia recurrentis*)
24) Weil's disease, Meningitis (Leptospira)
25) Cervicofacial, Abdominal, Thoracic, and other lesions (*Actinomyces israelii*)

PHENOXYMETHYL—PENICILLIN
(Penicillin V)
[acid—stable]
1) Pharyngitis, Scarlet Fever, Otitis Media, Sinusitis, Cellulitis, Erysipelas, Pneumonia, Bacteremia, Toxic shock-like syndrome, and other systemic infections (*Streptococcus pyogenes* [Group A])
2) Pneumonia, Arthritis, Sinusitis, Otitis [Penicillin-Sensitive and Penicillin-Resistant] Endocarditis, Meningitis, other serious infections [Penicillin-sensitive] (*Streptococcus pneumoniae* [pneumococcus])
3) Urinary tract infections (Enterococccus)
4) Urinary tract infection, Bacteremia, Other infections (*Escherichia coli*)+a Penicillinase-inhibitor.
5) Urinary tract and other infections (*Proteus*, other species)+a β-Lactamase inhibitor E. Penicillin
Broad Spectrum
AMOXICILLIN
1) Pharyngitis, Scarlet Fever, Otitis Media, Sinusitis, Cellulitis, Erysipelas, Pneumonia, Bacteremia, Toxic shock-like syndrome and other systemic infections (*Streptococcus pyogenes* [group A])
2) Pneumonia, Arthritis, Sinusitis, Otitis [Penicillin-Sensitive and Penicillin-Resistant] (*Streptococcus pneumoniae* [Pneumococcus])
3) Urinary tract and other infections (*Proteus mirabilis*)

4) Otitis Media, Sinusitis, Pneumonia (*Haemophilus influenzae*)+Clavulanic acid.
5) Wound-infection (animal bites), Abscesses, Bacteremia, Meningitis (*Pasteurella multocida*)+Clavulanic acid
6) Erythema chronica migrans-skin (*Borrelia burgdorferi* [Lyme disease])
7) Pulmonary lesions, Brain abscess, Lesions of other organs (*Nocardia asteroides*)+Clavulanic acid
8) Otitis, Sinusitis, Pneumonia (*Moraxella catarrhalis*)+Clavulanic acid
9) Penicillin-Sensitive gonococcus (*Neisseria gonorrhoeae*)+Probenecid AMPICILLIN
1) Bacteremia, Endocarditis, Meningitis (*Streptococcus agalactiae* [Group B])
2) Urinary tract infection, Endocarditis, or Other serious infections [Bacteremia] (Enterococcus)
3) Otitis, Sinusitis, Pneumonia (*Moraxella catarrhalis*)+Clavulanic acid
4) Penicillin-Sensitive gonococcus (*Neisseria gonorrhoeae*)+Probenecid
5) Meningitis, Bacteremia (*Listeria monocytogenes*)
6) Urinary tract infection, Other infections, Bacteremia (*Escherichia coli*)+an Amihoglycoside
7) Endocarditis, Infected foreign bodies, Bacteremia (*Corynebacterium* species, aerobic and anaerobic [diphtheroids])+Sulbactam
8) Urinary tract and other infections (*Proteus mirabilis*)
9) Typhoid Fever, Paratyphoid Fever, Bacteremia, Acute Gastroenteritis (*Salmonella*)
10) Acute Gastroenteritis (*Shigella*)
11) Epiglottitis, Meningitis (*Haemophilus influenza*)+Sulbactam
12) Bacteremia, Endocarditis, Meningitis (*Campylobacter fetus*)
13) Cervicofacial, Abdominal, Thoracic, an Other lesions (*Actinomyces israelii*)

TICARCILLIN
1) Urinary tract and other infections (*Enterobacter* species)
2) Pneumonia, Bacteremia (*Pseudomonas aeruginosa*) ±an Aminoglycoside
3) Urinary tract infection (*Pseudomonas aeruginosa*)
4) Variety of nosocomial and opportunistic infections (*Serratia*)+an Aminoglycoside PIPERACILLIN
1) Urinary tract and other infections (*Enterobacter* species)
2) Pneumonia, Bacteremia (*Pseudomonas aeruginosa*) ±an Aminoglycoside
3) Urinary tract infection (*Pseudomonas aeruginosa*)
4) Variety of nosocomial and opportunistic infections (*Serratia*)+an Aminoglycoside MEZLOCILLIN
1) Urinary tract and other infections (*Enterobacter* species)
2) Pneumonia, Bacteremia (*Pseudomonas aeruginosa*) ±an Aminoglycoside
3) Urinary tract infection (*Pseudomonas aeruginosa*)
4) Variety of nosocomial and opportunistic infections (*Serratia*)+an Aminoglycoside AZLOCILLIN
1) Urinary tract and Other infections (*Enterobacter* species) Pneumonia, Bacteremia (*Pseudomonas aeruginosa*)±an Aminoglycoside
3) Urinary tract infection (*Pseudomonas aeruginosa*)
4) Variety of nosocomial and opportunistic infections (*Serratia*)+an Amihoglycoside BACAMPICILLIN
TALAMPICILLIN
PIVAMPICILLIN
CARBENICILLIN
APALCILLIN
CARINDACILLIN
PIVMECILLINAM
CARFECILLIN
METAAMPICILLIN
HETACILLIN
TEMOCILLIN F. Penicillin
Penicillinase-Resistant Penicillins (Isoxazoly Penicillins)
OXACILLIN
1) Abscesses, Bacteremia, Endocarditis, Pneumonia, Osteomyelitis, Cellulitis, and Other *Staphylococcus aureus* infections [methicillin-sensitive] (*Staphylococcus aureus*)

CLOXACILLIN
1) Effective against Penicillinase-Producing *Staphylococcus aureus*

DICLOXACILLIN
1) Effective against Penicillinase-Producing *Staphylococcus aureus*

FLUCLOXACILLIN
1) Effective against Penicillinase-Producing *Staphylococcus aureus*

METHICILLIN
1) Effective against Penicillinase-Producing *Staphylococcus aureus*

NAFCILLIN
1) Abscesses, Bacteremia, Endocarditis, Pneumonia, Osteomyelitis, Cellulitis, and Other *Staphylococcus aureus* infections [methicillin-sensitive] (*Staphylococcus aureus*)

G. Cephalosporins
G1. First Generation
CEPHAZOLIN/CEPHRADINE
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (Fusobacterium nucleatum)

12) "Malignant Pustule" Pneumonia (*Bacillus anthracis*)

CEPHALORIDINE
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (Fusobacterium nucleatum)
12) "Malignant Pustule" Pneumonia (Bacillus anthracis)

CEPHRADINE
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (Fusobacterium nucleatum)
12) "Malignant Pustule" Pneumonia (*Bacillus anthracis*)

CEFROXADINE
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (Fusobacterium nucleatum)
12) "Malignant Pustule" Pneumonia (*Bacillus anthracis*)

CEFADROXIL
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (Fusobacterium nucleatum)
12) "Malignant Pustule" Pneumonia (*Bacillus anthracis*)

CETATRIAZINE
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])

6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (*Fusobacterium nucleatum*)
12) "Malignant Pustule" Pneumonia (*Bacillus anthracis*)

CEFALEXIN
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (*Fusobacterium nucleatum*)
12) "Malignant Pustule" Pneumonia (*Bacillus anthracis*)

PIVCEPHALEXIN
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and other systemic infections (*Streptococcus pyogenes* [Group A])
3) Bacteremia, Endocarditis (*Streptococcus agalactiae* [Group B])
4) Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (*Fusobacterium nucleatum*)
12) "Malignant Pustule" Pneumonia (*Bacillus anthracis*)

CEFPROZIL
1) Abscesses, Bacteremia, Endocarditis, Pneumonia, Osteomyelitis, Cellulitis and other *Staphylococcus aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, Toxic shock-like syndrome and, other systemic infections (*Streptococcus pyogenes* [Group A])
3) Bacteremia, Endocarditis (*Streptococcus agalactiae* [Group B])
4) Bacteremia, Bacteremia, Endocarditis, Brain and other abscesses, Sinusitis (*Streptococcus* [anaerobic species])
5) Pneumonia, Arthritis, Sinusitis, Otitis media [Penicillin-Sensitive] (*Streptococcus Pneumoniae* [Pneumococcus])
6) Urinary tract infection, other infections, Bacteremia (*Escherichia coli*)
7) Urinary tract and other infections (*Proteus mirabilis*)
8) Urinary tract infection (*Klebsiella pneumoniae*)
9) Pneumonia (*Klebsiella pneumoniae*)±an Aminoglycoside
10) Wound infection (animal bite), Abscesses, Bacteremia, Meningitis (*Pasteurella Multiocida*)
11) Ulcerative pharyngitis, Lung abscess, Empyema, Genital infections, Gingivitis (*Fusobacterium nucleatum*)
12) "Malignant Pustule" Pneumonia (*Bacillus anthracis*)

Cephalosporins
G2 Second Generation
CEFOXITIN
1) Penicillin-Sensitive and Penicillinase-Producing gonococcus (*Neisseria gonorrhoeae*)
2) Gas gangrene (*Clostridium perfringens* and other species)
3) Variety of nosocomial and opportunistic infections
4) Ulcerative pharyngitis, Lung abscess, Empyema, Genital infections, Gingivitis (*Fusobacterium nucleatum*)

CEFOTETAN
1) Gas gangrene (*Clostridium perfringens* and other species)
2) Variety of nosocomial and opportunistic infections CEFUROXIME AXETIL
1) Otitis media, Sinusitis, Pneumonia (*Haemophilus influenza*)

CEPHAMANDOLE
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFUROXIME
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFONICID
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFORANIDE
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFOTIAM
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFAMYCINS
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside CEFACLOR
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside LORACARBEF
1) Otitis, Sinusitis, Pneumonia (*Moraxella catarrhalis*)
2) Urinary tract and other infections (*Proteus mirabilis*)
3) Urinary tract infection (*Klebsiella Pneumoniae*)
4) Pneumonia (*Klebsiella Pneumoniae*)±an Aminoglycoside Cephalosporins
G3 Third Generation
CEFTRIAXONE
1) Endocarditis, Bacteremia (*Streptococcus* [Viridans Group])
2) Meningitis (*Streptococcus agalactiae* [Group B])
3) Pneumonia, Arthritis, Sinusitis, Otitis [Penicillin-Resistant] (*Streptococcus pneumoniae* [Pneumonococcus])
4) Endocarditis, Meningitis, Other serious infections [Penicillin intermediate-resistant and Penicillin-Sensitive] (*Streptococcus Pneumoniae*)
5) Penicillin-Sensitive and Penicillin Producing gonococcus (*Neisseria gonorrhoeae* [gonococcus])
6) Meningitis (*Neisseria meningitidis* [meningococcus])
7) Typhoid fever, Paratyphoid fever, Bacteremia (*Salmonella*)
8) Epiglottis, Meningitis (*Haemophilus influenzae*)
9) Chancroid (*Haemophilus ducreyi*)
10) Wound infection (animal bite), Abscesses, Bacteremia, Meningitis (*Pasteurella multocida*)
11) Melioidosis (*Pseudomonas pseudomallei*)
12) Bacteremia, Endocarditis, Meningitis (*Campylobacter fetus*)
13) Syphilis (*Treponema pallidum*)
14) Erythema chronica migrans-skin, Stage 2-neurological, Cardiac, Arthritis (*Borrelia burgdorferi* [Lyme disease])
15) Pulmonary lesions, Brain abscess, Lesions of other organs (*Nocardia asteroides*)

CEFOTAXIME
1) Meningitis (*Streptococcus agalactiae* [Group B])
2) Pneumonia, Arthritis, Sinusitis, Otitis [Penicillin-Resistant] (*Streptococcus pneumoniae* [Pneumonococcus])
3) Endocarditis, Meningitis, Other serious infections [Penicillin intermediately-Resistant and Penicillin-Sensitive] (*Streptococcus Pneumoniae*)
4) Endocarditis, Meningitis, Other serious infection [Penicillin G-Resistant] (*Streptococcus pneumoniae*)+Rifampin or +Vancomycin
5) Meningitis (*Neisseria meningitidis* [meningococcus])
6) Epiglottits, Meningitis (*Haemophilus influenzae*)

CEFTIZOXIME
1) Gas gangrene (*Clostridium perfringens* and other species)

CEFIXIME
1) Penicillin-Sensitive and Penicillinase-Producing gonococcus (*Neisseria gonorrhoeae*)

CEFTAZIDIME
1) Urinary tract infection (*Pseudomas aeruginosa*)
2) Pneumonia, Bacteremia *Pseudomonas aeruginosa*+ an Aminoglycoside
3) Melioidosis (*Pseudomonas pseudomallei*)

CEFMENOXIME
1) Otitis, Sinusitis, Pneumonia (*Moraxella Catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFODIZIME
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFDINIR
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFETAMET PIVOXIL
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)

5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFTIBUTEN
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

LATAMOXEF (OXACEPHALOSPORIN)
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFPIRAMIDE
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFSULODIN
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

CEFOPERAZONE
1) Otitis, Sinusitis, Pneumonia (*Moraxella catarrhalis*)
2) Urinary tract and other infections (*Proteus*, other species)
3) Urinary tract and other infections (*Proteus mirabilis*)
4) Urinary tract infection (*Klebsiella pneumoniae*)
5) Pneumonia (*Klebsiella pneumoniae*)±an Aminoglycoside
6) Various nosocomial infections (Acinetobacter)
7) Yersiniosis, Sepsis (*Yersinia enterocolitica*)
8) Variety of nosocomial and opportunistic infections (*Serratia*)

Cephalosporins
G4 Fourth Generation
CEFEPIME
1) Active against many Enterobacteriaceae that are resistant to other cephalosporins
2) Active against *H. influenzae, N. gonorrhoeae* and *N. meningitidis*
3) High activity for streptococci and Methicillin-Sensitive *Staphylococcus aureus*
4) Also active against *P. aeruginosa* and Xanthomonas maltophilia H. Other β-Lactam Antibiotics Carbapenems
IMIPENEM
1) Gas gangrene (*Clostridium perfringens* and other species)
2) Urinary tract and other infections (*Enterobacter* species)
3) Urinary tract and other infections (*Proteus*, other species)
4) Urinary tract infection (*Pseudomonas aeruginosa*)
5) Pneumonia, Bacteremia (*Pseudomonas aeruginosa*)+an Aminoglycoside
6) Pneumonia (*Klebsiella pneumoniae*)
7) Variety of nosocomial and opportunistic infections (*Serratia*)
8) Various nosocomial infections (Acinetobacter)
9) Bacteremia, Endocarditis (*Campylobacter fetus*)
10) Pulmonary lesions, Brain abscess, Lesions of other organs (*Nocardia asteroides*)

MEROPENEM
1) Active against some Imipenem-Resistant *Pseudomonas aeruginosa*
2) Urinary tract infection (*Pseudomonas aeruginosa*)

I. Other β-Lactam Antibiotics
Monobaktams
AZTREONAM
1) Urinary tract infection, Other infections, Bacteremia (*Escherichia coli*)
2) Urinary tract and Other infections (*Proteus*, other species)
3) Urinary tract infection (*Pseudomonas aeruginosa*)
4) Pneumonia, Bacteremia (*Pseudomonas aeruginosa*)+an Aminoglycoside
5) Pneumonia (*Klebsiella pneumoniae*)
6) Variety of nosocomial and opportunistic infections (*Serratia*)

J. Aminoglycoside
Streptomycin
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*) A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)

12) Endocarditis, Infected foreign bodies, Bacteremia (*Corynebacterium* species; aerobic and anaerobic [diptheroids])+Penicillin G
13) Bacteremia, Arthritis, Endocarditis, Abscesses (*Streptobacillus moniliformis*)
14) Pulmonary, Milary, Renal, Meningeal, and other tuberculous infections (*Mycobacterium tuberculosis*)+Rifampin or Ethambutol
15) Yaws (*Treponema pertenue*)
16) Plague (*Yersinia pestis*)±Tetracycline
17) Tularemia (Francisella tularensis)
18) Glanders (*Pseudomonas mallei*)+a Tetracycline or +Chloramphenicol
19) Occasionally administrate for tuberculosis (*Mycobacterium tuberculosis*)

GENTAMICIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G
13) Endocarditis or other serious infection [bacteremia] (Enterococcus)+Penicillin G or Ampicillin; +Vancomycin
14) Meningitis, Bacteremia (*Listeria monocytogenes*)+Ampicillin or Penicillin G
15) Brucellosis (*Brucella*)+Doxycycline
16) Tularemia (Francisella tularensis)
17) Bacteremia, Endocarditis (*Campylobacter fetus*)

TOBRAMYCIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G AMICACIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G
13) Disseminated disease in AIDS (*Mycobacterium avium*—intracellulare)
14) Pulmonary lesions, Brain abscess, Lesions of the other organs NETILMICIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G
13) Effective against certain gentamicin-resistant pathogens, except enterococci KANAMYCIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)

6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G
13) Orally for the prophylactic use as adjunctive therapy in cases of hepatic coma NEOMYCIN
1) Urinary tract infection, other infections, Bacteremia. (*Escherichia coli*)±Ampicillin
2) Urinary tract infection and other infections (*Enterobacter* species)
3) Urinary tract infection and other infections (*Proteus mirabilis*)
4) Urinary tract infection and other infections (*Proteus*, other species)
5) Urinary tract infection (*Pseudomonas aeruginosa*)
6) Pneumonia, Bacteremia (*Pseudomonas aeruginosa*)+A broad-spectrum Penicillin; +Ciprofloxacin; +Ceftazidime; +Aztreonam; +Imipenem
7) Urinary tract infection (*Klebsiella pneumoniae*)
8) Pneumonia (*Klebsiella pneumoniae*)+Mezlocillin or Piperacillin
9) Variety of nosocomial and opportunistic infections (*Serratia*)+A broad-spectrum Penicillin
10) Various nosocomial infections (Acinetobacter)
11) Sepsis (*Yersinia enterocolitica*)
12) Endocarditis, Infected foreign bodies, Bacteremia (*Corynebacterium* species; aerobic and anaerobic [diptheroids])+Penicillin G
13) For bladder irrigation+Polymyxin B
14) Variety of infections of the skin and mucous membranes caused by microorganisms susceptible to the drug. These include infections associated with burns, wounds, ulcers, and infection dermatoses.

K. Tetracycline
TETRACYCLINE
1) Sinusitis (*Moraxella catarrhalis*)
2) Plague (*Yersinia pestis*)±Streptomycin
3) Glanders (*Pseudomonas mallei*)+Streptomycin
4) Stage 2-Neurological, cardiac, arthritis (*Borrelia burgdorferi* [Lyme disease])
CHLORTETRACYCLINE
OXYTETRACYCLINE
DOXYCYCLINE
1) Erysipeloid (*Erysipelothrix rhusiopathiae*)
2) Gas gangrene (Clostridium perfringens & other species)
3) Tetanus (*Clostridium tetani*)
4) Urinary tract infection (*Escherichia coli*)
5) Brucellosis (*Brucella*)+Gentamicin or Rifampin
6) Chancriod (*Haemophilus ducreyi*)
7) Plague (*Yersinia pestis*)
8) Wound infection-animal bite (*Pasteurella multocida*)
9) Cholera (*Vibrio cholerae*)
10) Lung abscess, empyema (Fusobacterium nucleatum)
11) Arthritis (*Streptobacillus moniliformis*)
12) Syphilis (*Treponema pallidum*)
13) Yaws (*Treponema pertenue*)
14) Erythema chronica migrans-skin (*Borrelia burgdorferi*[Lyme disease])
15) Relapsing fever (*Borrelia recurrentis*)
16) Weil's disease and meningitis (Leptospira)
17) Cervicofacial, abdominal, thoracic, and other lesions (*Actinomyces israelii*)
18) Non-specific urethritis (*Ureaplasma urealyticum*)
19) "Atypical pneumonia" (*Mycoplasma pneumoniae*)
20) Typhus fever, Murine typhus, Brill's disease, Rocky Mountain spotted fever, Q fever, and Rickettsialpox (*Rickettsia*)
21) Psittacosis (*Chlamydia psittaci*)
22) Lymphogranuloma venereum, Trachoma, Inclusion conjunctivitis (blennorrhea), Non-specific urethritis, Cervicitis (*Chlamydia trachomatis*)
23) Pneumonia (*Chlamydia pneumoniae*)

MINOCYCLINE
DEMECLOCYCLINE
METHACYCLINE

L. Chloramphenicol
CHLORAMPHENICOL
1) Meningitis (*Streptococcus agalactiae* [Group B])
2) Bacteremia, Endocarditis, Brain and other abscesses, and Sinusitis (*Streptococcus*[anaerobic species])
3) Pneumonia, Arthritis, Sinusitis, Otitis, Endocarditis, Meningitis, Other serious infections (*Streptococcus pneumoniae* [pneumonococcus]).
4) Meningitis (*Neisseria meningitidis* [meningococcus])
5) "Malignant pustule", Pneumonia (*Bacillus anthracis*)
6) Bacteremia (*Listeria monocytogenes*)
7) Erysipeloid (*Erysipelothrix rhusiophathiae*)
8) Gas gangrene (*Clostridium perfringens* and other species)
9) Typhoid fever, Paratyphoid fever, Bacteremia (*Salmonella*)
10) Epiglottitis, Meningitis (*Haemophilus influenza*)
11) Brucellosis (*Brucella*)
12) Plague (*Yersinia pestis*)
13) Sepsis (*Yersinia enterocolitica*)
14) Tularemia (Francisella tularensis)
15) Cholera (*Vibrio cholerae*)
16) Glanders (*Pseudomonas mallei*)+Streptomycin
17) Melioidosis (*Pseudomonas pseudomallei*)
18) Meningitis (*Campylobacter fetus*)
19) Ulcerative pharyngitis, Lung abscess and Empyema, Genital infections, Gingivitis (Fusobacterium nucleatum)
20) Bacteremia, Arthritis, Endocarditis, Abscesses (*Streptobacillus moniliformis*)
21) Typhus fever, Murine typhus, Brill's disease, Rocky mountain spotted fever, Q fever, Rickettsialpox (*Rickettsia*)
22) Psittacosis [ornithosis] (*Chlamydia psittaci*)
THIAMPHENICOL
AZIDAMPHENICOL M. Erythromycin and Others
Macrolides:
ERYTHROMYCIN
1) Abscesses, Bacteremia, Endocarditis, Pneumonia Osteomyelitis, Cellulitis and other *Staph. aureus* infections [Methicillin-Sensitive] (*Staphylococcus aureus*)
2) Pharyngitis, Scarlet fever, Otitis media, Sinusitis, Cellulitis, Erysipelas, Pneumonia, Bacteremia, toxic shock-like syndrome, and other systemic infections (*Streptococcus pyogenes* [Group A])
3) Bacteremia, Endocarditis, Brain and other abscesses, Sinusitis (*Streptococcus* [anaerobic species])
4) Penicillin-Sensitive gonococcus (*Neisseria gonorrhoeae*)
5) "Malignant pustule", Pneumonia (*Bacillus anthracis*)
6) Pharyngitis, Laryngotracheitis, Pneumonia, and other local lesions, Carrier state (*Corynebacterium diptheriae*)
7) Bacteremia (*Listeria monocytogenes*)
8) Chancroid (*Haemophilus ducreyi*)
9) Enteritis (*Campylobacter jejuni*)
10) Ulcerative pharyngitis, Lung abscess, Empyema, Genital infections, Gingivitis (Fusobacterium nucleatum)
11) Bacteremia, Arthritis, Endocarditis, Abscesses (*Streptobacillus moniliformis*)
12) Legionnaires' disease (*Legionella pneumophila*) ±rifampin
13) Relapsing fever (*Borrelia recurrentis*)
14) Cervicofacial, Abdominal, Thoracic and other lesions (*Actinomyces israelii*).
15) Non-specific Urethritis (*Ureaplasma Urealyticum*)
16) "Atypical pneumonia" (*Mycoplasma pneumoniae*)
17) Lymphogranuloma venereum, Trachoma, Inclusion conjunctivitis [blennorrhea], Non-specific urethritis, Cervicitis (*Chlamydia trachomatis*)
18) Pneumonia (*Chlamydia pneumoniae*)
19) Erysipeloid (*Erysipelothrix rhusiopathiae*)
20) *Bordetella pertussis* disease and for post-exposure prophylaxis of all household member and other close contacts.
21) Tetanus in patients who are allergic to penicillin (*Clostridium tetani*)

CLARITHROMYCIN
1) Legionnaires' disease (*Legionella pneumophila*)
2) "Atypical pneumonia" (*Mycoplasma pneumoniae*)
3) Pneumonia (*Chlamydia pneumoniae*)
4) Enteritis (*Campylobacter jejuni*)
5) Disseminated disease in AIDS (*Mycobacterium avium*—intracellulare)+Ethambutol; ±Clofazimine; ±Ciprofloxacin
6) Erythema chronica migrans-skin (*Borrelia burgdorferi* [Lyme disease])
7) Modest activity against *H. influenzae* and *N. gonorrhoeae*
8) Good activity against *M. catarrhalis*
9) Enhanced activity against some protozoa (e.g., Toxoplasma gondii, Cryptoporidium and Plasmodium spp.
10) Regimens for the treatment of peptic ulcers related to *H. pylori* infection
11) Lepromatous leprosy (*Mycobacterium leprae*)+minocycline AZITHROMYCIN
1) Otitis media, Sinusitis, Pneumonia (*Haemophilus influenzae*)
2) Enteritis (*Campylobacter jejuni*)
3) Legionnaires' disease (*Legionella pneumophila*)
4) Erythema chronica migrans-skin (*Borrelia burgdorferi* [Lyme disease])
5) "Atypical pneumonia" (*Mycoplasma pneumoniae*)
6) Lymphogranuloma venereum, Trachoma, Inclusion conjunctivitis [blennorrhea], Non-specific urethritis, Cervicitis (*Chlamydia trachomatis*)
7) Pneumonia (*Chlamydia pneumoniae*)
8) Less active against *Streptococcus* spp. And Enterococci
9) Active against *M. catarrhals, Pasteurella multocida*, Fusobacterium spp., *N. gonorrhoeae*
10) Enhanced activity against *Mycobacterium avium*-intracellulare, as well as against protozoa (e.g. Toxoplasma gondii, Crytosporidium and Plasmodium spp.
11) Toxoplasmosis encephalitis and diarrhoea due to *Cryptosporidium*

ROXITHROMYCIN

N. Lincomycin
CLINDAMYCIN
1) Abscesses, Bacteremia, Endocarditis, Pneumonia, Osteomyelitis, Cellulitis and other *Staphylococcus aureus* infections [Methicillin-Sensitive] (*Staphylococcus aureus*).
2) Pharyngitis, Scarlet fever, Otitis media, Sinusitis, Cellulitis, Erysipelas, Pneumonia, Bacteremia, Toxic shock-like syndrome, and other systemic infections (*Streptococcus pyogenes* [Group A])
3) Bacteremia, Endocarditis, Brain and other abscesses, Sinusitis (*Streptococcus* [anaerobic species])
4) Pneumonia, Arthritis, Sinusitis, Otitis [Penicillin-Sensitive and Penicillin-Resistant](*Streptococcus pneumoniae*)
5) Pharyngitis, Laryngotracheitis, Pneumonia, Other local lesions (*Corynebacterium diphteriae*)
6) Gas gangrene (*Clostridium perfringens* and other species)
7) Tetanus (*Clostridium tetani*)
8) Enteritis (*Campylobacter jejuni*)
9) Ulcerative pharyngitis, Lung abscess, Empyema, Genital infections, Gingivitis
10) Pneumonia in impaired host [Mild or moderate disease and moderately severe or severe disease] (Pneumocystis carinii)+Primaquin
11) Treatment of infections with anaerobes, especially those due to *B. fragilis*
12) Intra-abdominal or pelvic abscesses and peritonitis+ an Aminoglycoside or +Penicillin or +Cephalothin
13) Topically or orally for acne vulgaris and for bacterial vagionosis SPECTINOMYCIN
1) Penicillin-Sensitive and Penicillinase-Producing gonococcus (*Neisseria gonorrhoeae*)
2) In pregnancy when patients are intolerant to β-Lactams and when quinolones are contraindicated
3) Recommended as an alternative regimen in patients who are intolerant or allergic to β-Lactam antibiotics and quinolones POLYMYXIN B (Polymyxin B Sulfate)
1) Available for ophthalmic, otic and topical use in combination with a variety of other compounds.
2) Infections of the skin, mucous membranes, eye, and ear due to polymyxin B-sensitive microorganisms
3) External otitis, frequently due to pseudomonas
4) Infection of corneal ulcers (*Pseudomonas aeruginosa*)
5) Pneumonia (Pseudomonas)

COLISTIN (Colisten Sulfate)
1) Diarrhoea caused by bacteria susceptible to the drug in infants and children RAMOPLANIN (glycopeptide)
1) Treatment of acne and skin infections, and to reduce nasal carriage of staphylococci Active against *Bacteroides* spp.

TEICOPLANIN (glycopeptide)
  1) Osteomyelitis, Endocarditis caused by Methicillin-Resistant and Methicillin-Susceptible Staphylococci, Streptococci and Enterococci
  2) Bacteremia, Endocarditis [methicillin susceptible] (*Staphylococcus aureus*)+an Aminoglycoside [gentamycin]
  3) Enterococcal endocarditis+Gentamicin
  4) Endocarditis+Vancomycin
BACITRACIN
  1) Infected eczema, Infected dermal ulcers
  2) Suppurative conjunctivitis and infected corneal ulcer when they are cause by susceptible bacteria
  3) Eradication of nasal carriage of Staphylococci
  4) Antibiotic-associated diarrhoea (*Clostridium difficile*)
RP 59500
  1) Is a good inducer of the methylase enzyme that mediates MLS resistance
  2) Are synergistic and therefore, erythromycin-resistant organisms frequently are susceptible to RP 59500 in vitro
GLYCYLCYCLINES (Tetracycline Antibiotic derivatives)
  1) They inhibit some tetracycline-resistant organisms
  2) Also appear to be active against multiply drug-resistant strains of Staphylococci, pneumacocci and vancomycin-resistant enterococci
Glycopeptide and Other:
VANCOMYCIN
  1) Abscesses, Bacteremia, Endocarditis, Pneumonia, Osteomyelitis, Cellulitis and other *Staphylococcus aureus* infections [Methicillin-Sensitive and Methicillin Resistant] (*Staphylococcus aureus*)
  2) Pharyngitis, Scarlet fever, Otitis media, Sinusitis, Cellulitis, Erysipelas, Pneumonia, Bacteremia, Toxic shock-like syndrome, and other systemic infections (*Streptococcus pyogenes* [Group A])
  3) Endocarditis, Bacteremia (*Streptococcus* [Viridans Group])
  4) Bacteremia, Endocarditis (*Streptococcus agalactiae* [Group B])
  5) Pneumonia, Arthritis, Sinusitis, Otitis [Penicillin-Resistant] (*Streptococcus pneumoniae*).
  6) Endocarditis, Meningitis, Other serious infections [Penicillin-intermediately Resistant] (*Streptococcus pneumoniae*)+Rifampin
  7) Endocarditis, Meningitis, Other serious infections [Penicillin G-Resistant] (*Streptococcus pneumoniae*)+Rifampin or +Cefotaxime
  8) Endocarditis or other serious infection [bacteremia] (Enterococcus)+Gentamincin
  9) Urinary tract infection (Enterococcus)
  10) Endocarditis, Infected foreign bodies, Bacteremia (*Corynebacterium* species, aerobic and anaerobic [diptheroids])
  11) Tetanus (*Clostridium tetani*)
  12) Antibiotic-associated colitis (*Clostridium difficile*)
  13) Meningitis (Flavobacterium meningosepticum)
  14) Pseudomembranous colitis
  15) Staphylococcal infections in patients who are allergic to penicillins and cephalosporins
O. Drugs Used in the Treatment of Tuberculosis, *Mycobacterium avium* Complex, and Leprosy
  AMIKACIN,
  AMINOSALICYCLIC ACID
  AZITHROMYCIN
  CAPREOMYCIN
  CEFOXITIN
  CIPOFLOXACIN
  CLARITHROMYCIN
  CLOFAZIMINE
  DAPSONE
  DOXYCYCLINE
  ETHAMBUTOL
  ETHIONAMIDE
  IMIPENEM
  ISONIAZID
  KANAMYCIN
  MINOCYCLINE
  OFLOXACIN
  OFLOXACIN
  PYRAZINAMIDE
  RIAMPIN
  RIFABUTIN
  RIFAMPIN
  STREPTOMYCIN
  SULFONAMIDE
  TRIMETHOPRIM-SULFAMETHOXAZOLE,
P. Other Treatments
  RIFAMPIN
    1) Abscesses, Bacteremia, Endocarditis, Pneumonia, Osteomyelitis, Cellulitis, Other [Methicillin-Sensitive Methicillin-Resistant] (*Staphylococcus aureus*)+Ciprofloxacin or [+Trimethoprim-sulfumethoxazole when methicillin-resistant]
    2) Endocarditis, Meningitis, Other serious infection [Penicillin-Intermediately resistant] (*Streptococcus pneumonia* (pneumonococcus))+Vancomycin
    3) Endocarditis, Meningitis, Other serious infection [Penicillin G-resistant] (*Streptococcus pneumoniae* (pneumonococcus))+Cefotaxime or +Vancomycin
    4) Carrier state (post-treatment) (*Neisseria meningitidis* (meningoccoccus))
    5) Pharyngitis, Laryngotracheitis, Pneumonia, Other local lesions (*Corynebacterium diphtheriae*)
    6) Endocarditis, Infected foreign bodies, Bacteremia (*Corynebacterium* species, aerobic and anaerobic (diphtheroids))+Penicillin G
    7) Brucellosis (*Brucella*)+Doxycycline or +Trimethoprim
    8) Meningitis (Flavobacterium meningosepticum)
    9) Legionnaires' disease (*Legionella pneumophila*)+Erythromycin
Q. Anti-Fungal Agents
  AMPHOTERICIN B
  AMPHOTERICIN B
  AMPHOTERICIN B
  AMPHOTERICIN B
  AMPHOTERICIN B
  AMPHOTERICIN B
  AMPHOTERICIN B
  AMPHOTERICIN B,
  BUTOCONAZOLE
  CICLOPIROX
  CICLOPIROX
  CLOTRIMAZOLE
  CLOTRIMAZOLE
  CUTANEOUS
  ECONAZOLE
  ECONAZOLE
  EXTRACUTANEOUS
  FLUCONAZOLE
  FLUCONAZOLE
  FLUCONAZOLE FLUCONAZOLE
FLUCONAZOLE,
FLUCYTOSINE
GRISEOFULVIN
HALOPROGIN
INTRATHECAL
IODIDE, ITRACONAZOLE
ITRACONAZOLE
ITRACONAZOLE
ITRACONAZOLE,
ITRACONAZOLE,
ITRACONAZOLE,
IV MICONAZOLE
KETOCONAZOLE
KETO-CONAZOLE
KETO-CONAZOLE
KETO-CONAZOLE
KETOCONAZOLE,
MICONAZOLE
MICONAZOLE
MICONAZOLE NYSTATIN
NAFTIFINE
NYSTATIN
NYSTATIN
SPOROTRICHOSIS
SYSTEMIC
TERBINAFINE
TERBINAFINE
TERCONAZOLE
TIOCONAZOLE
TOPICAL CLOTRIMAZOLE
UNDECYLENATE R. Other Treatments
Polieen Antibiotics
AMPHOTERICIN B
1) Deep infection (*Candida* species)±Flucytosine
2) Disseminated (non-meningeal), Meningitis (Coccidioides immitis)
3) Chronic Pulmonary disease, Disseminated (Histoplasma capsulatum)
4) All the Blastomyces brasiliensis infections
5) All the paracocidioides brasiliensis infections followed up by a sulfonamide
6) Extracutaneous (Sporothrix schenckii)
7) Invasive (*Aspergillus* species)
8) All the infections of the mucormycosis Agents
9) Pulmonary (Cryptococcus neoformans)
10) Meningitis (Cryptococcus neoformans)±Flucytosine NYSTATIN
1) Cutaneous or vaginal thrush, oral thrush (Candida species)

FLUCYTOSINE
1) Deep infections (*Candida* species)+Amphotericin B
2) Meningitis (Cryptococcus neoformans)+Amphotericin B POVIDONE IODINE
Povidone-iodine is an iodophore which is used as a disinfectant and antiseptic mainly for the treatment of contaminated wounds and pre-operative preparation of the skin and mucous membranes as well as for the disinfection of equipment.

S. Imidazoles and Triazoles
KETOCONAZOLE
1) Cutaneous or vaginal thrush, Oral thrush, (*Candida* species)
2) Chronic pulmonary disease (Histoplasma capsulatum)
3) All Blastomyces dermatitidis infections.
4) All Paracoccidioides brasiliensis infections ITRACONAZOLE
1) Cutaneous or vaginal thrush, Oral thrush (Candida species)
2) Disseminated (non-meningeal), Meningitis (Coccidioides immitis)
3) Disseminated (Histoplasma capsulatum)
4) Cutaneous, Extracutaneous (Sporothrix schenckii)
5) Invasive (*Aspergillus* species)
6) Chronic pulmonary disease (Histoplasma capsulatum)
7) All paracoccidioides brasiliensis infections
8) All Blastomyces dermatitidis infections FLUXONAZOLE
1) Cutaneous or vaginal thrush, Oral thrush, Deep infection (*Candida* Species)
2) Disseminated (non-meningeal), Meningitis (Coccidioides immitis)
3) Chronic pulmonary disease (Histoplasma capsulatum)
4) Meningitis (Cryptococcus neoformans)

CLOTRIMAZOLE
1) Oral thrush (*Candida* Species)

GRISEOFULVIN
1) Mycotic disease of the skin, hair and nails due to Microsporum, Trichophyton or Epidermophyton
2) Tinea capitis (M. canis, M. audouini; T. schoenleinii and T. verrucosum)
3) "Ringworm" of the glabrous skin, Tinea cruris and tinea corporis (M. canis, T. rubrum, T. verrucosum and E. floccosum)
4) Tinea of the hands (T. rubrum, T. mentagraphytes)
5) Tinea of the beard (Trichopyton species)
6) "Athlete's foot" or epidermophytosis involving the skin and nails (T. mentagraphytes and the hyperkeratotic type to T. rubrum).

T. Topical Anti-Fungal Agents
Imidazoles and Triazoles for Topical Use
CLOTRIMAZOLE
1) Dermatophyte infections, Cutaneous candidiasis, Vulvovaginal candidiasis ECONAZOLE
MICONAZOLE
1) Tinea pedis, Tinea cruris, Tinea versicolor
2) Vulvovaginal candidiasis
3) Some vaginal infections caused by *Candida glabrata*

TERCONAZOLE
1) Vaginal Candidiasis

BUTOCONAZOLE
1) Vaginal Candidiasis

TIOCONAZOLE
1) *Candida* Vulvovaginitis

OXICONAZOLE
1) Infections caused by the common pathogenic dermatophytes

SULCONAZOLE
1) Infections caused by the common pathogenic dermatophytes

U. Other Anti-Fungal Agents for Topical Use
CICLOPIROX OLAMINE
1) Cutaneous candidiasis, Tinea corporis, Tinea cruris, Tinea pedis, Tinea versicolor
2) Dermatomycoses and candidal infections HALOPROGIN
 1) Tinea pedis, Tinea cruris, Tinea corporis, Tinea manuum and Tinea versicolor
TOLNAFTATE
 1) Tinea pedis
NAFTIFINE
 1) Treatment of Tinea cruris and Tinea corporis
 2) Cutaneous candidiasis and Tinea versicolor
TERBINAFINE
 1) Tinea corporis, Tinea cruris, Tinea pedis
 2) Cutaneous candidiasis and Tinea versicolor
 3) Treatment of ringworm and in some cases of onychomycosis V. Miscellaneous Anti-Fungal Agents
UNDECYLENIC ACID
 1) Treatment of various dermatomycoses, especially Tinea pedis
 2) Treatment of diaper rash, Tinea cruris and other minor dermatologic condition's
BENZOIC ACID AND SALICYLIC ACID
 1) Treatment of Tinea pedis and sometimes used to treat Tinea capitis
PROPIONIC ACID AND CAPRYLIC ACID
 1) Treatment of the dermatomycoses
POTASSIUM IODIDE
 1) Cutaneous (Sporothrix schenckii)

W. Anti-Fungal Agents for Ophthalmic Use
NATAMYCIN
 Fungal blepharitis, conjunctivitis, keratitis
IMIDAZOLES CLOTRIMAZOLE
 Fungal keratitis
ECONAZOLE
 Fungal keratitis
FLUCONAZOLE
 Fungal keratitis
KETOCONAZOLE
 Fungal keratitis
MICONAZOLE
 Fungal keratitis, endophthalmitis
PYRIMIDINES
FLUCYTOSINE
 Fungal keratitis
POLYENES AMPHOTERICIN B
 Fungal keratitis, endophthalmitis X. Anti-Viral Agents
Anti-Herpesvirus Agents:
ACYCLOVIR
 1) Genital disease, Keratoconjunctivitis, Encephalitis, Neonatal HSV, Mucocutaneous HSV in immuno-compromised host (Herpes simplex virus)
 2) Herpes zoster or varicella in immuno-compromised host, pregnancy, Varicella or herpes zoster in normal host (Varicella zoster virus)
VALACYCLOVIR
 1) Genital herpes or localised herpes zoster
FAMCICLOVIR
 1) Varicella or herpes zoster in normal host (Varicella zoster virus)
PENCICLOVIR
 1) It is inhibitory for hepatitis B virus
FOSCARNET
 1) Retinitis in patients with AIDS (Cytomegalovirus)
 2) Mucocutaneous HSV in immuno-compromised host (Herpes simplex virus)
 3) Herpes zoster or varicella in immuno-compromised host, pregnancy (Varicella zoster virus)
GANCICLOVIR
 1) Retinitis in patients with AIDS (Cytomegalovirus)
IDOXURIDINE
 1) Keratoconjunctivitis (Herpes simplex virus)
SORIVUDINE
 1) Herpes zoster in HIV-infected adults
TRIFLURIDINE
 1) Keratoconjunctivitis (Herpes simplex virus)
VIDARABINE
 1) Encephalitis, neonatal herpes (Herpes simplex virus)
 2) Zoster or varicella in immuno-compromised patients Y. Anti-Retroviral Agents
ZIDOVUDINE
 1) AIDS, HIV antibody positive and CD4 count less than 500/mm$^3$ (Human immuno-deficiency virus)
DIDANOSINE
 1) Advanced HIV infections in adults and children over 6 months
STAVUDINE
 1) AIDS, HIV antibody positive and CD4 count less than 400/mm$^3$ (Human immuno-deficiency virus)
ZALCITABINE
 1) AIDS
 2) HIV infection and CD4 count less than 300/mm$^3$ Z. Other Anti-Viral Agents
AMANTADINE
 1) Influenza (Influenza A)
RIMANTADINE
 1) Influenza (Influenza A)
INTERFERONS ALFA
 1) Genital papilloma (Human papilloma virus)
RIBAVIRIN
 1) Pneumonia and bronchiolitis infancy (Respiratory syncytial virus)

AA. Newer Agents Under Clinical Development
LAMIVUDINE
PROTEASE INHIBITORS
ACYCLIC NUCLEOSIDE PHOSPHONATES AB. Anti-Viral Agents for Ophthalmic Use
IDOXURIDINE (HERPLEX)
 1) Herpes simplex keratitis
TRIFLURIDINE (VIROPTIC)
 1) Herpes simplex keratitis
VIDARABINE (VIRA-A)
 1) Herpes simplex keratitis
 2) Herpes simplex conjunctivitis
ACYCLOVIR (ZOVIRAX)
 1) Herpes zoster ophthalmicus
 2) Herpes simplex keratitis
FOSCARNET (FOSCAVIR)
 1) Cytomegaloviris retinitis
GANCICLOVIR (CYTOVENE)
 1) Cytomegaloviris retinitis AC. Topical Antibacterial Agents Commercially Available for Ophthalmic Use
BACITRACIN ZINC (AK-TRACIN)
 1) Conjunctivitis, blepharitis
CHLORAMPHENICOL (AK-CHLOR, CHLOROMYCETIN, CHLOROPTIC, OCU-CHLOR)
 1) Conjunctivitis, keratitis
CHLORTETRACYCLINE HYDROCHLORIDE (AUREOMYCIN)
 1) Conjunctivitis, blepharitis
CIPROFLOXACIN HYDROCHLORIDE (CILOXAN)
 1) Conjunctivitis, keratitis
ERYTHROMYCIN (AK-MYCIN, ILOTYCIN)
 1) Blepharitis, conjunctivitis GENTAMICIN SULFATE (GARAMYCIN, GENOTIC, GENT-AK, GENTACIDIN)
   1) Conjunctivitis, blepharitis, keratitis
NORFLOXACIN(CHIBROXIN)
   1) Conjunctivitis
SULFACETAMIDE SODIUM
   (AK-SULF, BLEPH-10, CETAMIDE, SULF-10, ISOPTO CETAMIDE, OPHTHACET, SULAMYD SODIUM)
   1) Conjunctivitis, blepharitis, keratitis
SULFISOXAZOLE DIOLAMINE (GANTRISIN)
   1) Conjunctivitis, blepharitis, keratitis
POLYMYXIN B COMBINATIONS
   1) Conjunctivitis, blepharitis, keratitis
TETRACYCLINE HYDROCHLORIDE (ACHROMYCIN)
   1) Conjunctivitis, blepharitis
TOBRAMYCIN SULFATE (TOBREX)
   1) Conjunctivitis, blepharitis, keratitis (ii) CPNS Agents According to the present invention there is further provided a method of enhancing the action of a pharmaceutical agent selected from the group consisting of the CPNS agents selected from the group of compounds acting on the central or peripheral nervous system, but excluding coal tar solution and H1-antagonist antihistamines and also excluding anti-inflammatory, analgesic and antipyretic agents, comprising the step of formulating the agent with an administration medium which is characterised in that it comprises a solution of nitrous oxide gas in a pharmaceutically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils such as castor oil with ethylene oxide.

According to a further aspect of the present invention there is provided a pharmaceutical preparation comprising a pharmaceutical agent which is a CPNS agent selected from the group of compounds acting on the central or peripheral nervous system, but excluding coal tar solution and H1-antagonist antihistamines and also excluding anti-inflammatory, analgesic and antipyretic agents, comprising the step of formulating the agent with an administration medium which is characterised in that it comprises a solution of nitrous oxide gas in a pharmaceutically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils such as castor oil with ethylene oxide.

The administration medium may further include eicosapentaenoic acid [C20:5ω3] and/or decosahexaenoic acid [C22:6ω3] as additional long chain fatty acids.

The carrier solvent for the nitrous oxide gas may be water or any of the pharmaceutically acceptable alcohols, ethers, oils or polymers such as, for example a polyethylene glycol. The oil may be organic or mineral oil. The organic oil may be an essential oil based on long chain fatty acids having between 14 and 22 carbon atoms in the fatty acid. The oil may also be of either natural or synthetic origin and, if of natural origin, it may be either plant oil or animal oil. As plant oils those rich in gamma linolenic acid [GLA] are preferred and as animal oil dairy cream may be used.

In the preferred form of the invention the solution is an aqueous solution saturated with nitrous oxide.

The water is preferably de-ionised water and free of microbes.

When the CPNS agent to be enhanced by means of the nitrous oxide is in a liquid formulation, such formulation may incorporate as part of the administration medium water or acceptable other liquid solvent into which the nitrous oxide and fatty acid or ester thereof had been dissolved or suspended or emulsified along with the CPNS agent to be enhanced by being formulated therewith. When the formulation containing the CPNS agent to be enhanced by means of the nitrous oxide is to be in a liquid (including an encapsulated liquid) presentation for oral administration or in a nasal or bronchial or pulmonary spray or in the form of an injectable formulation, such formulation may incorporate, as part of the administration medium, water or acceptable other liquid into which the nitrous oxide is dissolved and in which the fatty acid or ester thereof is either dissolved or suspended or emulsified along with the CPNS agent to be enhanced by being formulated therewith.

Likewise, where the CPNS agent is to be administered to the patient by being applied as a topical, buccal or vaginal cream or ointment, or as a cutaneous patch, or in the form of micro-depots, or as an intravenous, intramuscular or subcutaneous injection, or as a suppository, the formulation used in making up such cream, ointment, patch, depots or injectable formulation or suppository may incorporate, along with the CPNS agent to be enhanced, a quantity of water or other liquid containing, and preferably saturated with, nitrous oxide, the long chain fatty acid or ester thereof and a CPNS agent conjugated therewith, and, further, such additional excipients and carriers as are conventionally used in the pharmaceutical trade in making up such dosage forms.

The carrier solvent for the nitrous oxide gas may thus be essentially non-aqueous and composed of the at least one fatty acid or ester thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils with ethylene oxide, required to be part of the formulation.

The essential fatty acid, or ester thereof, component of the composition preferably comprises a mixture of esters of the fatty acids listed above. Thus, in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:
$<C_{16}$: 0
$C_{16.0}$: 8.3%
$C_{18.0}$: 3.5%

$C_{18:1}$: 21.7%
$C_{18:2}$: 34.8%
$C_{18:4}$: 28.0%
$>C_{18}$: 1.6%
unknown: 2.1%

It is further preferred to add to the formulation the long chain fatty acids known as eicosapentaenoic acid [C20:5ω3] and decosahexaenoic acid [C22:6ω3]. Such a product combination is available from Roche Lipid Technology under the trade name "Ropufa '30' n-3 oil".

It has been found by microscopic studies that the formulation of active agents with a medium as herein described gives rise to the formation of minute, generally spherical bodies, in which the active ingredient is contained in a stable form and from which it is delivered at the site of action.

The CPNS agent utilised in the method or formulation according to the present invention may comprise any one or more of the vast spectrum of CPNS agents as herein defined.

From amongst the CPNS agents falling within the scope of the definition set out above this invention is particularly concerned with the following sub-classes of compounds:

Central nervous system stimulants including central analeptics, psycho analeptics (antidepressants), respiratory stimulants, hallucinogenic medicines;

Central nervous system depressants including anaesthetics, sedatives, hypnotics, barbiturates, non-barbiturates, anticonvulsants, (including anti-epileptics), tranquillisers (including phenothiazines and their derivatives, rauwolfia, diphenylmethane and its derivatives, alkyl diols and their derivatives), centrally acting muscle relaxants;

Local anaesthetics;

Medicines affecting autonomic functions including adrenomimetics (sympathomimetics), adrenolytics (sympatholytics), cholinomimetics (cholinergics), cholinolytics (anticholinergics) (including anti-Parkinsonism preparations), Ganglion blockers, anti-emetics and anti-vertigo preparations, decongestants, -hydroxytryptamine (serotonin) and serotonin antagonists, and anti-Alzheimers agents.

The invention has not yet been demonstrated by empirical work to be applicable to all the agents or classes of agents referred to herein. However in respect of such CPNS agents which have already been formulated with the aforementioned administration medium of the invention, and evaluated by different methods for the anticipated enhancement of action, no negative result has as yet been observed despite the chemical diversity of the CPNS agents which has been investigated. The applicant thus confidently expects on the basis of these preliminary observations that the invention will find general application across the entire spectrum of CPNS agents embraced by these terms as herein defined and of which some examples are set out herein.

It is part of the applicant's present postulations by which it seeks to find an understanding of the invention and to which it does not wish to be bound at this stage, that while the administration medium of the present invention serves to transport the CPNS agent formulated therewith most efficiently through the human or animal body, that medium also plays an important role in transferring, by an as yet unexplained mechanism, the CPNS agent through the membranes of and into the cells thereby to cause an effective CPNS intercellular and/or intracellular concentration of the agent rapidly to be achieved, and to be maintained.

It is in this respect that the applicant believes that the present invention will find general application despite the vast list of agents mentioned below. The following list sets out examples of some of the specific CPNS agents with which this invention is concerned and which will now be identified with reference to the broad classes in which they fall and, in some cases, also with reference the respective indications for which such agents are indicated The CPNS agents with which the invention is particularly concerned are
  a. the Central Nervous System Stimulants consisting of
    i. the following Central Analeptics:
      Amphetamine, Dextroamphetamine, Methamphetamine, Methylphenidate, Caffeine, Caffeine citrated, Caffeine and Sodium Benzoate, Clomipramine, Desipramine, Ephedrine, Imipramine, Pemoline, Protryptiline,
    ii. the following Psycho Analeptics (antidepressants):
      1. the Tricyclic Antidepressants being:
        Amitryptyline, Amoxapine, Clomipramine, Desipramine, Doxepin, Imipramine, Nortriptyline, Protriptyline, Trimipramine,
      b. the Monamine Oxidase Inhibitors being:
        Isocarboxazid, Phenelzine, Tranylcypromine,
      c. Other Antidepressants being:
        Burpopion, Fluoxetine, Fluvoxamine, Maprotiline, Mitrazapine, Moclobemide, Nefazodone, Paroxetine, Setraline, Trazodone, Venlafaxine,
    iii. The following Respiratory Stimulants (Bronchodilators):
      Albuterol, Ephedrine, Ethylnorepinephrine, Fenoterol, Isoproterenol, Metaproterenol, Terbutaline,
    iv. The following Hallucinogenic medicines:
      1. the following Indoleamine hallucinogenics: LSD, DMT, N,N-dimethylamine, Psilocybin,
      a. the following Phenethylamines:
        Mescaline, Dimethoxymethylamphetamine (DOM), Methylenedioxyamphetamine (MDA), MDMA,
  b. the Central nervous system depressants consisting of:
    i. The following anaesthetics:
      Halothane, Isoflurane, Enflurane, Methoxyflurane, Sevoflurane, Desflurane, Methohexital, Thiopental, Etomidate, Ketamine, Propofol,
    ii. The following Sedatives and Hypnotics:
      Alprazolam, Brotizolam, Chlordiazepoxide, Clobazam, Clonazepam, Clorazepate, Demoxepam, Diazepam, Estazolam, Flumazenil, Flurazepam, Halazepam, Lorazepam, Midazolam, Nitrazepam, Nordazepam, Oxazepam, Prazepam, Quazepam, Temazepam, Traizolam,
    iii. the Barbiturates being:
      Amobarbital, Aprobarbital, Butabarbital, Butalbital, Mephobarbital, Methohexital, Pentobarbital, Phenobarbital, Secobarbital, Thiopental,
    iv. the Non-barbiturates being:
      Buspirone, Chloral hydrate, Chlormezanone, Diphenhydramine, Doxylamine, Ethchlovynol, Ethinamate, Glutethemide, Hydroxyzine, Meprobamate, Methotrimeprazine, Methyprylon, Promethazine, Propiomazine, Propofol, Zolpidem, Zolpiclone, Paraldehyde,
    v. The Anticonvulsants, (including anti-epileptics) being:
      Acetazolamide, Amobarbital, Carbamazepine, Clobazam, Clonazepam, Clorazepate, Corticotropin, Diazepam, Divalproex, Ethosuximate, Ethotoin, Felbamate, Fosphytoin, Gabapentin, Lorazepam, Magnesium sulfate, Mephenyloin, Mephobarbital, Metharbital, Methsuximide, Nitrazepam, Paraldehyde, Paramethadione, Pentobarbital, Phenacemide, Phenobarbital, Phensuximide, Phenyloin, Primidone, Secobarbital, Trimethadione, Valproate sodium, Valproic acid, vi. The following Tranquillisers (including phenothiazines and their derivatives, rauwolfia, diphenylmethane and its derivatives, alkyl diols and their derivatives) being:

1. Phenothiazines and derivatives being;

Acetophenazine, Chlorpromazine, Chlorprothixene, Flupenthixol, Fluphenazine, Mesoridazine, Methotrimprazine, Pericyazine, Perphenazine, Pipotiazine, Prochlorperazine, Promazine, Thiopropazate, Thioproperazine, Thioridazine, Thiothixene, Trifluoperazine, Trifluoropromazine, a. Other Antipsychotics being:
   Clozapine, Fluspirilene, Haloperidol, Loxapine, Molindone, Olanzapine, Pimozide, Risperidone, Lithium, c. Centrally acting muscle relaxants consisting of:
   Baclofen, Carisoprodol, Chlorphenesin, Chlorzoxazone, Cyclobenzaprine, Dantrolene, Diazepam, Lorazepam, Metaxalone, Methocarbamol, Orphenadrine, and Orphenadrine citrate, Phenyloin, d. Local anaesthetics consisting of:
   Articaine, Benzocaine, Bupivacaine, Chloroprocaine, Cocaine, Diphenhydramine, Etidocaine, Lidocaine, Mepivacaine, Pramoxine, Prilocalne, Procaine, Propoxycaine, and Procaine, Proraracain, Ropivacaine, Tetracaine, e. Medicines Affecting Autonomic Functions consisting of:
   i. The Adrenomimetics (Sympathomimetics) consisting of:
      Phenylethylamine, Epinephrine, Norepinephrine, Dopamine, Dobutamine, Colterol, Ethylnorepinephrine, Isoproterenol, Isoetharine, Metaproterenol, Terbutaline, Metaraminol, Clonidine, Phenylephrine, Tyramine, Hydroxyamphetamine, Ritodrine, Prenalterol, Methoxamine, Albuterol, Amphetamine, Methamphetamine, Benzphetamine, Ephedrine, Phenylpropanolamine, Mephentermine, Phentermine, Fenfluramine, Propylhexedrine, Diethylpropion, Phenmetrazine, Phendimetrazine,
   ii. The Adrenolytics (sympatholytics) consisting of:
      Phenoxybenzamine and related Haloalkylamines, Phentolamine, Prazosin, Terazosin, Doxazosin, Trimazosin, Indoramine, Labetalol, Ketanserin, Urapidil, Alfuzosin, Bunazosin, Tamsulosin, Yohimbine, Propanolol, Metoprolol, Nadolol, Atenolol, Timolol, Esmolol, Pindolol, Acebutolol, Labetalol, Bopindolol, Oxprenolol, Penbutolol, Carvedilol, Medroxalol, Bucindolol, Levubunolol (Betagan) glaucoma, Metipranolol, Bisoprolol, Nebivolol, Betaxolol (Betoptic) Glaucoma,
   iii. The Cholinomimetics (cholinergics) consisting of:
      Acetylcholine, Metacholine, Carbachol, Betanechol, Pilocarpine, Muscarine, Arecoline, Oxotremorine, Ambenonium, Domperidone, Edrophonium, Edrophonium & Atropine, Metoclopramide, Neostigmine, Physostigmine, Pyridostigmine,
   iv. The Cholinolytics (anticholinergics) (including anti-Parkinsonism preparations) consisting of:
      Amantadine, Anisotropine, Atropine, Scopolamine and related Belladonna alkaloids, Ipratropium bromide, Benztropine, piperidine, Chlorpromazine, Clidinium, Dicyclomine, Diphenhydramine, Ethopropazine, Glycopyrollate, Homatropine, Hyoscyamine, Mepenzolate, Methantheline, Methoctramine, Hexahydrosiladifenidol, Himbacine, Tripitamine, Methscopolamine, Orphenadrine HCl, Pirenzepine, Procyclidine, Propantheline, Scopolamine, Thioridazine, Trihexyphenidyl, Carbidopa and Levodopa, Levodopa, Pergolide, Selegiline,
   v. Ganglion blockers consisting of:
      Hexamethonium, Trimethaphan, Mecamylamine,
   vi. Anti-emetics and Antivertigo preparations consisting of:
      5-HT$_3$ Antagonists as Ondansetron, Granisetron, Tropisetron, Dolasetron, D2/5-HT$_3$ Antagonist as Metoclopramide, Trimethobezamide, D2 Antagonists as Phenotiazines namely Chlorpromazine, Perphenazine, Triflupromazine, D2 Antagonists as Benzimidazole derivatives namely Domperidone, D2 Antagonists as Butyrophenones namely Haloperidol, Droperidol, Corticosteroids as Dexamethasone, Methylprednisolone, Cannabinoids as Dronabinol, Nabilone, H$_1$ antagonists Diphenhydramine, Meclizine, Cyclizine, Antimuscarinic agents as Scopolamine, Benztropiane, Benzodiazepines as Lorazepam, Alprazolam, H$_1$ Antagonist as Dimenhydrinate,
   vii. Decongestants consisting of:
      Oxymetazoline, Phenylephrine, Xylometazoline
   viii. -hydroxytryptamine (serotonin) and serotonin antagonists consisting of
      1. 5-HT Agonists being:
      Buspirone, ipsaperone, Sumatriptan, Cisapride,
      2. 5-HT Antagonists being:
      Methysergide, Risperidone, Ketanserin, Ondansetron,
      3. 5-HT transport inhibitors being:
      Fluoxetine, Sentraline,
   f. Anti-Alzheimers agents consisting of:
      Physostigmine, Tacrine and Lecithin in combination with Tacrine.

An agent of specific relevance in this application is doxepin hydrochloride. Doxepin HCl is one of a class of psychotherapeutic agents known as dibenzoxepin tricyclic compounds. Specifically, it is an isomeric mixture of 1-Propanamine,3-dibenz[b,e]oxepin-1,1(6H)ylideneN,N-dimethyl-hydrochloride. In oral formulation it is useful as an antidepressant to relieve symptoms of depression and anxiety such as feelings of sadness, worthlessness, or guilt; loss of interest in daily activities; changes in appetite; tiredness; sleeping too much; insomnia, and thoughts of death or suicide. Doxepin is also sometimes used to treat certain types of pain but it is not generally regarded as an analgesic in the ordinary sense of the word and has been described as one of a group of "adjuvant analgesics" along with other anti-depressants. In a topical formulation, doxepin is known to be used as an anti-pruritic to relieve itching in patients with certain types of eczema. The applicant is unaware of any prior disclosure suggesting that doxepin may beneficially be used in a topical administration form for alleviating pain.

The applicant found that a potent topical formulation may be prepared according to the invention by formulating doxipen with the medium as described.

It is accordingly an aspect of the present invention to provide a topical formulation, used either as a lotion or a cutaneous patch as described above in which doxepin is the active ingredient.

(iii) Nucleic Acid Transportation and Administration

According to the present invention there is also provided a method for the administration of a nucleic acid substance to the cells of an animal, a plant or a miro-organism the method being characterised in that the nucleic acid substance is formulated with an administration medium which comprises a solution of nitrous oxide gas in a physiologically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil, with ethylene oxide.

According to a further aspect of the present invention there is provided a preparation adapted for use in introducing a nucleic acid substance into the cells of an animal, a plant or a micro-organism characterised in that the preparation comprises a formulation of the nucleic acid in an administration medium which comprises a solution of nitrous oxide gas in a physiologically acceptable carrier solvent for the gas and which administration medium includes at least one fatty acid or ester or other suitable derivative thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils, such as castor oil with ethylene oxide.

The administration medium preferably includes the eicosapentaenoic acid [C20: 5ω3] and/or decosahexaenoic acid [C22: 6ω3] as additional long chain fatty acids to at least one of the other components of the carrier medium defined above.

The reaction product of hydrogenated natural oils composed largely of ricinoleic acid based oils with ethylene oxide is preferably produced from castor oil of which the fatty acid content is known to be predominantly composed of ricinoleic acid. This product is known as PEG-n-Hydrogenated Castor Oil. A range of such products is marketed by BASF under the trade description of Cremaphor RH grades. Glycerol-polyethylene glycol ester of ricinoleic acid is also marketed by the same company but under the trade description of Cremaphor EL.

The carrier solvent for the nitrous oxide gas may be water or any of the pharmaceutically acceptable alcohols, ethers, oils or polymers such as a polyethyleneglycol or the like. The oil may be organic or mineral oil. The organic oil may be an essential oil based on long chain fatty acids having between 14 and 22 carbon atoms in the fatty acid. The oil may also be of either natural or synthetic origin and, if of natural origin, it may be either plant oil or animal oil. As plant oils those rich in gamma linolenic acid [GLA] are preferred and as animal oil dairy cream may be used.

In the preferred form of the invention the solution is an aqueous solution saturated with nitrous oxide. Preferably the water is deionised and purified to be free of microbes.

When the formulation containing the nucleic acid substance to be enhanced by means of the nitrous oxide is to be in a liquid (including an encapsulated liquid) presentation for oral administration or in a nasal or bronchial or pulmonary spray or in the form of an injectable formulation, such formulation may incorporate, as part of the administration medium, water or acceptable other liquid into which the nitrous oxide is dissolved and in which the fatty acid or ester thereof is either dissolved or suspended or emulsified along with the nucleic acid substance to be enhanced by being formulated therewith.

Likewise, where the nucleic acid substance is to be administered to the patient as a topical, buccal or vaginal cream or ointment, or as a suppository, the formulation used in making up such cream, ointment, or suppository may incorporate, along with the nucleic acid substance to be enhanced, a quantity of water or other liquid containing, and preferably saturated with, nitrous oxide, the long chain fatty acid or ester thereof and the nucleic acid substance formulated therewith, and, further, such additional excipients and carriers as are conventionally used in the pharmaceutical trade in making up such dosage forms.

The carrier solvent for the nitrous oxide gas may thus in an alternative formulation according to the invention be essentially non-aqueous and composed of the least one fatty acid or ester thereof selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3], ricinoleic acid and derivatives thereof selected from the group consisting of the C1 to C6 alkyl esters thereof, the glycerol-polyethylene glycol esters thereof and the reaction product of hydrogenated natural oils composed largely of ricinoleic acid based oils with ethylene oxide, required to be part of the formulation.

A formulation suited to transdermal application whether as an ointment, cream or lotion or in the form of a skin patch providing a reservoir for the formulation is also a preferred form of the formulation according to the invention.

The essential fatty acid, or ester thereof, component of the composition preferably comprises a mixture of esters of the fatty acids listed above. Thus, in the most preferred form of the invention the fatty acid component of the composition is constituted by the complex known as Vitamin F and in this regard it is preferred to make use of the ester form of Vitamin F known as Vitamin F Ethyl Ester. This product is commercially available under the trade description of Vitamin F Ethyl Ester CLR 110 000 Sh.L. U./g from CLR Chemicals Laboratorium Dr. Kurt Richter GmbH of Berlin, Germany. The typical fatty acid distribution of this product is as follows:

$<C_{16}$: 0
$C_{16.0}$: 8.3%
$C_{18.0}$: 3.5%
$C_{18.1}$: 21.7%
$C_{18.2}$: 34.8%
$C_{18.4}$: 28.0%
$>C_{18}$: 1.6%
unknown: 2.1%

It is further preferred to add to the formulation the long chain fatty acids known as eicosapentaenoic acid [C20:5ω3] and decosahexaenoic acid [C22:6ω3]. Such a product combination is available from Roche Lipid Technology under the trade name "Ropufa '30' n-3 oil".

It has been found by microscopic studies that the formulation of the nucleic acid substance with a medium as herein described gives rise to the formation of minute, generally spherical bodies, within which, or attached to which the active ingredient is contained in a stable form and from which it is delivered at the site of action namely on or inside the cell in or from the animal body or plant or micro-organism to which it is administered.

The nucleic acid substance utilised in the method or formulation according to the present invention may comprise any one or more of the vast spectrum of nucleic acid substances as herein defined.

In a preferred form of the invention the nucleic acid substance is selected from the group comprising: DNA, RNA, DNA-RNA hybrids, oligonucleotides and synthetic nucleic acids.

The invention has not yet been demonstrated by empirical work to be applicable to all the agents or classes of agents referred to herein. However in respect of such nucleic acid substances which have already been formulated with the aforementioned administration medium of the invention, and evaluated by different methods for the anticipated enhancement of action, no negative result has as yet been seen despite the chemical and physical diversity of the nucleic acid substances which have been investigated. The applicant thus confidently expects on the basis of these preliminary observations that the invention will find general application across the entire spectrum of the nucleic acid substances embraced by the term as herein defined and of which some examples are set out herein.

It is part of the applicant's present postulations by which it seeks to find an understanding of the invention and to which it does not wish to be bound at this stage, that while the administration medium of the present invention serves to transport the nucleic acid substance formulated therewith most efficiently through the human or animal body, that medium also plays an important role in transferring, by an as yet unexplained mechanism, the nucleic acid substance through the membranes of and into the cells thereby to cause an effective nucleic acid substance inter- and intracellular concentration of the agent rapidly to be achieved, and to be maintained. It is in this respect that the applicant believes that the present invention will find general application.

From amongst the nucleic acid substances in the form of DNA with which this invention is concerned it relates particularly to DNA fragments making up genes or parts thereof, as are used in gene therapy, and in particular a) to supplement defective genes with 'correct' genes in order to affect the outcome of diseases, as are used in non-viral gene therapy; or b) to transfect cells with exogenous DNA to enable expression of such exogenous DNA as proteins, as are used in biotechnology; or c) to interfere in transcription of genomic DNA, as in therapy of diseases where over-expression of genetic material is a causative effect; or d) to change the regulatory control of the expression of genes, as it may relate to some malignant and other diseases where regulation of gene expression is causative; or e) to transport antisense bacterial, viral or parasitic DNA or oligonucleotides into cells, there to have an inhibitory or stimulatory action on the growth of such infectious agents or a degradative action against the genome or the mRNA of the agent.

The nucleic acid substance used according to this invention may accordingly be those coding for the expression of any desired protein, or protein classes.

The invention is thus applicable to the administration of nucleic acid sequences coding for any one of the following protein classes:
chemokines
chemotactins
cytokines
enzymes
gonadotrophins
growth factors
immunoglobulins
interferons
interleukins
lipid-binding proteins
pituitary hormones
protease inhibitors
proteases
somatomedins More particularly the nucleic acid sequence may be selected to code for any one of the following specific proteins, namely:
adenosine deamidase,
bovine growth hormone (BGH)
brain-derived neurite factor (BDNF)
calcitonin
calcitonin
carboxypeptidase
catalase
cholecystokinin (CCK)
chymotrypsin
ciliary neurite transforming factor (CNTF)
clotting factor VIII
clotting factor VIII
elastase
erythropoietin (EPO)
fibroblast growth factor (acidic or arginase basic)
glucagon
glucagon-like-peptide I (GLP-1)
granulocyte colony stimulating factor .gamma.-interferon(G-CSF)
granulocyte macrophage colony stimulating factor
human growth hormone (hGH)
IL-1
IL-1 RA
IL-2
Insulin
insulin-like growth factor-1 (IGF-1)
insulinotrophic hormone
insulintropin
interferon-.alpha.2B
intrinsic factor
lactase
L-asparaginase
neurite growth factor (NGF)
Ob gene product
parathyroid hormone(PTH)-like hormone
pepsin
phenylalanine ammonia lyase
platelet derived growth factor interferon-.alpha.2A (PDGF)
streptokinase
sucrase
superoxide dismutase (SOD)
thrombopoietin (TPO),
tissue necrosis factor (TNF)
tissue plasminogen activator (tPA)

transforming growth factor (TGF)

trypsin uricase urokinase

The disease conditions which are amenable to treatment using the present invention will be readily apparent to those skilled in the art and include those listed by German et al in the aforementioned U.S. Pat. No. 6,258,789.

The method and composition of the invention may further be characterised in that the carrier compostion may include a peptide selective for a selected receptor on a target cell, such peptide being bound to at least one of the fatty acids or derivatives thereof in the composition. By the presence of such peptide the nanolipid vesicle with its charge of a nucleic acid substance such as DNA may be caused to be targeted to a specific site in the animal or plant body or in the cells so as to dock at at the desired locus for the release of that charge.

Preliminary Hypotheses of Mechanism of Operation

The mechanism by which the enhancement of action of anti-infective drugs and CPNS drugs, and the nucleic acid transportation and delivery is achieved by the present invention, is currently under investigation. Some observations in this regard have been recorded above. In addition it is recorded that preliminary observations point to some additional possible explanations. The applicant again does not wish to be bound to any of the tentative explanations it may put forward at this time. It is recorded, however, that it would appear that the long chain fatty acids used in the formulation of the preparation according to the invention, or at least some of these components, form, during the manufacturing process of the medicinal formulation, very small spherical bodies, hereinafter referred to as "nanolipid vesicles". These nanolipid vesicles have dynamic characteristics in respect of the encapsulation and subsequent delivery of compounds at predicted areas in cells and organisms where the optimal utilisation of these compounds occur with resultant maximised modes of actions.

The present model for the understanding of the invention is that the dynamic delivery characteristics of the nanolipid vesicles are utilised efficiently to transport compounds to locations where maintenance of optimal concentrations in the organisms is beneficial in combating specific infective diseases. The same would appear to apply or diseases responsive to CPNS agents. The cells in this application most probably concern neurons. The long chain fatty acids may contribute to the maintenance of the myelin sheath of the nervous system, being precursors of the sphingomeilin molecules. The dynamic delivery characteristics of the nanolipid vesicles are apparently also utilised efficiently to transport nucleic acid compounds to locations where maintenance of optimal concentrations in the organisms or cells is beneficial in combating specific genetic, acquired and infective diseases.

Infectious diseases, especially those which are known to develop resistance to compounds are known to be difficult to treat due to insufficient penetration of the compound into the causative microorganisms. These, or at least some of these appear to be particularly suited for the benefits of the present invention.

The composition of the invention has thus been found to have beneficial drug delivery effects when exposed to cells and causative organisms harboured by such cells.

These beneficial effects are believed to be attributable to the dynamic characteristics of the nanolipid vesicles. The current hypothesis is that these characteristics include:

1. The Structural Characteristics of the Formulation of the Preparation:

Nitrous oxide and the unsaturated long chain fatty acids forming part of the administration medium are formulated by being mixed with designated anti-infective agents or compounds to form the nanolipid vesicles containing the compound or anti-infective agent. Two important observations have been made in this regard:

a) It was found that when the unsaturated long chain fatty acids used are 20 carbons or more, the nanolipid vesicles form spherical structures with sub-compartments similar to those seen in a sponge.

These structures are stable and it is our belief that antibodies or other ligands would fit ideally in these sub-compartments so that the nanolipid vesicles bind to specific epitopes or receptors at the target cell surface.

b) When unsaturated long chain fatty acids of 16 to 20 carbons are used, the form of the nanolipid vesicles is spherical with a dynamic field of moving autofluorescent particles surrounding the vesicles.

When nitrous oxide is omitted from the process the moving particles surrounding the nanolipid vesicles move erratically and asymmetrical movements are then detected.

It is believed that nitrous oxide is essential in stabilising the moving autofluorescent particles surrounding the nanolipid-vesicles, which is an essential characteristic to efficient compound delivery.

2. Stability:

The nanolipid vesicles appear to remain structurally intact after 24 months at room temperature. Any encapsulated active compounds remain encapsulated during this time. This stability feature is believed to be of substantial significance and one of the contributing factors for the enhancement observed.

3. Absence of Cytotoxicity:

The nanolipid vesicles have no apparent cytotoxicity. When applied to cells in culture, at applicable concentrations they appear rather to have a beneficial effect on normal cell growth.

4. Mechanism of Action:

4.1 Loading Efficiency:

The high loading efficiency of nanolipid vesicles has been demonstrated by achieving a high degree of encapsulation of a wide range of active drugs.

4.2 Transport:

The nanolipid vesicles behave as a transport mechanism to carry molecules such as active compounds.

4.3 Release:

It has been shown that the nanolipid vesicles have very high delivery efficiencies. The high delivery efficiency relates to tissue penetration, cell adsorption, internalisation of nanolipid vesicles by cells, parasites and bacteria, intracellular stability, and subsequent sub-cellular organelle delivery.

The result of high delivery efficiency is the release of active compounds not only at membrane sites, but also at intracellular sites including the nuclei of viable cells or microorganisms. The result is an enhanced efficacy of said active compound. The nanolipid vesicles and active compound appear to act synergistically in attaining enhanced efficacy.

5. Elasticity:
    Confocal laser scanning microscopy (CLSM) shows that the conformation of nanolipid vesicles can be changed while in movement.
    When the vesicles move through membranes, the conformation changes so that the intracellular nanolipid vesicles may have other morphological characteristics.
    While moving through membranes the nanolipid vesicles 'feed' the membranes with unsaturated long chain fatty acids which in its turn will have a positive effect on membrane bound processes. This process has a positive effect on the metabolism of the cell and thus the survival of the cells.
6. Dynamic Inter-Lipid Vesicle Relationships:
    It has been shown that vesicle inter-lipid relationships do exist. The lipid vesicles can interchange the compounds they respectively carry.
    They can also combine to resize themselves continuously without detriment to their stability. The inter-lipid relationship is also revealed when moving through the cellular membrane.
    These interactive membrane characteristics make the movement of the vesicles through the cells optimal.
    Although inter-relationships of the dynamic nanolipid vesicles are continuously present, it has also been shown that the particles are stable in blood and body fluids for up to 5 hours.

EXAMPLES OF THE INVENTION

Without thereby limiting the scope of the invention some examples will now be described to illustrate the invention. Preparations which do not as such form part of the claimed subject matter of this application, being preparations first disclosed in the applicant's own prior patents referred to above, are first restated. Thereafter follows detailed disclosures of preparations falling within the scope of the inention an then follows some illustrations of the utility of the invention and of characteristics of the preparations according to the invention.

Preparation 1

Preparing an Aqueous Nitrous Oxide Solution

A pressure vessel is charged to its operating volume with water at 20° C. [ambient temperature]. The vessel is connected to a supply of nitrous oxide via a flow control valve and pressure regulator. The closed vessel is supplied with nitrous oxide at a pressure of 2 bar for a period of 48 hours, it having been determined that at the aforementioned temperature the water is saturated with nitrous oxide over such period of time under the above-mentioned pressure.

A resultant solution is bottled as stock solution for use in the formulations and applications set out below.

Preparation 2

Preparation of Nitrous Oxide/Vitamin F Aqueous Emulsion 30 g Vitamin F ethyl ester as identified and described above was mixed with 10 g Cremophor RH40 (which is the trade name used by BASF for a product which it describes as the reaction product of hydrogenated castor oil with ethylene oxide which product is also known by the INCI name as PEG-n-Hydrogenated Castor Oil), 2.2 g methyl paraben, 0.08 g butyl hydroxyanisole, 0.23 g butyl hydroxytoluene with stirring at 80° C.

Into 942.5 g of the stock nitrous oxide solution was dissolved 2.5 g sodium propyl paraben and 2.5 g Germall 115 [Imidurea] with stirring at room temperature.

The oily composition first described was emulsified into the aqueous solution with stirring to constitute a stock nitrous oxide/Vitamin F emulsion. It is herein referred to as "Lindil", "MZL" or "nanolipid-vesicle" formulation.

Preparation 3

Preparation of a Non-Aqueous Solution of Nitrous Oxide in Carrier Formulation

The Manufacturing Process for producing a non-aqueous formulation of an anti-infective agent according to the invention will now be described with reference to the manufacture of a first anti-TB medicament containing Pyrazinamide as active ingredient and a second anti-TB medicament containing the combination of Rifampicin, Isoniazid and Ethambutol as active ingredients. These products are respectively designated as "Preparation P" and "Preparation RIE" herein.

Preparation P was made up according to the following protocol:

| | |
|---|---|
| Step 1: | Weigh off the Pyrazinamide 5.00 Kg and reduce the particle size to less than 40 μm. |
| Step 2: | Weigh off and add together the Poloxyl hydrogenated castor oil 1.15 Kg, Vitamin F ethyl ester 2.35 Kg, dl-α-Tocopherol 150.0 g and Polyethylene glycol 400 1.295 Kg into mixing pot 2 and heat to approximately 40° C. until all the oil has melted. |
| Step 3: | Gas the oil mixture with nitrous oxide for 3 hours at 2 bar in the stainless steel pressure vessel in the manner described in Preparation 1 above. |
| Step 4: | Transfer the gased mixture to mixing pot 1 and heat to approximately 70° C. |
| Step 5: | Weigh off and add the Methyl paraben 50.00 g and the Butylated hydroxytoluene 5.00 g to mixing pot 1, while continuously mixing ensuring each solid is dissolved before adding the next while still maintaining the temperature at 70° C. |
| Step 6: | Remove from the heat and allow to cool down to approximately 40° C. |
| Step 7: | Add the Pyrazinamide 5.00 Kg stepwise while continuously mixing. |
| Step 8: | Gas the mixture from step 7 with nitrous oxide at 20 kPa for 30 minutes with mixing until the mixture has reached room temperature. |

Preparation RIE was made up according to the following protocol:

| | |
|---|---|
| Step 1: | Weigh off the Rifampicin 1.467 Kg, Isoniazid 733.00 g and Ethambutol 2.20 Kg and reduce the particle size to less than 40 μm. Ensure that the raw material is protected from exposure to light at all times. |
| Step 2: | Weigh off and add together the Poloxyl hydrogenated castor oil 1.33 Kg, Vitamin F ethyl ester 3.11 Kg and Polyethylene glycol 400 1.30 Kg into mixing pot 2 and heat to approximately 40° C. until all the oil has melted. |
| Step 3: | Gas the oil mixture with nitrous oxide for 3 hours at 2 bar in the stainless steel pressure vessel in the manner as described above. |
| Step 4: | Transfer to mixing pot 1 and continue to mix. |
| Step 5: | Weigh off and add the Methyl paraben 50.00 g, Ascorbyl palmitate 10.00 g and the Butylated hydroxytoluene 5.00 g to mixing pot 1, while continuously mixing ensuring each solid is dissolved before adding the next. |

-continued

Step 6: Remove from the heat and allow to cool down to approximately 40° C.
Step 7: Check the pH and add Potassium hydroxide while continuously mixing until the pH reads 7.
Step 8: Add the Rifampicin 1.467 Kg, Isoniazid 733.00 g and Ethambutol 2.20 Kg, respectively, each stepwise allowing mixing after each addition.
Step 9: Gas with nitrous oxide at 20 kPa for 30 minutes with mixing until the mixture has reached room temperature.

The Preparation P and Preparation RIE formulations were encapsulated in soft gel capsules in the manner well known in the pharmaceutical trade as oral capsules for use as described below.

Preparation 4

Injectable Solution of Active in an Injectable Solution, Containing Nitrous Oxide in Carrier Formulation The manufacturing process for producing an injectable formulation of an active agent according to the invention will now be described with reference to the manufacture of a medicament containing Bupivacaine as active ingredient Preparation X was made up according to the following protocol:
Step 1: Weigh off the 546 g of Bupivicaine HCl and add to the pot. Mix thoroughly with $N_2O$-saturated water until the active compound is completely dissolved.
Step 2: Weigh off and add together the Poloxyl hydrogenated castor oil 1.023 Kg, Vitamin F ethyl ester 3.012 Kg, into mixing pot 2 and heat to approximately 70° C. until all the oil has melted.
Step 3: Weigh off and add the Methyl paraben 214 g and the Butylated hydroxytoluene 36 g to mixing pot 2, in the respective order, while continuously mixing ensuring each solid is dissolved before adding the next while still maintaining the temperature at 70° C.
Step 4: Combine the contents of Step 1 and Step 3 whilst stirring during addition and continue stirring until the phases are well and truly mixed. Determine and adjust the pH to near physiological pH if necessary.
Step 5: Sonicate and check vesicle size.
Step 6: Sterilise by filtration and pack into amber glass ampoules or vials.

Preparation 5

Preparation of a Typical Formulation Having a Non-Aqueous Solution of Nitrous Oxide in Carrier Formulation The manufacturing process for producing a non-aqueous formulation of an CPNS agent according to the invention is based on the principles and ratios of ingredient described with reference to the manufacture of a medicament containing for example Phenylhoin Na as active ingredient Preparation Y was made up based on the following protocol:
Step 1: Weigh of the applicable weight of Phenyloin Na for the purpose required, i.e. age of patients, severity of condition. Reduce the particle size to less than 60 μm.
Step 2: Weigh off and add together the Poloxyl hydrogenated castor oil to a final concentration of 11.5% (w/w) Vitamin F ethyl ester to a final concentration of 23.5% (w/w) and Polyethylene glycol 400 to a final concentration of 12% (w/w) into mixing pot 2 and heat to approximately 40° C. until all the oil has melted. dl-α-Tocopherol may be added depending on the physico-chemical characteristics of the active compound, the rate of release and period of release needed, Eicosapentaenoic acid and/or decosahexaenoic acid may be added at this step.
Step 3: Gas the oil mixture with nitrous oxide for 3 hours at 2 bar in the stainless steel pressure vessel in the manner described in Preparation 1 above.
Step 4: Transfer the gased mixture to mixing pot 1 and heat to approximately 70° C.
Step 5: Weigh off and add the Methyl paraben to a final volume of 0.5% and the Butylated hydroxytoluene 0.05% to mixing pot 1, while continuously mixing ensuring each solid is dissolved before adding the next while still maintaining the temperature at 70° C.
Step 6: Remove from the heat and allow to cool down to approximately 40°C.
Step 7: Add the required amount of Phenyloin Na stepwise while continuously mixing.
Step 8: Gas the mixture from step 7 with nitrous oxide at 20 kPa for 30 minutes with mixing until the mixture has reached room temperature.

The Phenyloin Na Preparation prepared as set out above was encapsulated in soft gel capsules in the manner well known in the pharmaceutical trade as oral capsules for use as described below.

Preparation 6

Preparation of a Typical Formulation Having a Non-Aqueous Solution of Nitrous Oxide in the Carrier Formulation The manufacturing process for producing a non-aqueous formulation of a nucleic acid substance according to the invention is based on the principles and ratios of the ingredients described with reference to the manufacture of a formulation containing the dedicated nucleic acids, which can be a gene or part thereof or a genome or part thereof as in the case of DNA vaccines, or ODN's as in the case of the targeting of infectious agents as active ingredient.

The non-aqueous nucleic acid preparation was made up based on the following protocol:
Step 1: Weigh of the applicable weight of nucleic acids as defined above for the purpose required.
Step 2: Weigh off and add together the Poloxyl hydrogenated castor oil to a final concentration of 11.5% (w/w) Vitamin F ethyl ester to a final concentration of 23.5% (w/w) and Polyethylene glycol 400 to a final concentration of 12% (w/w) into mixing pot 2 and heat to approximately 40° C. until all the oil has melted. dl-α-Tocopherol may be added depending on the physico-chemical characteristics of the active compound, the rate of release and period of release needed. Eicosapentaenoic acid and/or decosahexaenoic acid may be added at this step.
Step 3: Gas the oil mixture with nitrous oxide for 3 hours at 2 bar in the stainless steel pressure, vessel in the manner described in Preparation 1 above.
Step 4: Transfer the gased mixture to mixing pot 1 and heat to approximately 70° C.

Step 5: Weigh off and add the Methyl paraben to a final volume of 0.5% and the Butylated hydroxytoluene 0.05% to mixing pot 1, while continuously mixing ensuring each solid is dissolved before adding the next while still maintaining the temperature at 70° C.

Step 6: Remove from the heat and allow to cool down to approximately 40° C.

Step 7: Add the required amount of stepwise while continuously mixing.

Step 8: Gas the mixture from step 7 with nitrous oxide at 20 kPa for 30 minutes with mixing until the mixture has reached room temperature.

The Nucleic acid Preparation prepared as set out above was encapsulated in soft gel capsules in the manner well known in the pharmaceutical trade as oral capsules. This preparation may be further diluted with water preferably saturated with nitrous oxide to obtain the desired ratios of nanolipid vesicle and nucleic acids.

Example 1

Enhancement of Anti-Bacterial Action

This example pertains to the enhancement of current treatment modalities of infectious bacterial diseases.

The increased efficacy of antibiotics carried by nanolipid-vesicle in the treatment of bacterial infectious diseases was demonstrated by:

| (a) and (b) | Bacterial culture studies (Bactec studies and confocal laser scanning microscopy CLSM); |
| --- | --- |
| (c) | Infection studies involving live confocal laser scanning microscopy (CLSM) studies; and |
| (d) | Zone of Inhibition studies according to the USP XXIII zone inhibition method. |

The following organisms considered to be representative and hence demonstrative albeit not exhaustive of the range of organisms to which the invention relates, were used in the above studies to confirm the invention:
Mycobacteria Tuberculosis (ref strain H37RV)
Mycobacteria Tuberculosis (MDR strains V79 & V25)
*Bacillus* of Calmette and Guerin (BCG)
*E Coli*
*S Aureus*
*P Aeruginosa*
*B. Cereus*
*A. Niger*
*C. Albicans*

The anti-infective agents in the form of anti-bacterials used in these studies, and again considered to be representative and illustrative of the wide application of the invention, albeit not exhaustive, were Rifampicin, Ethambutol, Izoniazid, Pyrazinimide and Povidone-iodine, Cloxacillin, Erythromycin E, Ciprofloxacin, Co-trimoxazole (Sulfamethoxazole and Trimethoprim combination) and Itraconazole.

As will appear from the results discussed below the tests conducted on formulations involving the association of the active ingredient with the carrier prepared as set out in Preparation 2 above, showed a 10 to 40-fold enhancement of the efficacy of selected anti-infective agents compared to conventional formulations thereof.

A. Bacterial Culture Studies:
(a) The effect of the nanolipid vesicle encapsulation on the action of known anti-mycobacterials in BACTEC determinations.

(i) General Methodology of Collection and cultivation of Samples and Evaluation

Clinical isolates of *M. tuberculosis* banked at the Medical School at Tygerberg Hospital were cultured on L-J slant cultures and used for BACTEC analysis. Drug sensitivity determinations in respect of the strains were done. *M. tuberculosis* strains were selected from a bank of 1800 clinical isolates genotyped according to their IS6110 insertion sequence profiles. The insertion sequence ranges from 1 to 23 copies per strain. These strains have been clustered into families according to their genetic patterns and represent recent transmission clusters because of their most frequent appearance in the community. These strains may also represent more virulent strains although virulence factors in M.Tb. have not yet been clarified.

The mycobacterial strains were carefully selected according to their genetic and epidemiological type. Multi drug resistant (MDR) strains were selected over a wide range from mildly resistant to highly resistant for Isoniazid, Rifampicin, Ethambutol and Pyrazinamide. Clinical and laboratory strains of *M. tuberculosis* were cultured in a medium enriched with ADC enrichment medium with continuous stirring to ensure homogenous bacterial distribution and uniform aeration as described by Middlebrook, G. (1977) in "Automatable radiometric detection in growth of *mycobacterium tuberculosis* in selective media." *Ann. Rev. Respir. Dis.* 115:1066-1069. Under these conditions, cultures grow reproducibly (<1.0% difference). This technique was established in the Medical Biochemistry laboratory at Tygerberg Hospital.

At a culture density of approximately A600 nm=0.16 (1× McFarland), (Siddiqui, S. H. (1995). *BACTEC 460 MTB system. Product and procedure manual.*) M.Tb. strain cultures were inoculated into BACTEC vials. Cultures in BACTEC were grown until a growth index (GI) of 500(±50) was reached. This culture was used as starter culture for BACTEC evaluation of carrier encapsulated antimycobacterial drugs. BACTEC growth of cultures was monitored over a period of 6-10 days and the ΔGI value for every 24-hour doubling period determined. Every series of experiments were repeated at least 4 times to allow for accurate statistical analyses. Controls, with no drugs, were brought to the same concentrations. Sterility of mycobacterial cultures were monitored by Ziehl-Nielsen staining.

All experiments with infectious material should be carried out in a category 3 bio-safety laboratory. All experiments should be carried out in such a way as to ensure maximum safety for all other laboratory co-workers.

(ii) Evaluation in Respect of Rifampicin

Lindil, also referred to as the nanolipid vesicle formulation was prepared as described in Preparation 2 above and Rifampicin dissolved at a concentration of 80 micrograms per ml, was used in an initial evaluation of the effect of the preparation on *M. tuberculosis* cultures in BACTEC. This Lindil/Rif preparation was sterilized by filtration through 0.45 micron filters so as not to give background contamination by other bacteria.

*M. tuberculosis* Rifampicin resistant patient isolates were acquired from the South African Institute for Medical Research (SAIMR). Strains TV25 and TV79 were acquired from the strain bank at Tygerberg Hospital. Both were determined to be resistant to Rifampicin, Isoniazid an also streptomycin. The catalase activity of TV79 was found to be negative and that of TV25 to be 5 mM.

Rifampicin was made up in 50% ethanol at a concentration of 10 μg/ml. Eight μl were added to 1ml Lindil to give a concentration of 80 μg/ml Lindil. Of this, 0.1 ml was added to a BACTEC vial to give a final concentration of 2 μg/ml Rifampicin in Lindil. This is the cut-off value at which *M. tuberculosis* strains are evaluated for drug resistance or drug sensitivity for Rifampicin.

Results:

It was found that Rifampicin in Lindil kills drug sensitive strains of *M. tuberculosis* to a much greater extent than Rifampicin alone at concentrations below 2 μg/ml. Microscopy illustrated delivery of Rifampicin by Lindil into the interior of the *bacillus*, and these results show that the Rifampicin does not stay encapsulated in the *bacillus*, but is released from the nanolipid vesicle to the bacilli internal environment for biological activity. Lindil alone has no bactericidal effect at the concentration employed in this determination.

It was further found that the Rifampicin resistant strain used displayed increased Rifampicin sensitivity when Rifampicin is delivered to the bacilli via Lindil.

These results were considered to be very important. It has now been shown that Lindil by itself has anti-mycobacterial activity. The observation that Lindil may have an effect on M.Tb. alone could only be extrapolated from results over the first 24 hours. It would appear that only after a 1:128 dilution of Lindil, growth of M.Tb. is the same as for the untreated control.

It was further found that the application of Lindil/Rifampicin combinations to the Rifampicin resistant strain TV79 resulted in an inhibition of the same order as was observed with the Rifampicin resistant patient isolates which displayed inhibition by Lindil/Rifampicin at a concentration of 0.5 μg/ml Lindil.

(iii) Evaluation in Respect of Isoniazid "INH"

A quantity of MZL as prepared in Preparation 2 was filter sterilized through a 0.22 uM syringe filter (Millipore). MZL was diluted in the ratios of 1:2, 1:8, and 1:32. These dilutions ranged from an inhibitory effect on the viability of M.Tb. to slight inhibition on the viability of M.Tb. These effects were observed with serial dilutions of M.Tb. in BACTEC.

INH was reconstituted with MZL dilutions in two ways: First, dilutions of MZL were made as described before, and INH was added to the dilutions to give a final concentration of 0.1 μg INH/ml MZL per BACTEC vial (4 ml content). Secondly, INH was reconstituted with undiluted MZL to give a final concentration of 0.1 μg INH per ml MZL. The viability of drug resistant strain TV25 was evaluated in the presence of the INH/MZL combinations in BACTEC. The Delta Growth Index (dGI) was calculated for each combination. The dGI is an indicator of Mycobacterial growth over a period of time and is determined: dGI=GI (day+1)−GI (day).

Results

The results are set out in FIG. 1. It shows that after 6 days incubation in BACTEC (dG5), the dGI for M.Tb. strain TV25 was still below 10 in the presence of MZL and INH reconstituted prior to 1:2 dilution, whereas the sample subjected to the formulation in which the 1:2 dilution of MZL was made prior to INH dilution already showed strong positive growth with a dGI=28.

This represented an increased inhibition of 78% compared to the effect of MZL dilution prior to INH addition. The effect of MZL alone was 50% relative to the control for strain TV25. Relative to the control, the effect of MZL combined with INH followed by dilution, was 91%. This gave an additional effectiveness of 41.5% of INH (INH alone showed no effect) in the presence of MZL.

(iv) Evaluation in Respect of Ethambutol

Ethambutol was prepared in sterile deionized water and dissolved in MZL at appropriate concentrations and the mixtures then sonicated in a cup-horn sonicator for one minute at frequency setting 7. It was brought into contact with a culture of *M. tuberculosis* H37Rv known to be resistant to Ethambutol. GI was determined every 24 hours±one hour. The observations are recorded in Table 1.

TABLE 1

H37Rv reference strain treated with Ethambutol. Consecutive treatment of H37Rv with MZL carrier.

| Day | 1 | 2 | 3 | 4 | 5 | 6 | 7 | 8 | 9 |
|---|---|---|---|---|---|---|---|---|---|
| Eth/MZL 8 μg/ml | 7 | 5 | 3 | 2 | 2 | 2 | 4 | 1 | 2 |
| Eth/MZL 4 μg/ml | 5 | 4 | 3 | 3 | 3 | 2 | 3 | 3 | 3 |
| Eth/MZL 2 μg/ml | 6 | 4 | 3 | 4 | 4 | 6 | 6 | 6 | 6 |
| Eth/MZL 1 μg/ml | 6 | 5 | 4 | 10 | 13 | 22 | 31 | 43 | 56 |
| Eth/MZL .5 μg/ml | 5 | 5 | 5 | 10 | 20 | 39 | 68 | 109 | 159 |
| Eth/MZL .25 μg/ml | 5 | 5 | 4 | 7 | 16 | 39 | 75 | 138 | 207 |
| Eth/MZL .125 μg/ml | 5 | 4 | 4 | 8 | 19 | 46 | 89 | 142 | 199 |
| Eth/MZL .0625 μg/ml | 5 | 4 | 7 | 14 | 31 | 69 | 127 | 171 | 210 |
| Eth/MZL .03125 μg/ml | 5 | 5 | 7 | 15 | 33 | 66 | 123 | 182 | 215 |
| Eth 8 μg/ml | 16 | 18 | 17 | 18 | 15 | 14 | 13 | 15 | 16 |
| Eth 4 μg/ml | 21 | 23 | 26 | 28 | 27 | 27 | 27 | 25 | 23 |
| Eth 2 μg/ml | 21 | 24 | 27 | 32 | 34 | 38 | 39 | 48 | 54 |
| Eth 1 μg/ml | 15 | 19 | 23 | 29 | 31 | 40 | 47 | 55 | 69 |
| Eth .5 μg/ml | 15 | 21 | 29 | 48 | 66 | 100 | 138 | 162 | 205 |
| Eth .25 μg/ml | 21 | 36 | 62 | 110 | 160 | 265 | 349 | 427 | 487 |
| Eth .125 μg/ml | 21 | 45 | 92 | 200 | 307 | 603 | 785 | 873 | 933 |
| Eth .0625 μg/ml | 20 | 45 | 97 | 211 | 338 | 630 | 840 | 999 | 999 |
| Eth .03125 μg/ml | 20 | 43 | 96 | 218 | 377 | 655 | 909 | 999 | 999 |
| Control | 19 | 43 | 91 | 220 | 336 | 540 | 534 | 561 | 528 |
| Control + MZL | 7 | 5 | 8 | 21 | 44 | 95 | 186 | 280 | 415 |

Calculations:

Figures in the highlighted column (6) were used to calculate the effect of Ethambutol on mycobacterial growth in the absence of MZL. At this point the untreated TB control is GI=540. This is also the point where the TB growth becomes stationary (decline in growth). All GI values in this column were calculated relative to the control value of 415 to give % inhibition of growth. Column (9) shows the MZL treated control at approximately GI=415. All GI values in this column (Ethambutol in the presence of MZL) were calculated relative to the control value of 415 to give % inhibition of growth. The untreated control value was normalized to 415 to make results comparable. The results of the calculations are set out in Table 2.

TABLE 2

| | Plus MZL % Inhibition | Minus MZL % Inhibition |
|---|---|---|
| 1.0 μg/ml Ethambutol | 86 | 92 |
| 0.5 μg/ml Ethambutol | 62 | 81 |
| 0.25 μg/ml Ethambutol | 51 | 51 |
| 0.125 μg/ml Ethambutol | 52 | −12 |

TABLE 2-continued

|  | Plus MZL % Inhibition | Minus MZL % Inhibition |
|---|---|---|
| 0.0625 µg/ml Ethambutol | 49 | −16 |
| 0.0325 µg/ml Ethambutol | 48 | −21 |

Results:

The results show that the MIC for Ethambutol in *M. tuberculosis* H37Rv strain is around 1.0 µg/ml. Results clearly show that from 0.125 µg/ml Ethambutol, MZL presence still maintains a strong inhibitory effect on mycobacterial growth compared to MZL untreated bacteria whereas there was no growth inhibition. In fact, a slight stimulation of growth (negative values) is observed. This is usually observed with very low antibiotic manipulations. At the higher Ethambutol concentrations (0.25-1.0 µg/ml) there does not appear to be much difference in growth inhibition between MZL treated and untreated. The very high concentrations appear to have a better effect in the untreated M.Tb. This effect could be a dose response because of the very high presence of Ethambutol at the high concentrations. In the MZL treated experiments it appears as though MZL captures Ethambutol in its structure making less Ethambutol freely available for diffusion over the mycobacterial membrane. However as the concentrations become lower it appears that MZL gives a steady delivery of Ethambutol to the M.Tb. with the result that inhibition is steadily maintained (approx 50% inhibition over the range of 0.03125 µg/ml-0.125 µg/ml).

From these results it appears that MZL maintains steady state delivery of Ethambutol to the M.Tb. over the spectrum of concentrations used and this effect is most prominent in the low concentration range of MZL that is the concentration range significant for therapeutic efficacy.

(b) The effect of nanolipid-vesicle encapsulation of the antibiotic Pyrazinamide on the resistance of BCG (*Bacillus* of Calmette and Guerin) to Pyrazinamide:

The encapsulation of antibiotics Izoniazid, Ethambutol and Rifampicin into the nanolipid vesicles formulation of Preparation 2 described above resulted in a product suitable for use in the inhibition of *Mycobacterium Tuberculosis* in bacterial isolates from patients infected with both drug-sensitive and multidrug resistant strains. The results were obtained with the Bactec system, with no human cell involvement.

The significance of the following result stems from the fact that the BCG vaccine is extensively used for vaccination against infection by *Mycobacterium Tuberculosis* (M.Tb.). BCG vaccine is classified as a non-pathogenic mycobacterial strain and is therefore a widely used investigative model of infection by (M.Tb.). All BCG strains are resistant to Pyrazinamide (see Morbidity and Mortality Weekly Report; 1996, vol 45, No RR-4). The effect of encapsulation of this antibiotic by nanolipid vesicles according to the invention and its delivery in that form to BCG was investigated.

In this investigation which was performed by confocal laser scanning microscopy (CLSM), use was made of a live/dead fluorescent stain known as Baclight. It stains live bacteria green and dead bacteria red. General viability of the BCG's was determined by the green/red ratio of the bacteria. The effect of equal amounts and concentrations of free and nanolipid-vesicle encapsulated Pyrazinamide on BCG viability was investigated.

Bacterial viability: The general viability of the BCG's before any addition of antibiotics was between 85-95%. The BCG-viability after a two-hour incubation of the applicable dosage of free Pyrazinamide was 68-72%.

Bacterial growth characteristics: BCG generally grows in clumps. Incubation with free Pyrazinamide resulted in the appearance of single live bacteria with a few granuloma-type clumps, which gradually secrete single live bacteria. The single live bacteria were mobile. Encapsulation of Pyrazinamide in nanolipid-vesicles led to a 65-75% decrease in BCG viability within a two-hour incubation. No moving BCG was observed.

Accordingly, BCG prelabelled with live/dead Baclight bacterial stain and then treated with nanolipid-vesicle encapsulated Pyrazinamide was observed by confocal laser scanning microscopy. It was found that, after an hour, most of the bacteria were labelled red, and were therefore dead. No granuloma-type clumps or single bacteria were observed. Such clumps and single bacteria, all coloured green, were seen in the control in which the same quantity of Pyrazinamide in water alone was, brought into contact with BCG also prelabelled with live/dead bacterial stain.

The study thus yielded the most surprising result that bacterial resistance to Pyrazinamide may be overcome by encapsulation of the antibiotic into the nanolipid vesicles composition of Preparation 2.

(c) Infection studies (Live confocal laser scanning microscopy studies)

In this study the aim was to determine whether encapsulation of an antibiotic by nanolipid vesicles gives rise to a product by which one could overcome resistance of intracellular bacteria, using infection of human macrophages by BCG in culture as a cell model.

The THP1 macrophage cell line (ATCC) was used for the infection study. RPMI 1640 with L glutamine cell culture medium, Foetal Bovine Serum and phosphate buffered solution (Gibco BRL), were used for cell growth according to general cell culture methods. THP1 macrophage cells were cultured and infected with pre-treated labelled BCG bacteria. Treatment consisted of equal concentrations namely 0.075 µg/ml of free and nanolipid-vesicle encapsulated Pyrazinamide. CLSM was used to determine infection by and survival of the bacteria.

The viability of BCG's after infection in macrophages reflects that BCG's inside macrophages treated with nanolipid-vesicle associated Pyrazinamide is effectively killed by the antibiotic Pyrazinamide, even though the bacteria are generally recognised to be resistant to the antibiotic used.

(d) Zone of Inhibition Studies:

(i) Enhancement of Povidone iodide against two bacterial organisms as evidenced by zone of inhibition studies.

Inhibition of bacterial growth of two types of bacteria by the active ingredient known as Povidone iodine in formulated form with the nanolipid vesicles of Preparation 2, and so used at a concentration of 6.30 g Povidone iodine equivalent to 0.75 g available Iodine in 100 g of product, was compared with the effect of the same amount and concentration of the free active ingredient. The bacteria were *S. Aureus* and *P. Aeruginosa*. The control used was saline.

The results obtained in the study are graphically represented in the graph which is FIG. 2 hereto. It is clear that inhibition of bacterial growth in both types of bacteria is dramatically increased when the active is associated with the nanolipid vesicles.

(ii) Enhancement of five anti-infective agents against five different bacterial organisms Five commercially available antibacterial compositions containing the active ingredients set out in Table 3 below were compared in zone inhibition studies with saline as control with compositions of the same active ingredients made up in a carrier according to the invention. These are designated "MZL" formulations in the case of aqueous made according to preparation Z above and "MZLA" formulations in the case of non-aqueous formulations prepared according to Preparation 3 above. This convention is also followed in other examples below as opposed to the commercial formulations (COM) of particular active agents. The compared formulations were diluted where necessary to achieve the same concentrations.

It is evident from the results set out below that the organisms were more sensitive to the active agents when encountered in the carrier formulation according to the invention.

TABLE 3

ZONE OF INHIBITION STUDY: FIVE COMMERCIAL ANTI-INFECTIVE FORMULATIONS AGAINST FORMULATIONS ACCORDING TO THE INVENTION FOR DIFERENT INFECTIVE AGENTS

| ACTIVE AGENT | MZLA/ Com | Dose mg/ 5 ml | S. Aureus | P. Aerugin | B. Cereus | E. Coli | A. Niger | C. Albicans |
|---|---|---|---|---|---|---|---|---|
| Cloxacillin | MZL | 125 | 30.74 | 23.96 | | | | |
| Cloxacillin | COM | 125 | 29.45 | 19.86 | | | | |
| Erythromycin | MZL | 250 | 26.7 | | 29.89 | | | |
| Erythromycin | COM | 250 | 25.84 | | 27.78 | | | |
| Ciprofloxacin | MZL | 250 | 33.05 | | | 35.78 | | |
| Ciprofloxacin | COM | 250 | 30.14 | | | 33.4 | | |
| Cotrimoxazole | MZL | 240 | 13.95 | | | 24.64 | | |
| Cotrimoxazole | COM | 240 | 11 | | | 22.83 | | |
| Itraconazole | MZLA | 50 | | | | | 16.03 | 14.28 |
| Itraconazole | COM | 50 | | | | | 10.21 | 11.47 |
| Control | | | 9 | 9 | 9 | 9 | 9 | 9 |

Example 2

Enhancement of Anti-Viral Agents

In this study AZT at different dosages was associated with the nanolipid vesicles to test the efficacy of such association on the viral growth in CD4+ Helper T-cells.

The rationale for this investigation is that AZT is cytotoxic and long-term use is associated with loss of muscle. Other side effects can be nausea, anaemia, white blood cell depression, mouth sores, bone marrow damage, and headaches. It would therefore be desirable from both a side effect and cost perspective to be able to lower the dosage of AZT administered to an HIV-infected patient, provided that such lowering of dosage does not compromise the effect of the administration. It was thus decided to investigate the dose/effect relationship of AZT when formulated with the administration medium of Preparation 2.

Although it was the result the applicant had hoped for, it was nevertheless a surprise to find that these objects may be accomplished by increasing the effective delivery of AZT to HIV-infected cells, thereby maintaining a therapeutic intracellular concentration at lower dosages. From the observations made it is presently postulated:

a) That the AZT-loaded nanolipid vesicles significantly increase the kinetics of intracellular and intranuclear AZT delivery, with the result that AZT therapeutic dosages can be decreased;
b) That nanolipid vesicle-associated AZT appears to assume the pharmacokinetics of the vesicles until such time as it is released and;
c) That the optimal loading concentration for AZT-loading into nanolipid vesicles can be determined with regard to the applicable cell types.

The following protocols were followed in this investigation:

a) Several cultures of CD4 helper T-cells (CEM-SS cell line; NIH AIDS Research and Reference Reagent Program) were infected with HIV subtype D viruses at applicable cell seeding densities and viral loads. Cells were maintained in tissue culture under standard culturing conditions.
b) The viral load in cultured cells were determined every day for 7 consecutive days after infection by measuring the p24 core antigen of HIV-1 in the supernatant culturing fluid by ELISA. This assay is based on a colour change after addition of substrate that is proportionate to the viral replication in each culture. The colour change is monitored by absorbance spectrophotometry at 450 nm. Negative control absorbance readings were used to calculate the absorbance/cut-off for each culture.
c) Determination of the optimal concentration of nanolipid-vesicle containing base formulation was done by cytotoxicity assays and cell growth curves. The cytotoxicity assay used was the standard MTT assay and spectrophotometry was once again used to determine cell viability for the CEM-SS cell line. Growth curves were used to determine the optimal concentration of base formulation for human macrophage cells (THP-1 cell line).

The results obtained are graphically presented in FIG. 3 hereto. It shows the following:

a) The delivery and transport function of the nanolipid-vesicles increase the therapeutic efficacy of AZT ten fold at a dilution of 1:512 base formulation, thereby creating the possibility of decreasing the AZT dosage 10 fold, as is shown by the relative effect of 1 nM free AZT versus 0.1 nM nanolipid-vesicle formulated AZT. The results clearly show that the addition of 0.1 nM free AZT inhibited viral growth and replication by 44% by day 7 and 8, when compared to the control (no AZT added). However, the addition of 0.1 nM nanolipid vesicle-associated AZT inhibited viral growth by between 70-80% on day 8. This is comparable to the inhibition observed by 1 nM free AZT (i.e. 10 times the concentration). Furthermore, addition of 0.1 nM nanolipid vesicle-associated AZT showed a continued decrease in viral load over 8 days, whereas the addition of even 10× that amount of free AZT resulted in a decrease in viral load up to day 6, after which the viral growth increased slightly.

b) The graphs in FIG. 2 show that the association of AZT with nanolipid vesicles changes the pharmacokinetics and possibly the intra-cellular biodistribution of AZT.

c) The effective delivery of the basic nanolipid vesicle formulation has been established for CD4 T-cells and macrophages to be a dilution of between 1:512 and 1:1024 of the concentrated unfiltered formulation. Higher content of nanolipid vesicles appears to favour viral growth in the cells. At a dilution of base-formulation (1:256), viral inhibition is optimal at a higher concentration of AZT (0.5-1 nM).

Note that no correction has been made in the above evaluation for the contribution of the cells itself to the Absorbance/cut-off ratio. It was considered to be negligible (>0.4).

Conclusions:

a) The administration medium of Preparation 2 at the correct dilution may be used to decrease the effective therapeutic dosage of AZT by as much as 10 fold. It would considerably decrease the cytotoxicity of the AZT treatment. At such low dosages, it may be more attractive to treat expecting mothers for HIV infection, without any long-term side effects on the foetus.

b) Optimisation of nanolipid vesicle concentration for AZT-delivery is essential, as unloaded nanolipid vesicles can favour the multiplication of HIV viruses by supplying components for viral membranes synthesis and energy for viral metabolism, as the metabolism of nanolipid vesicle essential fatty acids (EFAs) may increase the energy status of the cell, and therefore also the energy available to the HIV virus for its replication. The nanolipid vesicle concentration must therefore be sufficient to serve only its transport function, without supplying either membrane components or energy for viral multiplication.

The changed pharmacokinetics and intracellular biodistribution of AZT transported by nanolipid vesicles are probably the result of the following two mechanisms:

a) the change in environment with regards to charge and hydrophobicity when nanolipid vesicles move from the extracellular to the intracellular environment, and b) the normal cellular pathways of the EFAs, which include its metabolism in the mitochondria. The release of AZT is therefore most probably in the region of the mitochondria.

Example 3

Yeasts and Fungi

The Enhancement of Agents Used in the Treatment of Infectious Diseases Caused by Yeasts and Fungi The use of this invention for the enhancement of agents used in the treatment of yeasts and fungi (moulds) was investigated and established by the following studies described in greater detail below, namely:

Comparative culture studies

Infection studies (Live CLSM imaging)

Zone inhibition.

(a) Comparative Culture Studies:

Fungi of the mycosis type was grown in culture medium (RPMI 1640 with L glutamine cell culture medium) at 37° C. at 90% humidity, 5% $CO_2$ for a week. Equal aliquots of grown fungi were exposed to nanolipid vesicles loaded with a commercially available antifungal agent containing 2% Miconazole nitrate. Comparison was made with free Miconazole nitrate i.e. the commercially available form of that active ingredient. In both instances the exposure was at a final concentration of 0.4% over similar time periods (30 minutes to 18 days), using a single initial dosage.

Results:

The nanolipid-vesicle delivery system can be used for the efficient delivery of antifungal agents to fungi.

Miconazole nitrate association with nanolipid vesicles, but not free Miconazole nitrate caused a fast and unexpectedly dramatic decrease of the fungi as illustrated in Table 4.

TABLE 4

VIABILITY OF FUNGI AGAINST TIME ELAPSED AFTER SINGLE EXPOSURE TO MICONAZOLE NITRATE

| Time | Nanolipid-vesicle encapsulated Miconazole | Free Miconazole |
|---|---|---|
| 30 min | 5% | 80% |
| 4 hours | 0% | 70% |
| 11 days | 0% | 30% |
| 18 days | 1% | 15% |

(b) Infection Studies:

Two equal aliquots of melanoma cells (UCT MeI 1 cell line) were incubated for 4 hours with fungi and 0.2% of either free Miconazole nitrate or Miconazole nitrate formulated with the administration medium of Preparation 2 in order to test the effect of the formulation in terms of the invention on the efficacy of fungal treatment of human cells.

The viability of both human melanoma and human macrophages was found to decline dramatically in the presence of free Miconazole nitrate but not when the Miconazole is encapsulated in nanolipid vesicles. The result is graphically presented in FIG. 4 hereto.

FIG. 4 shows the viability of both the human melanoma and fungi 4 hours after the addition of the therapeutic agents in a petri dish.

Using a macrophage cell line, the same result was obtained.

Melanoma cells were healthy after 4 hours incubation with nanolipid-vesicle encapsulated Miconazole nitrate and no fungi was present. In the presence of free Miconazole nitrate, cells were no longer attached to the petri dish and fungi were still present in large numbers.

(c) Zone of Inhibition Studies:

Zone of inhibition studies on yeasts and moulds namely *C. Albicans, T. Mentagrophytes* and *E. Flocossum* were also carried out. Inhibition of yeast and mould growth by the active ingredient Miconazole nitrate in association with nanolipid vesicles was observed. The control used was saline.

The result of this study is reflected in FIG. 5 hereto

Conclusion:

It is quite clear from the results presented in FIG. 5 that the active Miconazole nitrate in association with the nanolipid vesicles inhibits the growth of both yeasts and moulds and does so to a greatly enhanced extent.

Example 4

Parisitology

The Treatment of Infectious Diseases Caused by Parasites

Summary:

The effect of free and non-aqueous nanolipid formulated chloroquin made according to the process described in Preparation 3 against a resistant Falciparum strain (the reference strain W2 for drug resistant malaria) was preliminarily determined in the conventional manner. The strain is known to have a 50% Inhibition concentration value ($IC_{50}$) of between 200-300 nmolar Chloroquine. The determined $IC_{50}$ value for nanolipid formulated Chloroquine was about one tenth of the value for free chloroquine, namely 25-30 nmolar. This most surprising result holds substantial promise for further research as its utilisation in practice means that malaria would be capable of being treated with greatly reduced cytotoxicity and resulting lower incidence of side effects. In addition drug cost will also be lower.

Approach and General Method

The specific parasite investigated was the reference drug resistant strain W2 of the species Plasmodium Falciparum. Plasmodium Falciparum is the most commonly occurring as well as the most virulent malaria parasite currently known in man.

The system used in this investigation aims to mimic the live situation as closely as possible. For that reason, the parasites were infected into fresh primary erythrocytes isolated from O+ or A+ blood donors.

Furthermore, human serum prepared from the same donors was used as an adjuvant instead of foetal calf serum. Parasite growth was maintained by the addition of freshly prepared erythrocytes from the same donors.

The growth of the parasites was determined by visualization of the parasite DNA on thin smears of the infected cultures. Since mature erythrocytes contain no nucleus, and therefore no DNA, the only DNA present was of parasitic origin. Only intracellular parasites were included in determining the percentage parasitaemia, as extracellular parasites are no longer viable.

Protocol:

The protocol was typical for work of this nature and included the following steps as will be readily apparent to those skilled in the art.

A. Culturing of Malaria Parasites:
1. Preparation of fresh human erythrocytes
2. Preparation of human serum from the same donor.
3. Quality control of human serum.
4. Infection of erythrocyte cultures with parasites. Initial infection load was 0.5% parasitaemia.
5. Maintenance of parasite blood cultures
6. The parasite percentage in the blood cultures was determined after 36 or 48 hours, depending on the level of infection of the freshly added erythrocytes.

B Basic Toxicology:

Determination of possible toxic effect of nanolipid formulations on erythrocytes and parasite growth.

The following nanolipid formulation concentrations were investigated: 0.1:1500, 1:1000; 1:750; 1:500; 1:250; 1:100; undiluted.

C Loading of Nanolipid Formulation with Chloroquine:

A stock solution of 10 mM chloroquine solution in a 1:250 dilution of nanolipid formulation was made by vortexing and sonication. All concurrent dilutions were from this stock.

D Drug Delivery by MZL Nanolipid Formulations:
1. Penetrance of nanolipid formulations in red blood cells was determined by microscopic visualization, as were the penetrance of chloroquine-carrying nanolipid formulations.
2. The drug concentration series used centred around the known 1050 concentration of chloroquine in the W2 strain.
3. Typically 48-well plates or 96-well plates were used. 200 ul or 100 ul total culture volumes were used respectively, of which 90% of the volume was infected erythrocyte culture. 10% volume was used for the treatment, be it chloroquine in Nanolipid formulation, chloroquine in water, or for the controls 1:250 pure Nanolipid formulation, pure culturing media or water only.
4. All series were in duplicate.

E Visualization of Intracellular Parasites:

Parasitic DNA was visualised by Giemsa staining of thin smears. Ethidium bromide or acridine orange may be used for fluorescent staining.

F % Parasitaemia:

The % infection after applicable incubation periods was determined as follows:

$$\frac{\text{Total parasite count per 10 microscopic fields}}{\text{Total cell count per 10 microscopic fields}} \times 100\%$$

G Quality Assurance of Counting:

All counts of the first series were undertaken by two scientists. The results correlated very well. The second series was spot-checked by a second scientist, especially around crucial concentrations. Once again no significant deviations were found between the two sets of results.

Results:

The counts of the cultures are reflected in the table 5 below:

TABLE 5

| Chloroquine concentration | CLQL Cells/field | Total cells | Parasites | % Parasit + MZL | CLQ Cells/field | Total cells | Parasites | % Parasit |
|---|---|---|---|---|---|---|---|---|
| 0 nM | 95 | 950 | 17 | 1.8 | 73 | 730 | 16 | 2.19 |
| 1 nM | 87 | 870 | 18 | 2.06 | 127 | 1270 | 34 | 2.67 |
| 5 nM | 127 | 1270 | 29 | 2.88 | 60 | 600 | 14 | 2.33 |
| 10 nM | 130 | 1300 | 37 | 2.84 | 135 | 1350 | 40 | 2.96 |
| 25 nM | 120 | 1200 | 23 | 1.91 | 130 | 1300 | 37 | 2.84 |
| 50 nM | 90 | 900 | 13 | 1.41 | 111 | 1110 | 30 | 2.7 |
| 75 nM | 54 | 540 | 5 | 0.9 | 129 | 1290 | 43 | 3.33 |
| 100 nM | 125 | 1250 | 14 | 1.1 | 64 | 640 | 18 | 2.81 |
| 200 nM | 106 | 1060 | 4 | 0.3 | 108 | 1080 | 31 | 2.87 |

TABLE 5-continued

| Chloroquine concentration | CLQL Cells/field | Total cells | Parasites | % Parasit + MZL | CLQ Cells/field | Total cells | Parasites | % Parasit |
|---|---|---|---|---|---|---|---|---|
| 300 nM | 88 | 880 | 13 | 1.41 | 105 | 1050 | 19 | 1.8 |
| 500 nM | 63 | 630 | 7 | 1.1 | 76 | 760 | 0.15 | 1.5 |
| 1000 nM | 87 | 870 | 12 | 1.3 | 71 | 710 | 10 | 1.4 |

W2=Chloroquine resistant strain internationally recognized and used.

CLQL=Chloroquine in 1:250 dilution MZL nanolipid carrier; concentrations of chloroquine as indicated.

CLQ=Chloroquine in medium at the specified concentrations.

Resistant strains become sensitive only at very high Chloroquine concentrations.

Association of chloroquine with nanolipid formulation results in a similar susceptibility as sensitive strains.

Statistical analysis of the results was by Chi-square analysis between the two sets of data. A combination of the 3 repeats of the two sets of data gives a Chi-square value of 7.6. According to the probability tables, the difference between pure chloroquine and MZL-associated chloroquine is highly significant, with only a 0.0001 probability that the difference observed between the two treatments is due to chance.

Conclusions:
1. The association of chloroquine with MZL nanolipid formulation significantly decreases the $IC_{50}$ of chloroquine (by 6× to 10×).
2. Primary human cells show high tolerance for the MZL nanolipid formulation, with cytotoxicity only observed at high extremely high concentrations.
3. MZL formulations may be used in the prophylaxis of drug resistant malaria.

Example 5

Comparative Release Properties as Determined by Membrane Diffusion of Anti-Infective Agents Formulated in Accordance with the Present Invention and Commercially Available Formulations of the Same Anti-Infective Agents 1. Objective The scope of this study was to establish whether the Test Anti-infectives Acyclovir and Miconazole Nitrate are released from the dosage form of the invention at a satisfactorily rate and extent in comparison to the commercially available Comparators.

The applicability of the test method for release out of the dosage forms was confirmed by Handbook of Dissolution Testing: Dissolution Testing of Transdermal Delivery Systems, page 61. The small receptor volume to be used, in this case 12 m, is confirmed in the same reference on page 63, which refers to 5-25 m.

2. Method

The in vitro release from the dosage forms was determined by a Hanson Model 57-6M, Manual Start-Up, Diffusion Cell Test System bought from Hanson Research with the following main parts:

CELL DRIVE CONTROL
6-CELL DRIVE WITH CELLS
VERTICAL CELLS

3. Parts Needed
1. Diffusion cell assembly, including donor top and receptor chamber (set of 6). The donor top includes a drug dosage wafer (Teflon washer), an acrylic top plate, and a clamp to connect top to bottom.
2. Pig skin used within 24 hours from being slaughtered kept in Ringer Solution between 2° C.-8° C.
3. Davies Gold Series Dermatone, Simplex GS102.
4. Application squeegee and tweezers.
5. Drug dosage form.
6. Absorbent paper towels and tissues.

4. Technique
1. Obtain skin from pig heads (jawbone skin). Use Dermatome according to the Operation standard operating procedure for the Dermatone, setting it to size the skin to a thickness of 0.33 mm. The diameter of the skin should be in excess of the drug dosage wafer.
2. Prepare receptor chamber of diffusion cells with slight overflow of medium (pH 5 buffer with glacial acetic acid for the Test Product Acyclovir and 6.8 phosphate buffer for the test product Miconazole) with temperature controlled at 32° C.
3. Prepare each piece of skin with the relevant products one at a time as follows:
   3.1. Lift skin with tweezers, place on tissue and blot excess of solution, invert and blot.
   3.2. Place skin in centered position on drug dosage wafer.
   3.3. Place relevant products on top of skin in dosage wafer cavity—0.5 ml by means of a Gilman pipette—weighed and averaged to obtain dosage applied.
   3.4. Use squeegee to carefully smooth product over membrane, filling entire cavity.
   3.5. Wipe excess dosage water with squeegee.
   3.6. Lift loaded dosage wafer with skin and place on top of receptor cell with skin side towards cell medium. Exclude bubbles during process. Place on top of donor cell assembly, pressing down with finger, squeezing out bubbles between top plate and dosage form. Apply clamp to lock down top donor and bottom receptor halves of diffusion cell.
5. Operation of Apparatus The apparatus must be set to 150 rpm. Samples of 150 µl are withdrawn with a micropipette at 2', 5', 8' and 10' and 15 minutes. The samples after being withdrawn are analysed for Acyclovir and Miconazole Nitrate respectively by means of HPLC according to the parameters set out in Table 6 below.

TABLE 6

|  | Acyclovir | Miconazole Nitrate |
|---|---|---|
| Injection volume | 20 µl | 20 µl |
| Column | Zorbax SB C18 | Zorbax SB C18 |
|  | 250 mm × 4.6 mm | 250 mm × 4.6 mm |
| Mobile Phase | 0.02 M GAA in $H_2O$ | 70% Methanol |
|  | pH 3.5 | 30% $H_2O$ + 1% GAA |
| Detector | HPLC at 254 nm | HPLC at 224 nm |
| Temperature | Ambient (22° C.) | Ambient (22° C.) |
| Flow Rate | 1.5 ml per min | 1.5 ml per min |

TABLE 6-continued

|  | Acyclovir | Miconazole Nitrate |
|---|---|---|
| Retention Time | 20.8-21.9 min | 9.4-9.9 min |
| Solvent | MP adjusted to pH 5 | Methanol |
| Cells used | 3 (1 for Comparator) | 6 |
| Time at which total release determined (Min) | 15 | 60 |

6. Results

The release experiment was performed in the number of cells indicated above for each product and the mean release is reported for each analysis point. The results are tabulated and graphically presented. The results as a percentage of the active released per label claim per cell at the different time intervals is also tabulated.

In Table 7 below is shown a summary of the release rate and percentage release per label claim for the products determined according to calculations, reporting the mean values of the utilised number of cells of each product after the effluxion of the time indicated above.

TABLE 7

Table indicating release rates and percentage release per label claim for product tested.

| Active Agent | % Active/ product | Release Rate ($\mu g/cm^2/h$) | % Release per label claim |
|---|---|---|---|
| Acyclovir MZL | 0.5 | 69.1533 | 0.1214 |
| Acyclovir COM | 0.5 | 54.0942 | 0.0952 |
| Miconazole Nitrate MZL | 2 | 389.9238 | 6.8155 |
| Miconazole Nitrate | 2 | 111.2222 | 1.9466 |

7. Calculations

The Release Rate was calculated as follows:

7.1. μg Active Released at time (min.) =

$$\frac{A\,sam \times Mass\,Std \times Vol\,Receptor \times Mass\,of\,Active\,Applied\,for\,Z\,cells \times C}{A\,std \times Vol\,Std \times Label\,Claim \times Mass\,of\,Product\,Applied\,for\,1\,cell \times Z \times 100}$$

WHERE:
A sam = Area of peak sample solution
A std = Area of peak of standard solution
Mass std = Mass of standard taken to prepare the standard solution expressed in μg
Vol Std = Volume to which the standard solution is made up, expressed in m
Label Claim = Amount of active present per 100 g of product
Mass of Product Applied for 1 cell = Specific amount of product applied for a specific cell
Mass of Active Applied for Z cells = Amount of active applied in total for all Z cells utilised per one study
C = potency of the standard, expressed as a percentage 7.2. Accumulative Dose (μg) released/square cm at time (min) =

$$\frac{\mu g\,Active\,Released}{(Surface\,Area\,of\,Exposed\,Skin)} = \frac{\mu g\,Active\,Released}{1.767\,cm^2}.$$

7.3. Release Rate = $\dfrac{Accumulative\,Dose\,(\mu g)\,released/square\,cm}{Time\,(hours)}$ 7.4. Percentage of Active Released at time (min.) =

$$\frac{\mu g\,Active\,Released \times 100}{\mu g\,Active\,Applied}$$

8. Conclusion

From the aforegoing test it was concluded that the formulation according to the invention
(a) releases Acyclovir 1.28 faster than the Comparator Acyclovir formulation at 15 minutes, and continues to release higher quantities throughout the duration of the test;
(b) releases Miconazole Nitrate 3.51 times faster than the commercial Comparator at 60 minutes.

Example 6

Demonstration of the Equivalent or Improved Bioavailability of Anti-TB Drugs in the Formulation According to the Invention Compared to a Commercially Available Product 1. Background:

Anti-tuberculosis treatment presents with two major problems—the development of drug resistance and compliance. The nanolipid based delivery system provides a system for single or combination tuberculosis drug treatment with a significantly increased therapeutic index, using currently prescribed anti-tuberculosis drugs, with a resultant decrease in the development of drug resistance. The delivery system contains the same therapeutic moieties but differs in chemical form, and dosage of those moieties and can therefore regarded as a pharmaceutical alternative. Furthermore, the higher therapeutic index of the drug facilitates lower dosage, which limits the side effects, which may in its turn be expected to improve compliance. Using this delivery system, delivery of the drugs may also be expanded to tissues usually not easily reachable by current therapeutic regimes.

The formulated delivery system contains components that have been recognized as pharmaceutically safe. The public health authority of South Africa in concert with many other health authorities, advise the same actives as used in this investigation as initial treatment regime for all tuberculosis patients. This protocol describes the delivery of the prescribed anti-TB drugs in 4 single daily doses by way of the delivery system at a reduced dosage level to 1 healthy volunteer.

In an open crossover design, pharmacokinetic parameters of the four drugs delivered by the test formulations in reduced doses were compared to those achieved when the same drugs were administered in the reference formulations of established quality and in the standard treatment doses. The volunteer was monitored daily during the study. The protocol below describes the dosage level, the specific drug, the time period of the study, the parameters investigated and the combinations of drugs used.

2. Study Objectives

Primary Objectives

The first primary objective of this investigation was to determine the bioavailability of generally used anti tuberculosis treatment agents, i.e. Rifampicin (R), Izoniazid (H), Ethambutol (E) and Pyrazinamide (Z), each packaged into the MZL drug delivery system in the form of the capsules produced in the manner as described in Preparation 3 above.

Secondly, it was to determine changes in patient global assessment, i.e. significant change from baseline of the following pharmacokinetic parameters:
 a) peak plasma concentration (Cmax),
 b) the time needed to reach this concentration (Tmax),
 c) exposure (the area under the plasma curve (AUC 0-9 hours), and
 d) coverage.

The pharmacokinetic results were compared with those of reference formulations. The packaged drugs were administered at an equal or a decreased dosage of that in the commercially available combination antituberculosis drugs.

2.2 Secondary Objectives

The secondary objectives of the investigation were firstly, to determine whether bioequivalence exists for drugs packaged into the delivery system by comparison to reference agents;

secondly, to determine whether there are changes in the status of side effects caused by the actives;

thirdly, to determine the relative safety levels of the comparative products;

fourthly, to determine possible partitioning of the MZL nanolipid delivered drugs to cells and possible cytotoxicity as a result; and finally, to note the possible advantages to the volunteer's well-being (i.e. malaise, bone ache, nausea etc) when using the delivery system of the invention for the administration of anti-tuberculosis drugs.

3. Study Design

The treatment was based on the Standard Treatment Guidelines and Essential Drugs List (1998). The study design was an open crossover bioavailability design of tuberculosis drugs [Rifampicin (R), Izoniazid (H); Ethambutol (E) and Pyrazinamide (Z)] delivered by a formulated drug delivery system. Bioavailability is understood to be the rate and extent to which the active substance or therapeutic moiety is absorbed and delivered from a pharmaceutical form
 a) into the general circulation and
 b) becomes available at the site of action.

As in other bioavailability studies, the kinetics of the therapeutic moiety in the general circulation was monitored in this study.

The study was conducted over two periods of 4 days each, interrupted by a two week wash out period. During the last day (day 4) of each period, blood samples will be taken at the times specified below to determine several pharmacokinetic parameters. Blood samples (10 ml each) were taken at the following intervals after administration of the drugs: 30 minutes, 1 hour, 2 hours, 3 hours, 4 hours, 6 hours, 9 hours.

3.1 Rifampicin:

The volunteer received the currently commercially available prescribed Rifampicin, namely Rifampin, treatment for 4 consecutive days, followed by a wash out period of 2 weeks. Rifampin contains Rifampicin as active ingredient. The volunteer then received pure Rifampicin packaged into the nanolipid delivery system of the invention as described above at two thirds of the prescribed dosage, again for 4 consecutive days. This nanolipid formulation of Rifampicin is herein also referred to as Rifemzaloid. The volunteer took the medication in the morning before a meal with 200 ml of tea, as food has been shown to influence absorption. Meals were standardized and supplied a couple of hours after first administration of the medication.

3.2 Combination Drugs:

The volunteer started with two third dosage of all four drugs packaged into the nanolipid delivery system of the invention, followed by the same scenario with the commercially available treatment regime, namely Rifafour, after a two week wash out period. The volunteer took the medication in the morning before a meal with 200 ml of tea, as food has been shown to influence absorption. Meals were standardized and supplied a couple of hours after first administration of the medication.

3.3 General Protocol Requirements:

a) The subject volunteered for participation in the study. The volunteer was a Caucasian middle-aged female and was clinically healthy i.e. blood chemistry, full blood count and liver function tests of subjects fell within the normal ranges. The volunteer granted written informed consent before participating in the study.

b) All drugs were orally administered in Soft Gel capsule form at applicable doses. The volunteer did not take any other chronic medication during the study.

c) The study was single blind for laboratory procedures. Plasma level assays of the actives were performed in the conventional manner.

d) Blood and liver function assays were undertaken in the conventional manner.

e) The safety of the treatments was assessed according to the ICH Clinical Trial Guidelines. No serious adverse events (AE) occurred during the study.

4 Treatment Regime:

4.1 Pharmaceutics

The nanolipid delivery system formulated as described above was used as a base for the active drugs used when comparing the pharmaceutical efficacy of drugs delivered by a delivery system with the generally prescribed drugs containing identical actives.

4.2 Dosing:

Rifampicin:

Commercially available Rifampin tablets (600 mg) were taken daily for four consecutive days, followed by sample collection on day 4.

Nanolipid formulated Rifampicin was taken in the same manner but at two thirds of the above dosage, i.e. 400 mg Rifampicin encapsulated in the delivery system. Dosing was again followed by a sample collection in order to determine the comparative pharmacodynamic profile of the active.

Combination Treatment:

The generally prescribed drug regime, consisting of 5 combination tablets Rifafour RHZE (120/60/300/200 mg) were taken daily for 4 consecutive days, after which blood samples were collected for plasma concentration analysis.

In the nanolipid combination formulation, 5 capsules containing a two third dosage of each of the actives i.e. RHZE 100/40/200/132 mg were taken and analysed in the same manner.

4.3 Study Supplies

The drugs used in the study were packaged into the nanolipid delivery system, manufactured according to Preparation 3 above and labelled in accordance with Good Laboratory and Manufacturing Practice (GLP and GMP) Guidelines for the labelling of study medication as set out in Table 8 below.

TABLE 8

Prescribed treatment: RHZE combination tablet

| Dosage | RHZE mg/tablet | RHZE mg/day | RHZE mg/week |
|---|---|---|---|
| Less than 50 kg | 120/60/300/200 | 480/240/1200/800 | 2400/1200/6000/4000 |
| more than 50 kg | 120/60/300/200 | 600/300/1500/1000 | 3000/1500/7500/5000 |

Drugs administered by drug delivery system

| Drug delivered treatment | Drug mg/capsule | Drug mg/day | Drug mg/week |
|---|---|---|---|
| Rifampicin; R | 100 mg | 400 mg | 2000 mg |
| Isoniazid; H | 100 mg | 200 mg | 1000 mg |
| Pyrazinamide; Z | 250 mg | 1000 mg | 5000 mg |
| Ethambutol; E | 132 mg | 660 mg | 3300 mg |

Prescribed treatment: RHZE combination tablet

| Dosage | RHZE mg/tablet | RHZE mg/day | RHZE mg/week |
|---|---|---|---|
| Less than 50 kg | 120/60/300/200 | 480/240/1200/800 | 2400/1200/6000/4000 |
| more than 50 kg | 120/60/300/200 | 600/300/1500/1000 | 3000/1500/7500/5000 |

Drugs administered by drug delivery system

| Drug delivered treatment | Drug mg/capsule | Drug mg/day | Drug mg/week |
|---|---|---|---|
| Rifampicin; R | 100 mg | 400 mg | 2000 mg |
| Isoniazid; H | 100 mg | 200 mg | 1000 mg |
| Pyrazinamide; Z | 250 mg | 1000 mg | 5000 mg |
| Ethambutol; E | 132 mg | 660 mg | 3300 mg |

4.4 Sample Collection and Preparation

Blood (10 ml) was collected at specified times for HPLC determination of the plasma concentrations of Rifampicin. Blood was also collected for liver function determinations and full blood cell counts.

Samples were collected in heparinized tubes and placed immediately on ice. Plasma was extracted by centrifugation within 15 minutes of collection and stored at a minimum of minus 80° C.

Blood samples were collected and handled in accordance with Good Clinical Procedures (GCP) Guidelines.

4.5 Plasma Concentration Determination

The concentrations of Rifampicin(RIF), Izoniazid(INH) and Pyrazinamide(PZA) and their active metabolites were determined by high performance liquid chromatography after their simultaneous extraction from plasma. The materials used were INH, RIF, PZA and pyrazynoic acid; HPLC-grade acetonitrile, methanol and trifluoroacetic acid (TFA) and C18 Bondelut extraction columns, 200 mg, 3 ml 40 microns.

The plasma concentrations of RIF were determined using a mobile phase of 80% acetonitrile in 0.1% trifluoracetic acid. A reversed phase C8 analytical column (Spherisorb, 250×4.6 mm ID, 5 um) linked to a C8 precolumn, with flow rate at 2.0 ml per minute and detection at 270 nm was used.

For the determination of INH and PZA, the mobile phase was 3% acetonitrile in 0.06%. TFA. A reversed phase C8 analytical column (Spherisorb, 150×4.6 mm ID, 5 um) linked to a C8 pre-column with flow rate at 1.5 ml per minute and detection at 254 nm was used.

Stock Standards

A stock standard solution of Rifampicin (0.5 mg/ml), PZA (0.5 mg/ml) and INH(0.5 mg/ml) and pyrazynoic acid were prepared (0.5 mg/ml) is prepared in Methanol.

Relative retention times were established by spiking and comparing peak area ratio of RIF.

INH and PZA.

All stock solutions are kept at a minimum of 4° C. and protected from light.

Specificity

Analyses of blank samples of the appropriate biological matrix were tested for endogenous interferences in the reference standard region for RIF, INH and PZA.

Calibration graphs (peak areas vs concentration) were constructed for RIF and INH in the range 0.1-20 µg/ml and for PZA in the range 0.1-60 µg/ml. INH, RIF and PZA and pyrazynoic acid analysis were done in triplicate.

Intra- and inter-assay coefficients of variation were determined.

Five replicate samples of four concentrations were run through the procedure with exactly controlled volumes, as described \ for the extraction of the samples. To verify recovery/quality control, precision and accuracy, the peak areas obtained for the extracted samples were be compared to those of fresh standards of the analytes in mobile phase with respect to the volumes handled during extraction.

C18 Bondelut extraction cartridges were washed sequentially with 2×2 ml of methanol, 2×2 ml of water and 2 ml of 0.05 M potassium phosphate, pH 4.5 (phosphate buffer) prior to application of the sample to the columns.

A 0.5 ml quantity of plasma were thawed and drawn slowly onto the column and allowed to stand for 5 minutes, after which time unbound material were discarded. The columns were washed with 1 ml of phosphate buffer to be discarded, and the drugs eluted with 0.5 ml of acetonitrile, followed by 0.5 ml of methanol with these elutes being pooled.

60 µl of the pooled eluates were injected immediately onto the HPLC column to assay for RIF.

INH, PZA and Pyrazynoic Acid:

0.5 ml of the combined eluates were dried by vacuum centrifugation and taken up in 0.5 ml of 3% acetonitrile in 0.06% TFA.

60 µl of this were injected onto the autosampler HPLC to assay for INH and PZA, which were detected together on the same column.

Acceptance Criteria:

A validated analytical method meets the following criteria:

Precision and accuracy: The between batch CVs for low, medium and high concentrations should be <15%, and 20% for the LOQ QC.

Sensitivity: The lowest standard should be, accepted as the LOQ if the % CV is <20%

Specificity: The responses of interfering peaks at the retention time of the analyte should be less than 20% of the response of an LOQ standard.

Stability: Stock solution stability should meet the criteria specified in the SOP.

5. Results 5.1 Comparative Bioavailability of Rifampicin

The first part of the study concerned only Rifampicin and the nanolipid-formulated Rifamzaloid. The plasma levels determined for the indicated times are reflected in Table 9.

TABLE 9

Plasma levels of Rifampicin

| Time (min) | MZLA Rifamzaloid (µg Rif/ml plasma) | Rifampicin (µg/ml plasma) |
| --- | --- | --- |
| 0 | 0 | 0 |
| 30 | 10.31 | 0 |
| 60 | 12.93 | 7.46 |
| 90 | 11.23 | 10.23 |
| 120 | 11.22 | 9.3 |
| 150 | 10.16 | 8.43 |
| 210 | 8.82 | 9.03 |
| 240 | 10.03 | 7.39 |
| 370 | 9.27 | 6.32 |
| 300 | 7.22 | 4.84 |
| 330 | 6 | 4.1 |
| 360 | 5.77 | 3.45 |

Increased Cmax

The maximum plasma concentration (Cmax) of Rifampicin was determined to be 12.93 µg/ml and was reached 60 minutes (Tmax) after oral administration of the active in the nanolipid delivery system. The Cmax obtained for the Rifampin (10.23 µg/ml) was reached 90 minutes after administration. The delivery of Rifampicin to the plasma was therefore increased by at least 21% at Tmax by the nanolipid carrier. Furthermore, only two thirds of the normal dosage was taken in the MZL formula. Therefore, the increased delivery of Rifampicin to plasma by the Nanolipid delivery system at Tmax was 181% that of its comparator at equal dosages.

Decreased Tmax

The minimum effective concentration of Rifampicin in plasma is 7 µg/ml. It is clear from the results that Rifampicin reaches its effective concentration much quicker when delivered by the Nanolipid delivery system. This is especially important in the case of unstable drugs such as Rifampicin, as increased gastric exposure may lead to increased loss of activity.

Increased Coverage

Coverage can be regarded as the time period during which the effective concentration is maintained. FIG. 6 illustrates that the coverage afforded by using the nanolipid delivery system is increased by 180% (270 minutes vs 150 minutes). It is therefore possible to the increase the time intervals between sequential dosages.

The above parameters reflect the comparative bioavailability dynamics of the Nanolipid delivery system. The total average increase in bioavailability by Nanolipid delivery system was 227%, while using only two thirds of the dosage of the comparator.

Differences in the above pharmacodynamic and pharmacokinetic parameters were statistically significant (see Table 10), with a p-value of 0.0157. The statistical method for analysis used was Analysis of Variance with a single factor variant.

TABLE 10

SUMMARY OF STATISTICAL ANALYSIS

| Groups | Count | Sum | Average | Variance |
| --- | --- | --- | --- | --- |
| Column 1 | 11 | 103.16 | 9.378182 | 4.944216 |
| Column 2 | 11 | 70.45 | 6.404545 | 9.408267 |

ANOVA

| Source of Variation | SS | df | MS | F | P-value | F crit |
| --- | --- | --- | --- | --- | --- | --- |
| Between Groups | 48.63382273 | 1 | 48.63382 | 6.77706 | 0.017005894 | 4.351250027 |
| Within Groups | 143.5248364 | 20 | 7.176242 | | | |

FIG. 6 hereto records the observed bioavailability of Rifampicin in the MZL formulated Rifamzaloid vs its comparator Rifampin. The comparative daily Rifampicin dosages were 400 mg/day in the case of Rifamzaloid and 600 mg/day in the case of Rifampin.

5.2 Bioavailability of Combination Drugs

Similar results were obtained with Isoniazid and Pyrazinamide. FIG. 7 hereto illustrates the enhancement in bioavailability of INH, using the nanolipid delivery system, and FIG. 8 that of Pyrazinamide (PZA).

Figure 1:
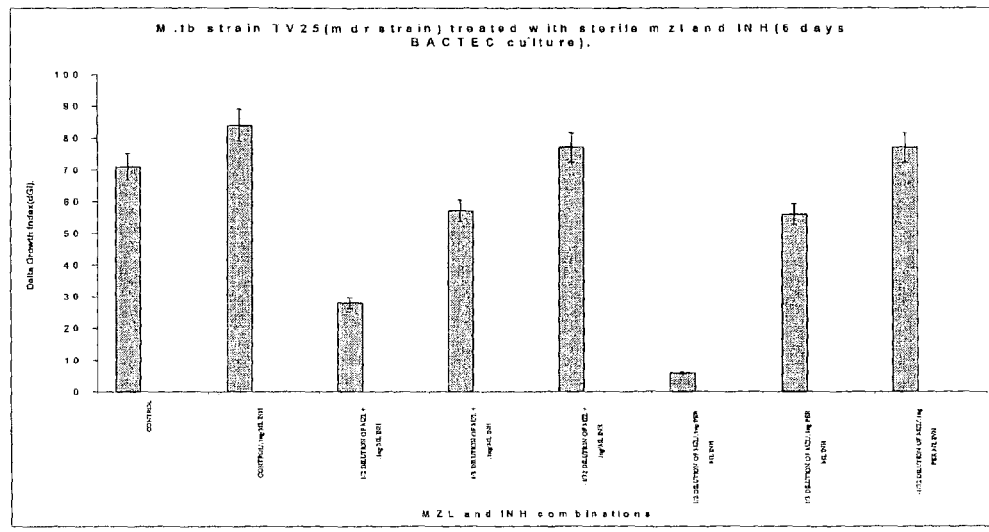
Figure 2:
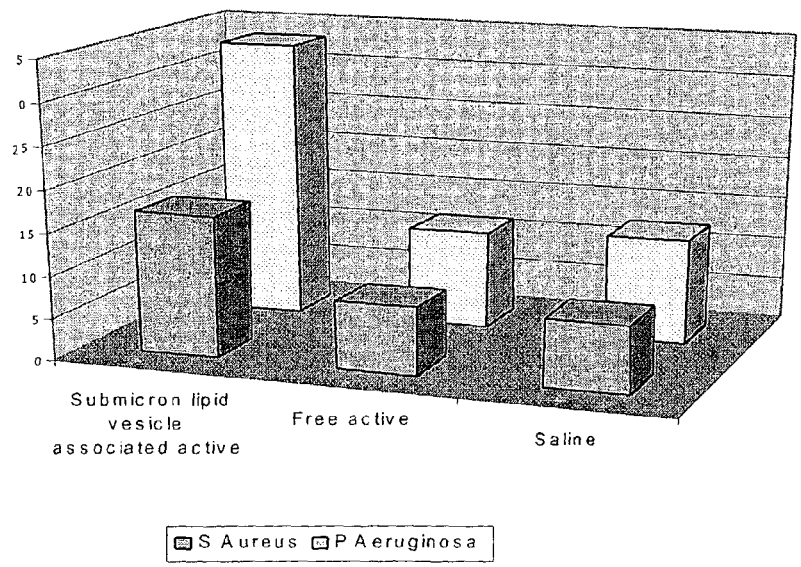
Figure 3:
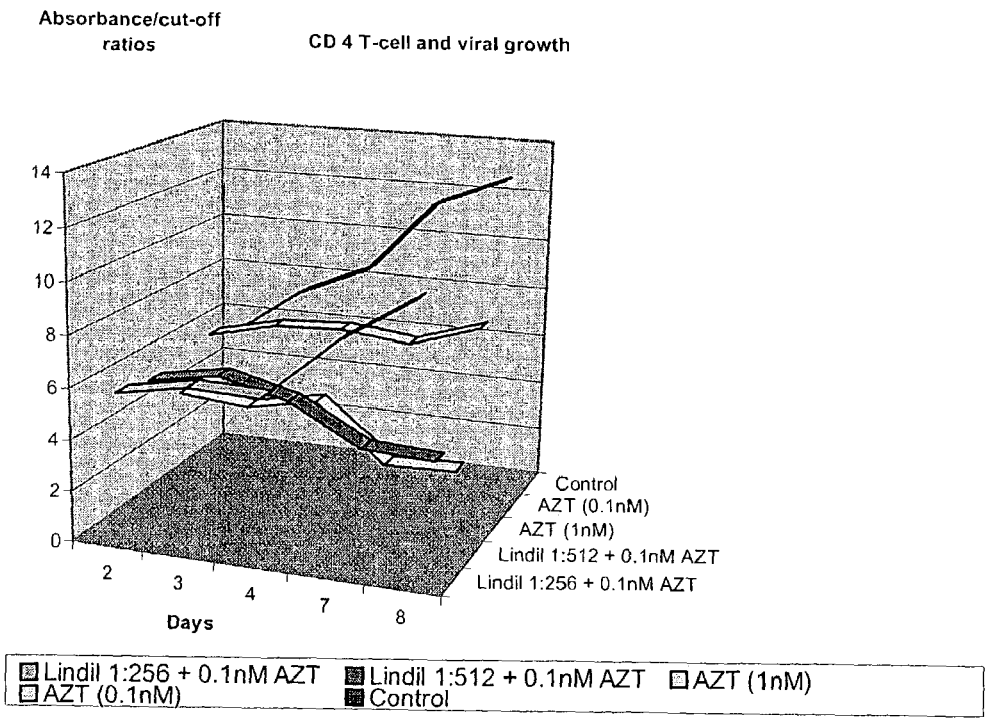
Figure 4:
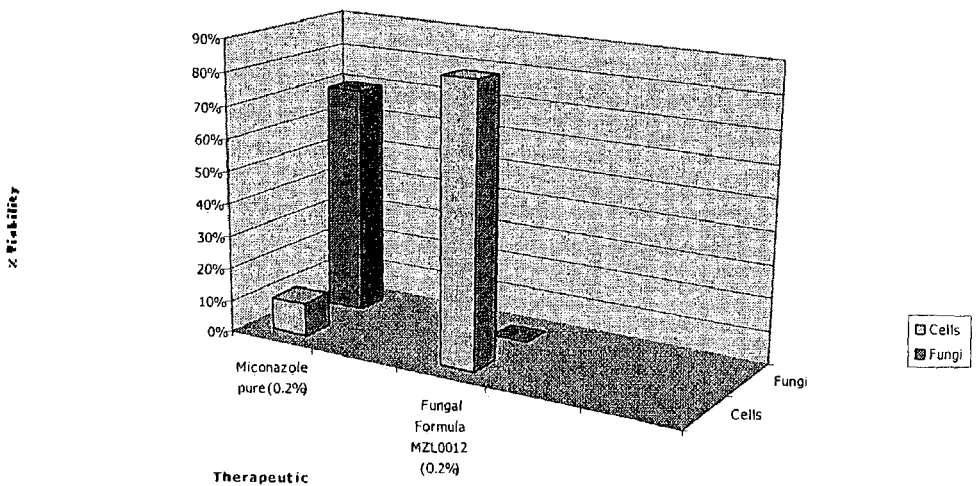
Figure 5:
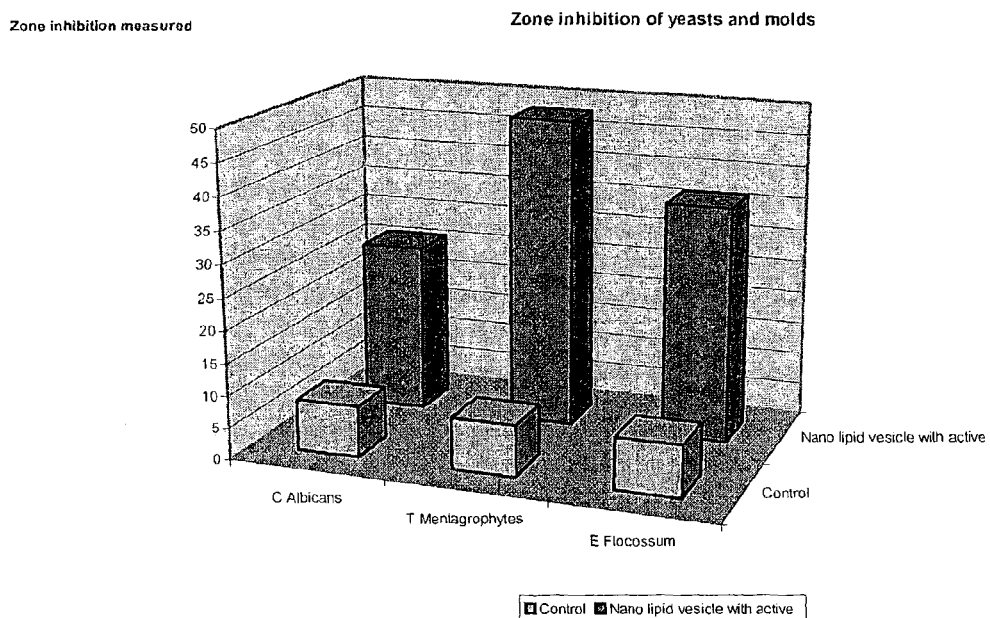
Figure 6:
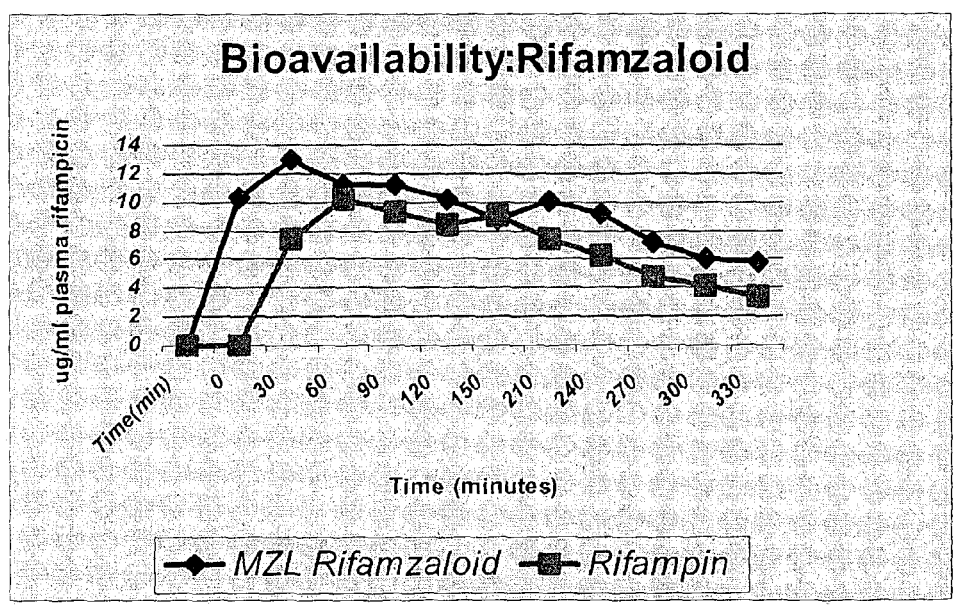
Figure 7:
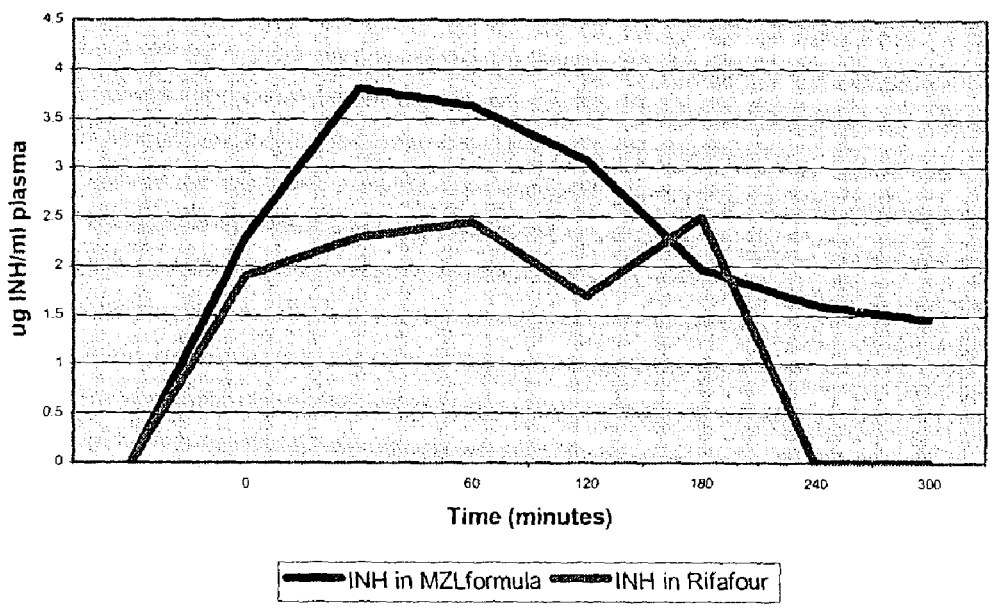
FIG. 7 shows the enhanced bioavailability of Izoniazid when encapsulated in the MZL delivery system, even though the daily dosage of the INH in the MZL formula was only two thirds of that of the comparator, Rifafour.
Figure 8:
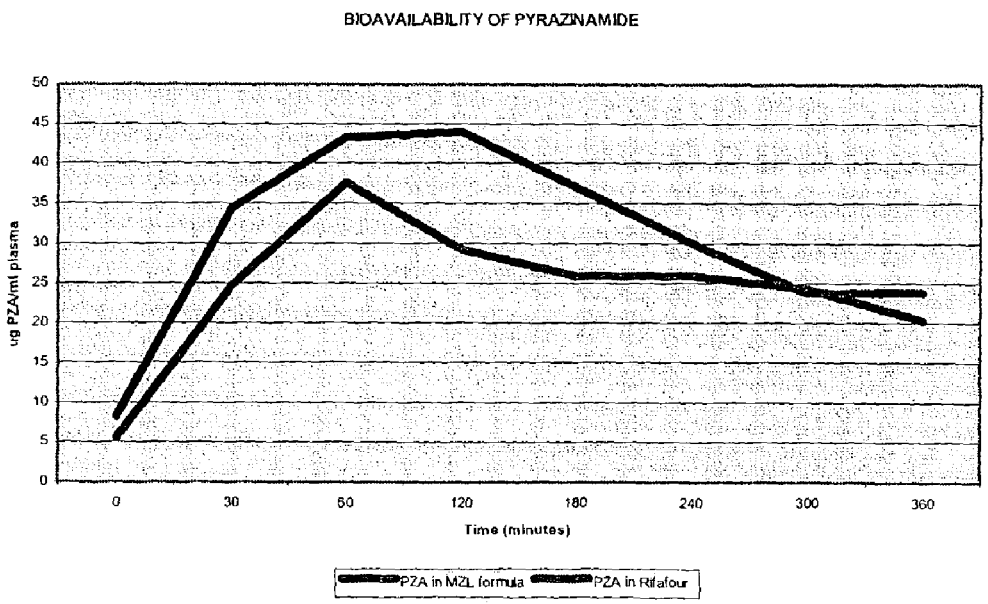
FIG. 8 illustrates the enhanced bioavailability of Pyrazinamide in the MZL formulation. Again the daily dosage of the PZA in the MZL formula was only two thirds of the PZA in Rifafour, the comparator.

5.3 Side Effects:

No significant side effects were found with the MZL formulated liver function analysis. None of the liver enzymes showed levels higher than the normal range. The S-unconjugated bilirubin, which did show levels elevated above the normal range was nearly back to normal 8 hours after drug administration, and was normal on the following day.

5.4 Volunteer's Assessment:

The only adverse reaction to either of the MZL formulas (Rifampicin or Combination) was nausea, whereas the comparator Rifafour led to serious headache, jitters and nausea.

5.5 Partitioning of nanolipid formulated Rifampicin:

Between 5-10% of the Rifampicin encapsulated in the nanolipid partitioned to blood cells rather than to plasma. This partitioning should increase the effective dosage delivered to the cells, but the partitioning is not so high as to be cytotoxic.

The study was repeated for Rifampicin and Pyrazinamide with similar results.

Example 7

Preparation of Topical Formulations of Doxepin Hydrochloride, Lidocaine Hydrochloride, and Scopolamine Hydrochloride in the Nanolipid Vesicle Formulation of Preparation 2

(a) A 2% composition of doxepin in the nanolipid-vesicle composition of Preparation 2 above was prepared by mixing doxepin hydrochloride with the nanolipid vesicle formulation as described in Preparation 2 which had been modified by the addition of Keltrol to render a thick creamy consistency, in a mass/mass ratio of 2:98 with the aid of a high speed stirrer. The composition is designated DOXIPEX CREAM.

(b) In similar manner a 1.7307% composition of Lidocaine Hydrochloride was prepared and designated LIDAREX LOTION.

(c) A 0.3% composition of Scopolamine HBR was also prepared in the same manner and designated MZL Scopolamine.

(d) A 0.5% nasal spray composition of Oxymetazoline HCl was also prepared in the same manner with some modification and designated Oxymetazoline MZL.

(e) A 0.5% injection formulation of Bupivicaine HCl was further prepared in the same manner but with some modification and designated Bupivicaine MZL.

Example 8

Study to Investigate the Release Characteristics of the Formulations Prepared in Terms of Example 1 Against Commercial Preparations 1. Objective:

The scope of the study was to establish whether the Test active agents viz.

Doxepin Hydrochloride,
Lidocaine Hydrochloride
Scopolamine Hydrobromide
Oxymetazoline HCl and
Bupivicaine HCl are released from the dosage forms prepared in accordance with the invention as described in Example 1, and to determine the extent and rate of such release. It was further done to compare the rate of release of Doxipex to that of an FDA approved 5% Doxepin Hydrochloride topical formulation which is commercially available in Canada where it is indicated for the treatment of pruritis associated with eczema. That product is herein referred to as DOXEPIN COM. The test further compares the release of Lidocaine Hydrochloride from LIDAREX against a commercially available Lidocaise Hydrochloride composition herein referred to as LIDOCAINE COM. The test further compared the release of the Oxymetazoline MZL to a commercially available oxymetazoline nasal spray formulation designated oxymetazoline Corn. Finally the test compares the release of the Bupivicaine MZL formulation with a commercially available Bupivicaine injection formulation designated Bupivicaine Corn.

The applicability of the method used to test for release out of the dosage forms is confirmed in Handbook of Dissolution Testing; Dissolution Testing of Transdermal Delivery Systems, page 61. The small receptor volume to be used, in this case 12 ml, is confirmed in the same reference.

2. Method

The in vitro release from the dosage forms was determined by a Hanson Model 57-6M, Manual Start-Up, Diffusion Cell Test System available from Hanson Research with the following main parts:

CELL DRIVE CONTROL
6-CELL DRIVE WITH CELLS
VERTICAL CELLS

3. Additional Equipment Used

1. Diffusion cell assembly, including donor top and receptor chamber (set of 6). The donor top includes a drug dosage wafer (Teflon washer), an acrylic top plate, and a clamp to connect top to bottom.
2. Pig skin, mucous membrane or Dura mater as applicable, used within 24 hours from being slaughtered kept in Ringer Solution between 2° C.-8° C.
3. Davies Gold Series Dermatome, Simplex GS102.
4. Application squeegee and tweezers.
5. Drug dosage form.
6. Absorbent paper towels and tissues.

4. Technique

The technique used included the following steps:

1. Obtain skin from pig heads (jawbone skin). Use Dermatome according to the Operation standard operating procedure for the Dermatome, setting it to size the skin to a thickness of 0.33 mm. The diameter of the skin should be in excess of the drug dosage wafer
OR For investigations using the active compound Oxymethalzoline MZL nasal spray, obtain the nasal mucous membrane of the pig in the following manner: the snout of the pig is removed just below the eyes with a stainless steel saw blade. The snout is cut in half between the nostrils. The cartilage is then gently cut and the nasal passage opened. The mucous membrane is carefully loosened and removed. Mucous membrane cells of 2.5 cm by 2.5 cm are cut. The membrane thickness is monitored with a micrometer

OR

For investigations using the active compound Bupivicaine MZL Injectable Solution, obtain the Dura mater (the tough membrane forming the barrier between the brain and cranium or blood) in the following manner: Open the cranium with a stainless steel saw blade. Divide the brain in disturbing the membrane. Loosen the membrane from the cranium and measure the width of the membrane with a micrometer. The thickness of the membrane should be between 0.19 and 0.24 mm. Cut at least 6 cells of 2.5 by 2.5 cm of membrane.

Prepare receptor chamber of diffusion cells with slight overflow of medium as specified in table below with temperature controlled at 32° C.

2. Prepare each piece of skin, mucous membrane or Dura mater with the relevant products one at a time as follows:

2.1. Lift skin, mucous membrane or Dura mater with tweezers, place on tissue and blot excess of solution, invert and blot.

3.2 Place skin, mucous membrane or Dura mater in centered position on drug dosage wafer.

3.3 3.3 Place relevant products on top of skin, mucous membrane or Dura mater in dosage wafer cavity.

3.4 Use squeegee to carefully smooth product over membrane, filling entire cavity.

3.5 Wipe excess dosage off wafer.

3.6 Lift loaded dosage wafer with skin, mucous membrane or Dura mater and place on top of receptor cell with skin, mucous membrane or Dura mater side towards cell medium. Exclude donor cell assembly, pressing down with finger, squeezing out bubbles between top plate and dosage form. Apply clamp to lock down top donor and bottom receptor halves of diffusion cell.

5. Operation of Apparatus:

The apparatus must be set to 150 rpm. Samples of 150 µl are withdrawn with a micropipette at 10, 20, 30, 60, 90 and 120 minutes. The samples after being withdrawn are analysed for the active compound by means of HPLC, using the parameter indicated in table below for each of the different compounds.

| | Doxipex And Doxepin Com | Lidarex And Lidocaine Com | Scopolamine MZL | Oxymetazoline HCl MZL and Oxymetazoline HCl | Bupivicaine MZL and Bupivicaine Com |
|---|---|---|---|---|---|
| Injection volume | 20 µl | 20 µl | 20 µl | 20 µl | 20 µl |
| Column | Zorbax C18 15 cm | Zorbax C18 250 mm × 4.6 mm | Zorbax SB C18 150 mm × 4.6 mm | Zorbax C18 250 mm × 4.6 mm | Zorbax C18 250 mm × 4.6 mm |
| Mobile Phase | 40% 0.2M $NaH_2PO_4$ buffer with 60% MeOH adj pH to 2.5 with $H_3PO_4$ | 50 ml GAA in 930 m $H_2O$ at pH 3.4 adj with 1N NaOH | 70% Phosphate buffer: 30% MeOH, pH 2.5 | 70% Phosphate buffer: 30% MeOH, pH 3.5 | 65% Acetonitrile: 35% Phosphate Buffer, pH 7.7 |
| Receptor chamber medium | PH 6.8 phosphate buffer | 40% MeOH/ 60% $H_2O$ | PH 6.8 phosphate buffer | PH 6.8 phosphate buffer | PH 6.8 phosphate buffer |
| Detector | HPLC at 254 nm | HPLC at 254 nm | HPLC at 240 nm | HPLC at 280 nm | HPLC at 263 nm |
| Temperature | Ambient (22° C.) | Ambient (22° C.) | Ambient (22° C.) | Ambient (22° C.) | Ambient (22° C.) |
| Flow Rate | 1.5 ml/min | 1.5 ml/min | 1.5 ml/min | 1 ml/min | 2 ml/min |
| Retention Time | 3-4 min | 5-6 min | 2.5-2.7 min | 4.85-5.07 min | 4.4-4.6 min |
| Solvent | 80% 0.2M $NaH_2PO_4$ buffer with 20% MeOH adj pH to 6.8 with 1N NaOH | MeOH/60% $H_2O$ | $KH_2PO_4$ buffer pH 6.8 | $KH_2PO_4$ buffer pH 6.8 | $KH_2PO_4$ buffer pH 6.8 |
| Cells used | 6 | 6 | 6 | 3 | 3 |
| Time at which total release determined (Min) | 60 | 30 | 15 | 8 | 5 |

6. Results

The release experiment was performed in 6 cells for each product and the mean release is reported for each analysis point. The results were tabulated and graphically presented. The results as a percentage of the active ingredient released per label claim per cell at the different time intervals was also tabulated.

Table 8.1 below gives a summary of the release rates and percentage release per label claim for the products determined according to calculations, reporting the mean values at 60 minutes (1 hour) for each of these compounds.

TABLE 8.1

Release rates and percentage release per label claim for products tested.

| Active Agent | % Active/product | Release Rate ($\mu g/cm^2/h$) | % Release per label claim |
|---|---|---|---|
| Doxipex | 2.00 | 112.9951 | 0.7945 |
| Doxepin Com | 5.00 | 45.6479 | 0.3190 |
| Lidarex | 1.7307 | 0.6954 | 0.0769 |
| Lidarex Com | 1.7307 | 0.5180 | 0.0573 |
| Scopolamine MZL | 0.3 | 21.13 | 0.63 |
| Oxymetazoline MZL | 0.5 | 0.35 | 0.0035 |
| Oxymethazoline Com | 0.5 | 0.33 | 0.0031 |
| Bupivicaine HCl MZL | 0.5 | 253.68 | 1.58 |
| Bupivicaine HCl Com | 0.5 | 226.75 | 1.35 |

The Release Rate was calculated as follows:

1. $\mu g$ Active Released at time (min.) =

$$\frac{Asam \times Mass\ Std \times VolReceptor \times Mass\ of\ Active\ Applied\ for\ Z\ cells \times C}{Astd \times Vol\ Std \times Label\ Claim \times Mass\ of\ Product\ Applied\ for\ 1\ cell \times Z \times 100}$$

WHERE:

| | |
|---|---|
| Asam = | Area of peak of sample solution |
| Astd = | Area of peak of standard solution |
| Mass Std = | Mass of standard taken to prepare the standard solution expressed in $\mu g$ |
| Vol Std = | Volume to which the standard solution is made up, expressed in ml |
| Vol Receptor = | Volume of diffusion cells system receptor chamber, expressed in ml. |
| Label Claim = | Amount of active present per 100 g of product |
| Mass of Product Applied for 1 cell = | Specific amount of product applied for a specific cell |
| Mass of Active Applied for Z cells = | Amount of active applied in total for all Z cells utilised per one study |
| C = | potency of the standard, expressed as a percentage |

2. Accumulative Dose ($\mu g$) released/square cm at time (min) =

$$\frac{\mu g\ Active\ Released}{(Surface\ Area\ of\ Exposed\ Skin)} = \frac{\mu g\ Active\ Released}{1.767\ cm^2}$$

3. Release Rate = $\frac{Accumulative\ Dose\ (\mu g)\ released/square\ cm}{Time\ (hours)}$ 4. Percentage of Active Released at time (min.) =

$$\frac{\mu g\ Active\ Released \times 100}{\mu g\ Active\ Applied}$$

It was established that

A. Doxipex Cream releases Doxepin hydrochloride 2.4754 times faster than the commercially available Doxepin Com product;

B. Lidarex releases Lidocaine HCl 1.3425 times faster than the commercially available Lidocaine Com product.

D. C. The release of Oxymetazoline HCLI from the MZL formulation compared well with that of the commercial Oxymetazoline Com formulation, but both values were very low, due to the thickness of the mucous membrane of the pig. The human mucous membrane is much thinner and release should accordingly be much higher in humans. The release of Bupivicaine from the MZL formulation was nevertheless shown to be 10.1% faster than that of the commercially available Bupivicaine formulation after 5 min and was about equal at all other times.

8. Conclusion

It is evident from the results obtained that the percentage active ingredient released from the DOXIPEX CREAM is significantly higher than that of the comparator Doxepin Com Cream. The release of Doxepin Hydrochloride from both the products consequently results in the effective administration of approximately the same quantity of active per dose although Doxipex contains 2% m/m Doxepin Hydrochloride and Doxepin Com 5% m/m Doxepin Hydrochloride in their respective formulations.

A comparison of the release rates at 60 minutes indicate that the release of Doxepin Hydrochloride from Doxipex Cream (2%) is at a rate 2.475 times greater than that from Doxepin Com Cream (5%). The percentage of active released from the formulation of the nanolipid vesicle formulation of Preparation 2 for this specific time is also 2.47 times greater than for the comparator.

Example 9

Clinical Studies

Below is described three examples of the use of the Doxepin MZL Formulation in three patients presenting with pain due to three different clinical causes.

Case Study 1. Use of Doxepin Formulation in Management of Lower Back Pain and Depression The doxepin in nanolipid formulation described above (DOXIPEX) was administered to the lower back area of a post-menopausal Caucasian woman suffering from manic depression associated with severe lower backache. Her depression was at the time reasonably under control through the use of PROZAC. She experienced substantial relief from the use of the formulation of the invention and discontinued her use of PROZAC after about 6 months on DOXIPEX. This is a most surprising result in view of the very low dose of doxepin hydrochloride administered through the topical application of the formulation of the invention.

Case Study 2. Use of Doxepin Formulation in Management of Pain in Reiter's Syndrome The doxepin in nanolipid formulation described above (DOXIPEX) was administered to the affected limbs of an active post-menopausal Caucasian woman diagnosed four years previously with Reiter's syndrome.

Clinical Symptoms in Volunteer:

Incapacitated and wasted right arm of the subject due to non-movement as a result of pain in the limb. The arm was carried in a light cast.

Previous Treatment of the Subject:

The subject was using intramuscular and/or oral pain relievers and muscle relaxants on a chronic basis since her diagnosis.

Dosage Form and Usage of the MZL Doxipin Formula:

MZL Doxipin was applied three times daily to the affected areas.

Progress:

After one month of usage, the subject no longer needed the support of the armcast. Muscle degeneration due to non-usage was reversed to some extent.

After 4 months of usage, the subject moved and used the arm freely. The wrist remained stiff.

Case Study 3: Use of Doxepin Formulation in Management of Severe Back Pain in a Degenerative Thoracic and Vertebral Condition.

Subject:

The subject was an 80 year old Caucasian male with severe back pain due to degeneration of his vertebrae. He was nearly completely immobilised by his condition and seldom moved outside of his home. He was on chronic therapy of intramuscular pain relievers and muscle relaxants.

Dosage form and usage of the MZL Doxepin formula:

In his case, synthetic polymer cutaneous patches were saturated with MZL Doxepin Formulation and attached at night to areas where he experienced extreme pain for prolonged release of the active compound.

Progress:

After a year of treatment, the subject was completely mobile. He stopped taking medication for pain, either of commercial origin or the Doxepin Formulation.

Example 10

Dissolution Studies in Respect of Formulations Made According to the Invention

Formulations of the active agents referred to below were prepared in the manner described above and were subjected to dissolution tests (2 or 3 repeats as indicated below) performed in terms of the USP 24 procedure. The following results were obtained.

| Product | Limits | Results |
| --- | --- | --- |
| Carbamazipine MZL suspension | NTL 75% in 30 min | 123%, 112%, 114% |
| Carbamazipine Com suspension | NTL 75% in 30 min | 111%, 112%, 112% |
| Zolpidem Tartrate MZL SGC | NTL 75% | 92%, 98%, ND |
| Zolpidem Tartrate Com SGC | NTL 75% | 102% 102% |
| Propranolol MZL SGC | NTL 75% in 30 min | 124% 126% 130% |
| Propranolol Com SGC | NTL 75% in 30 min | 106% 105% 107% |
| Phenythion Na MZL SGC | NTL 85% in 30 min | 143% 147% 155% |
| Phenythion Na Com SGC | NTL 85% in 30 min | 53%, 46%, 46% |

The advantages of the MZL formulations over the commercial formulations are self-evident.

Example 11

Study to Demonstrate the Nucleic Acid Transportation and Delivery Characteristics of the Transport Medium of the Invention Aim:

The scope of this study is to confirm that:

a) nucleic acids in its various forms could be stably entrapped in the nanolipid formulation of the present invention;

b) such entrapped nucleic acids could be transported across the cells membrane to cell nuclei, cell organelles or plasma;

c) the nanolipid formulation medium is not cytotoxic to cells;

d) The nanolipid formulation medium can be used to co-package various ligands with nucleic acid in the nanolipid vesicles, thereby targetting the nucleic acids to specific cell types by virtue of their cell surface antigens.

Three types of nucleic acids were selected for the investigation:

Linear double stranded (ds) human DNA

Circular ds DNA:

Oligodeoxynucleotides (ODN's)

Protocol:

Motivation for Investigating Linear Double Stranded (ds) DNA:

Using the vesicles of the nanolipid formulation medium as a delivery system for transgenes is considered to be body friendly and safe, without the cell damage caused by harsh physical methods or the disadvantages of viral vectors.

Motivation for Investigating Oligodeoxynucleotids and Ribozymes:

Due to the increase in drug resistance in the fight against infectious diseases, the use of antisense oligodeoxynucleotides (ODN's) for the inhibition of intracellular organism growth currently receives increasing attention. One of the ways in which ODN's can be used is to ensure the presence of ODN's of specific design in the cytoplasm. This can result in the formation of complementary base pairing between the ODN's and specific messenger RNAs, which can in turn inhibit the growth of the organisms.

Motivation for Investigating Circular DNA

A number of recombinant DNA vaccines use circular DNA, containing DNA engineered for vaccination against specific infectious agents. The physical state of the DNA transferred into cells by the delivery system may contribute to its survival and subsequent expression. The coiling and compaction of circular DNA differs from that of linear DNA, due to unrelieved supercoiling of the DNA. For that reason, it was considered necessary to confirm the entrapment of circular DNA into the nanolipid vesicle formulation of the invention.

Materials and Methods:
Nucleic Acids:
The following nucleic acids were used in the study.
a) Human placental DNA, fragmented to sizes averaging 800 bp (commercially available form Sigma);
b) recombinant circular DNA from vaccinia virus, obtained from University of Cape Town;
c) oligodeoxynucleotide designed by the Dept of Biochemistry of the University of Pretoria, South Africa. The ODN's were commercially manufactured with the inclusion of a FITC fluorescent label inherent in the design.

Cells:
The oncogenic cell line used in the study, designated UCT-1, was specifically cultured the University of Cape Town. Primary UCT-1 cells were cultured form a metastases of a patient's melanoma. The human melanoma cultured cells has all the major characteristics of fast growing cancer cells. The cells grow in adherent fashion.

The dendritic cells used were either the cell line THP-1 (ATCC) or primary macrophages, isolated and cultured from the blood of a donor.

The ODN approach was tested for the malaria parasite Plasmodium Falciparum. The mixture was fed to Plasmodium infected human red blood cell cultures, cultured in the presence of human serum from a donor.

Reagents:
Reagents used were obtained from commercial vendors, as specified in the procedure below. Fluorophores were from Molecular Probes (Holland) and included nile red, acridine orange, TMRM, ethidium bromide, Alexa Green, Baclight, carboxy fluorescien and $DIOC_6$.

Analysis
Confocal laser scanning microscopy (CLSM) was used to observe entrapment of nucleic acids in the nanolipid formulation medium. The dual wavelength CLSM was done on a Nikon PCM2000 microscope, with Kr/Ar and He/Ne lasers or a Zeiss LSM410, using the same lasers. Pinhole size generally used as 5 µM and smaller. Objectives used were oil-dispersion 60× and 100×. Light and fluorescent microscopy on a Nikon TE300 inverted microscope was digitally captured, using Nikon DMX video and Nikon Coolpix900 digital cameras.

To measure the inhibition of parasite growth when using antisense ODN's, the determination of % parasitaemia was by counting of the number of intracellular parasites per number of erythrocytes and by FACS analysis.

Typical Preparation of DNA for Encapsulation in Nanolipid Vesicle Transport Medium:
1. Six µg (10 µl) of isolated circular vaccinia virus DNA was labelled fluorescently with 1 µl of a 0.1 µg/ml Ethidium Bromide solution. Ethidium Bromide interchelates with double stranded DNA, resulting in green fluorescence at the laser excitation wavelength used.
   Ten µg of fragmented double stranded human placental DNA, fragmented to sizes averaging 800 bp, was also labelled as above.
   One µg of FITC-labelled oligodeoxinucleotides were used. In this case, the ODN's were not labelled with ethidium bromide.
2. Free fluorophores were removed by washing procedures, except where different methods are described. The typical washing procedure used is described below:
   Free ethidium bromide was removed by ethanol precipation of the DNA in the following manner:
   a) Three volumes of 99% ethanol and sodium acetate to a final concentration of 0.2M were typically added to the labelled DNA. The mix was left at overnight at −20° C. or 30 minutes at −80° C., after which the DNA was collected by micro-centrifugation for 30 minutes at 15 000 rpm.
   b) The collected nucleic acids were washed twice with 70% ethanol and air dried in laminar flow cabinet.
   c) The DNA was resuspended in 10ul of sterile water and checked by CLSM to confirm that the fluorescent labelling was successful.

Using the Nanolipid Vesicle Formulation as a Medium to Encapsulate the Labelled DNA.
1. Nanolipid vesicle formulation was filter steriized, using 0.45 um filters.
2. Typically between 100 and 500 µl of the nanolipid vesicle formulation was then mixed with the fluorophore Nile red (Molecular Probes, Holland) to a final concentration ranging from 10 nM to 50 nM. The amount of nanolipid vesicle formulation and Nile red used depended on the composition of the formulation as well as the propose cell type used. In the nanolipid vesicle formulation Nile red-associated fatty acids fluoresce in the red spectrum when excited by laser energy. Nile red not associated with or bound to fatty acids, and other lipids do not emit red fluorescence under those conditions. DNA itself fluoresces in the green spectrum.
3. The presence of fluorescent transport vesicles in the nanolipid transport medium was confirmed by CLSM.
4. Typically, the resuspended green fluorescent DNA was entrapped into nanolipid formulation medium by thorough mixing with between 100-500 µl of Nile red labelled nanolipid vesicle formulation medium, depending on the DNA load needed. Mixing was by 30 minutes sonication in a sonicating bath with low frequency, or by vigorous vortexing, or by slow homogenization. The mixing temperatures can be varied, but was typically between room temperature and 40° C.
5. Between 5 and 10 µl of the Nanolipid formulation medium with the entrapped DNA was spread thinly on a very thin glass cover slip (see below for specifications).
6. Encapsulation of the various forms of DNA referred to above into the vesicles of the nanolipid transport medium was confirmed by CLSM. Confirmation of the sizes of the entrapped DNA was done by horizontal agarose gel electrophoresis.
   The nanolipid transport medium was concentratedby 34% for use with the recombinant Vaccinia DNA and 50 µl of the concentrated medium was pre-labelled with nile red.

This part of the study accordingly confirms that nucleic acid substances in the form of the various forms of DNA are properly associated with the nanolipid vesicles of the formulation medium.

Delivery of Exogenous DNA into the Nucleus of Cells:
One of the major factors in determining the level of expression of the genes transferred into target cells are the survival and delivery of exogenous DNA to the nucleus. The procedure described below for the UCT-1 melanoma cells is an example and can with some modifications directly be applied the transfer of other types of nucleic acid to other cell types, such as dendritic cells.

Preparation of Melanoma Cells for DNA Transfer:
UCT-1 cells, stored in liquid Nitrogen in cryovials in the presence of 90% foetal bovine serum and 10% DMSO, were cultured in the following manner:
1. Working as quickly as possible, the cryogenic vial is transferred to a 37° C. water bath.

2. Using a sterile 10 ml polypropylene pipette and Pipettes®-akku the content of the cryovial is transferred to centrifuge tube suitable for tissue cultures.
3. The cells were diluted with 2 ml 37° C. media comprising of RPMI+10% FBS (foetal bovine serum) and 0.05% Gentamicin Sulphate.
4. The cells and media were gently mixed by shaking and then centrifuged for 1 min to loosely precipitate the cells.
5. The media was removed to eliminate any DMSO and replaced with 2 ml 37° C. media comprising of RPMI+ 10% FBS and 0.05% Gentamicin Sulphate.
6. Cells were gently resuspended, using a wide mouth pipette.
7. The cells were plated in sterile polystyrene (60×15 mm) tissue culture petri dishes.
8. Cells were cultured in Shellab $CO_2$ incubator at 37° C., 5% $CO_2$, and a relative humidity (RH) of ±89%.
   When the cells reached confluence, they were typically plated onto 31×0.017 mm glass cover slips with a refractive index suitable for Confocal Laser Scanning Microscopy (CLSM) in the following manner:
9. A petri dish with a confluent layer of cells was removed from the incubator and in a flow cabinet, the media was removed under vacuum.
10. Two ml Trypsin/EDTA (Gibco/BRL) was added to the dish and the cells returned for incubation in order to reverse adherence of the cells to the petri dish. Adherence of the cells to the petri dish was checked by light microscopy every two minutes.
11. During this time, cover slips with the specifications as described above, were sterilized. Sterilizing was done by dipping the cover slips in 70% ethanol and flaming the cover slip after the alcohol evaporated. Six sterilized cover slips were placed in a polypropylene 6 well multi-plate.
12. When the cells have lost adherence, 5 ml media (RPMI+10% FBS and 0.05% Gentamicin Sulphate) at 37° C. were added to the petri dish to dilute the Trypsin/EDTA.
13. The petri dish content was transferred to a centrifuge tube, and the cells were collected by centrifugation at 3000 r.p.m. for 1 min. The supernatant was removed under vacuum.
14. Three ml media (RPMI+10% FBS and 0.05% Gentamicin Sulphate) was carefully added and the cells gently resuspended.
15. In each well, onto the glass coverslip, 0.5 ml of the cell suspension was plated.
16. Adherence of the cells was checked by microscopy and as soon as the cells were adherent, media was added to a final volume of 1 ml.
17. The cells were incubated overnight at 37° C., 5% $CO_2$, and a RH of ±89%.
18. If the cells cultured on the cover slip were determined to be typical of its parent cells by microscopy, the procedure continued as follows:
19. One of the cover slips containing the adherent cells were placed into a cellular flow cell with the side with the cells facing up. The stainless steel flow cell was specifically designed to fit the stage of the Nikon PCM2000 confocal laser scanning microscope. The cover slip with its adherent cells then forms the thin glass base of the flow cell. The leak-free flow cell is completed with the use of sterilized rubber O-rings, a polymer spacer and a second sterile cover slip. Working very quickly, 1 ml of the described media at 37° C. was very gently added to the cells in the flow cell. The flow cell was checked for any tiny cracks in the cover silps and then fixed onto the stage of the CLSM and the cells left to stabilize.
20. To determine cytotoxicity of the nanolipid formulation medium, the same procedure was followed, but with the omission of any nucleic acids. A range of concentrations of the nanolipid vesicle transport medium was investigated, form undiluted to a 1000 fold dilution. The cells were exposed to the transport medium for periods ranging from 2 days to 14 days, with concomitant passaging of the cells when necessary.

Note: Dendritic cell, in this case THP-1 macrophages, were cultured and treated in a similar fashion, with the exception that the Gentamycin was omitted or used at a much reduced concentration, and only when necessary. When primary human macrophages were used, the foetal bovine serum was replaced with 20% AB human serum.

Transfer of Vaccinia Virus DNA into Melanoma Cell Nuclei by the Nanolipid Formulation Medium.

Note that this procedure can with some modifications be applied to double stranded linear DNA for delivery into the nuclei or cell organelles or the cytoplasm of other cell types as well.

1. Labelled DNA-loaded nanolipid vesicles were isolated by differential micro-centrifugation. Care was taken that the internal water phase of the vesicles was not depleted. During the differential centrifugation steps, the status of the internal water phase was monitored by CLSM.
2. Typically between 5 and 100 ul of the labelled DNA-loaded MZL vesicles were carefully and gradually added to the medium of the melanoma cells by the inlet in the prepared flow cell or by removing the top glass cover slip of the flow cell.
3. Transfer of the DNA in the nanolipid vesicle formulation were allowed to continue for between 15 to 60 minutes, after which time the cell medium was removed and replaced with fresh cell medium that contained no DNA-loaded nanolipid formulation medium.
4. Progress of DNA transport into the melanoma cell nuclei was followed and confirmed by CLSM.

This part of the investigation thius confirmed that the DNA associated nanolipid vesicles duly entered the melenoma cell.

Furthermore, the release of the labelled DNA from the nanolipid vesicle transport medium inside the cell nuclei and inside the cell cytoplasm were also confirmed by CLSM.

Attachment of a Peptide to the Nanolipid Formulation Medium Vesicles.

1. The procedure described below can be used for a variety of macromolecules, including antibodies, enzymes and glycoproteins.
2. 100 mg of the peptide was pre-labelled with Fluorescein Diacetate (FA) to a final concentration of 10 nM. FA emits green fluorescence when exposed to the applicable laser line.
3. The peptide was entrapped in the concentrated Nanolipid formulation medium as described above.
4. The incorporation of the peptide into Nanolipid formulation medium vesicles and sponges were followed by light video microscopy and CLSM as described above.

Results:

1. Entrapment of Nucleic Acids by the Nanolipid Formulation Medium

The entrapment of nucleic acids in the nanolipid transport medium vesicles was illustrated by CLSM. The nucleic acids were entrapped in the vesicles. Nucleic acids in the process of being entrapped were visualized by its green fluorescence. Co-localization between the Nanolipid formulation medium vesicles and green nucleic acids were similarly visualized. The loading efficiencies were high—between 85% and 95% at the concentrations of nucleic acid and Nanolipid formulation medium used. Nearly all vesicles showed entrapped DNA.

The percentage loading efficiency can be calculated by $$\frac{\text{Nr of vesicles containing nucleic acid}}{\text{Total nr of vesicles}} \times 100$$

Most nucleic acids are entrapped in the hydrophilic centre of the vesicles, sponges or depots. Circular DNA can be visualized where the DNA follows the contour of individual vesicles, tightly associated with the interior layer of the vesicles membrane.

Stability of Nucleic Acids Entrapped in Nanolipid Formulation Medium

The stability of nucleic acids in the Nanolipid formulation medium was confirmed by CLSM investigation: at room temperature, there was no obvious degradation or digestion of the entrapped nucleic acid for several weeks after preparation of the entrapped nucleic acids. The delivery of the nucleic acids to cells were typically done 1 week after entrapment of the nucleic acids in the nanolipid vesicle transport medium.

Delivery of Exogenous DNA into the Nucleus of Cells:

In vitro experiments with both dendritic and oncogenic cell lines confirmed the uptake of exogenous nucleic acids entrapped in the nanolipid vesicle transport medium. In both the oncogenic Melanoma UCT-1 cells, and in the dendritic THP-1 cells, delivery to the cytoplasm, the mitochondrial genome and the nucleus could be demonstrated.

In the THP-1 macrophage cell line, the uptake of the entrapped exogenous nucleic acid was by two mechanisms: a process of phagocytosis, or by transport across the cell membrane. In the melanoma cell, transport to the nucleus and mitochondria were across the cell membrane, by way of the cytoplasm. The presence of a few intact nanolipid vesicles in the cytoplasm could be demonstrated.

Release of the nucleic acids from the MZL vesicles was demonstrated in both the cytoplasm and the nucleus by optical sectioning and 3D-reconstruction of the cells on the CLSM. The release of the nucleic acid from the vesicles in the nucleus is necessary before DNA can be integrated into the endogenous genome for transcription. Release in the cytoplasm is especially important in the case of the ODN's, where the ODN's would result in inhibition of protein synthesis of infective agents. Research with both susceptible and drug-resistant strain of the intracellular parasite Plasmodium Falciparum in the in vitro human erythrocyte system showed that antisense oligodeoxynucleotides, entrapped by the nanolipid vesicle transport medium, can be used to inhibit the growth of the parasites in the red blood cell cultures.

Targeting of the Nanolipid Formulation Medium Vesicles:

The attachment of peptides into nanolipid formulation vesicles was demonstrated. The current data suggests that the peptides are attached to outer membrane of the vesicles by strong electrotatic bonds. The attachment to the outer vesicle membrane has the advantage that recognition between the peptide and the cell recognition antigen/receptor can occur without any steric hindrance. The peptide used in the experiments described above, was targeted to melanoma cells and fibroblasts. In additional experiment, using another ligand, the ligand have been shown to retain receptor recognition activity whilst packaged in nanolipid vesicle transport medium. These packaged vesicles can thus be targeted to cells containing the appropriate receptor. It is our belief that the same will hold true for other macromolecules, such as antibodies.

Toxicity and Cytotoxicity:

Cytotoxicity: No cytoxicity was observed at the concentrations used under experimental conditions (1:300 to 1:1000 dilution of the Nanolipid formulation medium, diluted with RPMI medium). No adverse effects were observed at these concentrations. The cells were sensitive to undiluted Transport Medium if exposed to it for long periods (>1 day).

General Safety:

VITAMIN F: Since the constituents in vitamin F comprise the n-essential fatty acids, which are fundamental to normal physiological processes, it is unlikely to be inherently toxic. It could theoretically be toxic if consumed at levels far higher than those normally available to the body. For example, the estimated endogenous rate of formation of the intermediate, gamma linolenic acid within the body of a normal adult was put at 100-1000 mg, or around 2-20 mg/day. It was also estimated that daily intake of GLA in a human fully breast fed infant is of the order of 20-80 mg/kg/day. Based on these estimates, it seems unlikely that doses of less than 100 mg/kg/day will have any toxicity (Horrobin DF. Nutritional and medical importance of gamma-linolenic acid. Lipid Res, 1992. 31(2): 163-194). Long term animal toxicity studies have shown that doses of evening primrose oil of up to 5 ml or 10 ml/kg/day given for up to two years has no toxicity (Everett DJ, Perry CJ, Bayliss P. Med Sci Res. 1988; 16:865-866).

Cremophor: From the available literature it is concluded that Cremophor administered intravenously may elicit certain dose-dependent toxicity characteristics. There is no evidence to suggest that the same is true for oral administration forms. In fact, in a study using oral administration of the drug paclitaxel in combination with Cremaphor EL, results showed undetectable plasma Cremaphor levels. It was concluded that this finding would have a beneficial influence on the safety of treatment with the MZL Nucleic Acid Transport Medium, especially when it is used in its prodrug form for oral administration. In this form, any Exipient (see Textbook of Exipients) may be added, which in itself refers to the safety and indicates the prescribed dosages.

Conclusions

The nanolipid vesicle administration or transport medium is a formulation capable of encapsulating macromolecules and delivering them with high efficacy to target sites. Furthermore, the encapsulating vesicles have been shown to penetrate through the cell membrane and to migrate to cell organelles. This study shows the efficient transport and delivery of DNA to such cell organelle, including the nuclei of the cells.

The major steps in the transfection process, ie the entry of DNA into the cell, the trafficking of the transgene through the cytoplasm, including both endosomal and lysosomal compartments, the entry of DNA into the nucleus or cell organelle, such as the mitochondria or the targeting of the nucleic acid to an intracellular infective agent, such as parasite or the targeting to the nucleic acids of such infective agents in the cellular cytoplasm and the ability to escape intracellular mechanisms designed to purge foreign nucleic acids, has in one way or another been addressed by these studies, with positive results.

This product has several unique advantages:

(i) It is a highly effective gene transfer vector and much more efficient than conventional products currently on the market (ii) One of the most interesting and exciting properties is that it can be used to package ligands so that vesicles can be targeted to specific cell surface receptors for uptake by these cells.

(iii) It can be used to transfer molecules trans-dermally, orally or through the any of the mucous membranes without the need for sophisticated procedures.

Many variations of the invention are possible without depating from the spirit of the invention.

The invention claimed is:

1. A method of enhancing the action of an anti-infective agent, comprising the step of formulating the agent with an administration medium,
   which medium is liquid and consists of a saturated solution of nitrous oxide in a pharmaceutically acceptable solvent, and
   a member selected from the group consisting of
     a fatty acid,
     a derivative thereof, and
     a reaction product of ethylene oxide with a hydrogenated natural oil comprising ricinoleic acid,
     wherein said anti-infective agent is selected from the group consisting of Rifampicin, Izoniazid, Pyrazinamide and Ethambutol.

2. The method of claim 1, further comprising the step of formulating said anti-infective agent for pulmonary administration.

3. A pharmaceutical composition comprising an anti-infective agent and an administration medium,
   which medium is liquid and consists of a
   saturated solution of nitrous oxide in a pharmaceutically acceptable solvent, and
   a member selected from the group consisting of
     a fatty acid,
     a derivative thereof, and
     a reaction product of ethylene oxide with a hydrogenated natural oil comprising ricinoleic acid,
   wherein said anti-infective agent is selected from the group consisting of Rifampicin, Izoniazid, Pyrazinamide and Ethambutol.

4. A method of enhancing the action of an anti-infective agent, comprising the step of formulating the agent with an administration medium, which medium is liquid and consists of a saturated solution of nitrous oxide in a pharmaceutically acceptable solvent, and
   a member selected from the group consisting of
     a fatty acid,
     a derivative thereof, and
     a reaction product of ethylene oxide with a hydrogenated natural oil comprising ricinoleic acid,
     wherein said anti-infective agent is selected from the group consisting of Acyclovir, Ciprofloxacin, Chloroquin, Cloxacillin, CoTrimoxazole (Trimethoprim+Sulphamethoxazole), Erythromycin E, Ethambutol, Isoniazid, Itraconazole, Miconazole, Povidone-Iodine, Pyrazinamide, Rifampicin, and Zidovudine;
     wherein said fatty acid is selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3] and ricinoleic acid; and
     wherein said derivative thereof is selected from the group consisting of a C1 to C6 alkyl ester and a glycerol-polyethylene glycol ester of said fatty acid.

5. A pharmaceutical composition comprising an anti-infective agent and an administration medium, which medium is liquid and consists of a saturated solution of nitrous oxide in a pharmaceutically acceptable solvent, and
   a member selected from the group consisting of
     a fatty acid,
     a derivative thereof, and
     a reaction product of ethylene oxide with a hydrogenated natural oil comprising ricinoleic acid,
     wherein said anti-infective agent is selected from the group consisting of Acyclovir, Ciprofloxacin, Chloroquin, Cloxacillin, CoTrimoxazole (Trimethoprim+Sulphamethoxazole), Erythromycin E, Ethambutol, Isoniazid, Itraconazole, Miconazole, Povidine-Iodine, Pyrazinamide, Rifampicin, and Zidovudine;
     wherein said fatty acid is selected from the group consisting of oleic acid, linoleic acid, alpha-linolenic acid, gamma-linolenic acid, arachidonic acid, eicosapentaenoic acid [C20: 5ω3], decosahexaenoic acid [C22: 6ω3] and ricinoleic acid; and
     wherein said derivative thereof is selected from the group consisting of a C1 to C6 alkyl ester and a glycerol-polyethylene glycol ester of said fatty acid.

* * * * *

UNITED STATES PATENT AND TRADEMARK OFFICE
CERTIFICATE OF CORRECTION

| | | |
|---|---|---|
| PATENT NO. | : 8,329,685 B1 | Page 1 of 1 |
| APPLICATION NO. | : 10/345204 | |
| DATED | : December 11, 2012 | |
| INVENTOR(S) | : Petrus Johannes Meyer | |

It is certified that error appears in the above-identified patent and that said Letters Patent is hereby corrected as shown below:

Title page, insert Item (30)

--(30)  Foreign Application Priority Data

July 19, 2000 (ZA)   2000/03643

July 19, 2000 (ZA)   2000/03644--

Signed and Sealed this
Nineteenth Day of February, 2013

Teresa Stanek Rea
*Acting Director of the United States Patent and Trademark Office*